(12) United States Patent
Philip

(10) Patent No.: US 11,273,216 B2
(45) Date of Patent: Mar. 15, 2022

(54) UNIVERSAL INFLUENZA VACCINE COMPOSITIONS

(71) Applicant: Emergex Vaccines Holding Limited, Oxfordshire (GB)

(72) Inventor: Ramila Philip, Ivyland, PA (US)

(73) Assignee: EMERGEX VACCINES HOLDING LIMITED, Oxfordshire (GB)

( * ) Notice: Subject to any disclaimer, the term of this patent is extended or adjusted under 35 U.S.C. 154(b) by 0 days.

(21) Appl. No.: 16/475,602

(22) PCT Filed: Jan. 3, 2018

(86) PCT No.: PCT/GB2018/050004
§ 371 (c)(1),
(2) Date: Jul. 2, 2019

(87) PCT Pub. No.: WO2018/127689
PCT Pub. Date: Jul. 12, 2018

(65) Prior Publication Data
US 2019/0321460 A1 Oct. 24, 2019

Related U.S. Application Data

(60) Provisional application No. 62/441,659, filed on Jan. 3, 2017.

(51) Int. Cl.
*A61K 39/145* (2006.01)
*A61P 31/16* (2006.01)
*A61K 39/00* (2006.01)

(52) U.S. Cl.
CPC ............ *A61K 39/145* (2013.01); *A61P 31/16* (2018.01); *A61K 2039/55555* (2013.01); *A61K 2039/55566* (2013.01); *A61K 2039/572* (2013.01); *A61K 2039/575* (2013.01); *A61K 2039/70* (2013.01)

(58) Field of Classification Search
None
See application file for complete search history.

(56) References Cited

U.S. PATENT DOCUMENTS

2014/0302124 A1* 10/2014 Philip .................. A61K 39/145
424/450
2015/0152140 A1* 6/2015 Sorensen ............. C07K 14/005
424/186.1

FOREIGN PATENT DOCUMENTS

| WO | 2002/32404 | A2 | 4/2002 |
| WO | 2006/037979 | A2 | 4/2006 |
| WO | 2007/015105 | A2 | 2/2007 |
| WO | 2007/122388 | A2 | 11/2007 |
| WO | 2013/034726 | A1 | 3/2013 |
| WO | 2013/059403 | A1 | 4/2013 |

OTHER PUBLICATIONS

Tambunan et al., Vaccine Design for H5N1 Based on B-and T-cell Epitope Predictions, 2016, Bioinformatics and Biology Insights, vol. 10, pp. 27-35.*
Sun et al. Functional Gold Nanoparticle-Peptide Complexes as Cell-Targeting Agents, 2008, Langmuir, vol. 24, pp. 10293-10297).*
Tkachenko et al., Multifunctional Gold Nanoparticle-Peptide Complexes for Nuclear Targeting, 2003, JACS Communications, vol. 123, pp. 4700-4701.*
Marin et al., Glyconanoparticles for the plasmonic detection and discrimination between human and avian influenza virus, 2013, Org. Biomol. Chem., vol. 11, pp. 7101-7107.*
Marradi et al., Glyconanoparticles as multifunctional and multimodal carbohydrate systems, 2013, Chem Soc Rev, vol. 42, pp. 4728-4745.*
Monsalvo et al. "Severe pandemic 2009 H1N1 influenza disease due to pathogenic immune complexes" Nat Med. Feb. 2011; 17(2): 195-199.
Anderson et al. "Aself-adjuvanting vaccine induces cytotoxic Tlymphocytes that suppress allergy" Nature Chemical Biology, vol. 10, Nov. 2014.
Atsmon et al., Safety and immunogenicity of multimeric-001—a novel universal influenza vaccine. Journal of clinical Immunology. 2012;32(3):595-603. Epub Feb. 10, 2012. doi: 10.1007/s10875-011-9632-5. PubMed PMID: 22318394.
Ben-Yedidia et al., Intranasal administration of peptide vaccine protects human/mouse radiation chimera from influenza infection. Int Immunol. 1999; 11(7): 1043-51. PubMed PMID: 10383936.
Beyer and Schultze, Immunoregulatory T cells: role and potential as a target in malignancy. Curr Oncol Rep. 2008;10(2):130-6. PubMed PMID: 18377826.
Boon et al., Sequence variation in a newly identified HLA-B35-restricted epitope in the influenza A virus nucleoprotein associated with escape from cytotoxic T lymphocytes. J Virol. 2002;76(5):2567-72. PubMed PMID: 11836437.
Burlington et al., Hemagglutininspecific antibody responses in immunoglobulin G, A, and M isotypes as measured by enzyme-linked immunosorbent assay after primary or secondary infection of humans with influenza A virus. Infect Immun. 1983;41(2):540-5. PubMed PMID: 6874068.
Choppin et al., Studies of two kinds of virus particles which comprise influenza A2 virus strains. II. Reactivity with virus inhibitors in normal sera. J Exp Med. 1960;112:921-44. PubMed PMID: 13693272.
De Groot et al., Immunoinformatic comparison of T-cell epitopes contained in novel swine-origin influenza A (H1N1) virus with epitopes in 2008-2009 conventional influenza vaccine. Vaccine. 2009;27(42):5740-7. PubMed PMID 19660593.

(Continued)

*Primary Examiner* — Benjamin P Blumel
(74) *Attorney, Agent, or Firm* — Norton Rose Fulbright US LLP

(57) ABSTRACT

The invention provides a vaccine composition comprising an influenza virus peptide comprising a CD8+ T cell epitope and an influenza virus peptide comprising a B cell epitope, wherein each peptide is attached to a nanoparticle.

12 Claims, 16 Drawing Sheets
Specification includes a Sequence Listing.

(56) References Cited

OTHER PUBLICATIONS

Doherty et al., Roles of alpha beta and gamma delta T cell subsets in viral immunity. Annu Rev Immunol. 1992;10:123-51. PubMed PMID:1534240.

Dredge et al.. Adjuvants and the promotion of Th1-type cytokines in tumour immunotherapy. Cancer Immunol Immunother. 2002;51(10):521-31. PubMed PMID: 12384803.

Eichelberger et al., Clearance of influenza virus respiratory infection in mice lacking class I major histocompatibility complexrestricted CD8+ T cells. J Exp Med. 1991;174(4):875-80 PubMed PMID: 1919440.

Epstein et al., Beta 2-microglobulin-deficient mice can be protected against influenza A infection by vaccination with vaccinia-influenza recombinants expressing hemagglutinin and neuraminidase. J Immunol. 1993;150(12):5484-93. PubMed PMID: 8390536.

Epstein et al., Mechanism of protective immunity against influenza virus infection in mice without antibodies. J Immunol. 1998;160(1):322-7. PubMed PMID: 9551987.

Fiers et al. A "universal" human influenza A vaccine. Virus research. 2004;103(1-2):173-6. Epub May 28, 2004. doi:10.1016/j.virusres.2004.02.030. PubMed PMID: 15163506.

Fifis et al., Sizedependent immunogenicity: therapeutic and protective properties of nano-vaccines against tumors. J Immunol. 2004;173(5):3148-54. PubMed PMID: 15322175.

Fonteneau et al., Activation of influenza virus-specific CD4+ and CD8+ T cells: a new role for plasmacytoid dendritic cells in adaptive immunity. Blood. 2003;101(9):3520-6. PubMed PMID: 12511409.

Graham and Braciale, Resistance to and recovery from lethal influenza virus infection in B lymphocyte-deficient mice. J Exp Med. 1997;186(12):2063-8. PubMed PMID: 9396777.

Grandea et al., Human antibodies reveal a protective epitope that is highly conserved among human and nonhuman influenza A viruses. Proc Natl Acad Sci U S A. 2010;107(28):12658-63. Epub Jul. 10, 2010. doi: 10.1073/pnas.0911806107. PubMed PMID: 20615945; PubMed Central PMCID: PMC2906546.

Gras et al., Crossreactive CD8+ T-cell immunity between the pandemic H1N1-2009 and H1N1-1918 influenza A viruses. Proc Natl Acad Sci U S A. 2010;107(28):12599-604. Epub Jul. 10, 2010. doi:10.1073/pnas.1007270107. PubMed PMID: 20616031; PubMed Central PMCID: PMC2906563.

Greenbaum et al., http://iedb.zendesk.com/forums/45499/entries/35037 Knowledgebase and Forums / Epitope analysis in emerging H1N1 swine flu viruses / Analysis version 1.0) 2009.

Heeney JL, Requirement of diverse T-helper responses elicited by HIV vaccines: induction of highly targeted humoral and CTL responses. Expert Rev Vaccines. 2004;3(4Suppl):S53-64. PubMed PMID: 15285705.

Hensley et al., Murine norovirus infection has no significant effect on adaptive immunity to vaccinia virus or influenza A virus. J Virol. 2009;83(14):7357-60. PubMed PMID: 19403665.

Huang et al., The plasticity of dendritic cell responses to pathogens and their components. Science. 2001;294(5543):870-5. PubMed PMID: 11679675.

Jameson et al., Human cytotoxic T-lymphocyte repertoire to influenza A viruses. J Virol. 1998;72(11):8682-9. PubMed PMID: 9765409.

Johansson et al., Purified influenza virus hemagglutinin and neuraminidase are equivalent in stimulation of antibody response but induce contrasting types of immunity to infection. J Virol. 1989;63(3): 1239-46. PubMed PMID: 2915381.

Kamperschroer et al., SAP is required for Th cell function and for immunity to influenza. J Immunol. 2006;177(8):5317-27. PubMed PMID: 17015717.

Kanekiyo et al., Selfassembling influenza nanoparticle vaccines elicit broadly neutralizing H1N1 antibodies. Nature. 2013;499(7456):102-6. Epub May 24, 2013. doi: 10.1038/nature12202. PubMed PMID: 23698367.

Karkada et al. A Novel Breast/Ovarian Cancer Peptide Vaccine Platform that Promotes Specific Type-1 but not Treg/Tr1-Type Responses J Immunotherapy. 2009:in press.

Kilbourne ED., What are the prospects for a universal influenza vaccine? Nat Med. 1999;5(10):1119-20. PubMed PMID:10502805.

Kircheis et al., Immunization of Rhesus monkeys with the conjugate vaccine IGN402 induces an IgG immune response against carbohydrate and protein antigens, and cancer cells. Vaccine. 2006;24(13):2349-57. PubMed PMID 16406172.

Kreijtz et al., Primary influenza A virus infection induces cross-protective immunity against a lethal infection with a heterosubtypic virus strain in mice. Vaccine. 2007;25(4): 612-20. PubMed PMID: 17005299.

Lee et al., Memory T cells established by seasonal human influenza A infection cross-react with avian influenza A (H5N1) in healthy individuals. J Clin Invest. 2008;118(10):3478-90. Epub Sep. 20, 2008. doi: 10.1172/JCI32460. PubMed PMID: 18802496; PubMed Central PMCID:PMC2542885.

Man et al., Definition of a human T cell epitope from influenza A non-structural protein 1 using HLA-A2.1 transgenic mice. Int Immunol. 1995;7(4):597-605. Epub Apr. 1, 1995. PubMed PMID:7547687.

Marshall et al., TH cells primed during influenza virus infection provide help for qualitatively distinct antibody responses to subsequent immunization. J Immunol. 1999;163(9):4673-82. PubMed PMID: 10528164.

McKinstry et al. Hallmarks of CD4 T cell immunity against influenza. Journal of internal medicine. 2011;269(5):507-18. Epub Mar. 3, 2011. doi:10.1111/j.1365-2796.2011.02367.x. PubMed PMID: 21362069; PubMed Central PMCID:PMC3395075.

McMichael et al., Cytotoxic T-cell immunity to influenza. N Engl J Med. 1983;309(1):13-7. PubMed PMID: 6602294.

Morse et al., MHC class I-presented tumor antigens identified in ovarian cancer by immunoproteomic analysis are targets for T cell responses against breast and ovarian cancer. Clin Cancer Res. PubMed PMID: 21300761.

Mullooly et al., Influenza vaccination programs for elderly persons: cost-effectiveness in a health maintenance organization. Ann Intern Med. 1994; 121(12): 947-52. PubMed PMID: 7978721.

Murphy et al., Secretory and systemic immunological response in children infected with live attenuated influenza A virus vaccines. Infect Immun. 1982;36(3):1102-8. PubMed PMID: 7095844.

Neuzil et al. Influenza: New Insights Into an Old Disease. Curr Infect Dis Rep. 2000; 2(3): 224-30. PubMed PMID 11095860.

Ngo-Giang-Huong et al., HIV type 1-specific IgG2 antibodies: markers of helper T cell type 1 response and prognostic marker of long-term nonprogression. AIDS Res Hum Retroviruses. 2001;17(15):1435-46. PubMed PMID: 11679156.

Novak et al., MHC class II tetramers identify peptidespecific human CD4(+) T cells proliferating in response to influenza A antigen. J Clin Invest. 1999;104(12):R63-7. PubMed PMID: 10606632.

Ojeda et al., Preparation of multifunctional glyconanoparticles as a platform for potential carbohydrate-based anticancer vaccines. Carbohydr Res. 2007;342(3-4):448-59. PubMed PMID: 17173881.

Paul and Benacerraf, Functional specificity of thymus—dependent lymphocytes.Science. 1977;195(4284):1293-300. PubMed PMID: 320663.

Philip et al., Shared immunoproteome for ovarian cancer diagnostics and immunotherapy: potential theranostic approach to cancer. J Proteome Res. 2007;6(7):2509-17. PubMed PMID: 17547437.

Pleguezuelos et al., Synthetic Influenza vaccine (FLU-v) stimulates cell mediated immunity in a double-blind, randomised, placebo-controlled Phase I trial. Vaccine. 2012;30(31):4655-60. Epub May 12, 2012. doi:10.1016/j.vaccine.2012.04.089. PubMed PMID: 22575166.

Price et al., Viral escape by selection of cytotoxic T cell-resistant variants in influenza A virus pneumonia. J Exp Med. 2000;191(11):1853-67. PubMed PMID: 10839802.

Ramakrishna et al., Naturally occurring peptides associated with HLA-A2 in ovarian cancer cell lines identified by mass spectrometry are targets of HLA-A2-restricted cytotoxic T cells. Int Immunol. 2003;15(6):751-63. PubMed PMID: 12750359.

Reddy et al., Exploiting lymphatic transport and complement activation in nanoparticle vaccines. Nat Biotechnol. 2007;25(10):1159-64. PubMed PMID: 17873867.

(56) References Cited

OTHER PUBLICATIONS

Richards et al., Cutting edge: CD4 T cells generated from encounter with seasonal influenza viruses and vaccines have broad protein specificity and can directly recognize naturally generated epitopes derived from the live pandemic H1N1 virus. J Immunol. 2010;185(9):4998-5002. Epub Oct. 5, 2010. doi:10.4049/jimmunol. 1001395 PubMed PMID: 20889549.

Rimmelzwaan and Osterhaus, Cytotoxic T lymphocyte memory: role in crossprotective immunity against influenza? Vaccine. 1995;13(8):703-5. PubMed PMID: 7483784.

Roti et al., Healthy human subjects have CD4+ T cells directed against H5N1 influenza virus. J Immunol. 2008;180(3):1758-68. Epub Jan. 23, 2008. PubMed PMID: 18209073; PubMed Central PMCID: PMC3373268.

Shelock DJ and Shen H., Requirement for CD4 T cell help in generating functional CD8 T cell memory. Science. 2003;300(5617):337-9. PubMed PMID: 12690201.

Shetty et al., MHC class I presented lung cancer-associated tumor antigens identified by immunoproteomics analysis are targets for cancer-specific T cell response. J Proteomics.74(5):728-43. PubMed PMID: 21362506.

Sinnathamby et al., Priming and Activation of human ovarian and breast cancer-specific CD8+ T cells by polyvalent Listeria monocytogenes-based vaccines. J Immunotherapy. 2009;32(8):856-69.

Stambas et al., Killer T cells in influenza. Pharmacology & therapeutics. 2008;120(2):186-96. Epub Sep. 20, 2008. doi:10.1016/j.pharmthera.2008.08.007. PubMed PMID: 18801385.

Subbarao et al., Development of effective vaccines against pandemic influenza. Immunity. 2006;24(1):5-9. PubMed PMID: 16413916.

Sun et al., Effector T cells control lung inflammation during acute influenza virus infection by producing IL-10. Nat Med. 2009;15(3):277-84. Epub Feb. 24, 2009. doi: 10.1038/nm.1929. PubMed PMID: 19234462; PubMed Central PMCID:PMC2693210.

Tan et al., Highly conserved influenza A sequences as T cell epitopesbased vaccine targets to address the viral variability. Hum Vaccin. 2011;7(4):402-9. Epub Apr. 8, 2011. PubMed PMID: 21471731.

Tao et al. Gold nanoparticle-M2e conjugate coformulated with CpG induces protective immunity against influenza A virus. Nanomedicine (Lond). 2013 Epub Jul. 9, 2013. doi: 10.2217/nnm.13.58. PubMed PMID: 23829488.

Testa et al., Conserved MHC class I-presented dengue virus epitopes identified by immunoproteomics analysis are targets for cross-serotype reactive T-cell response. J Infect Dis. 2012;205(4):647-55. Epub Jan. 17, 2012. doi: 10.1093/infdis/jir814. PubMed PMID: 22246683.

Testa et al., MHC class I presented T cell epitopes identified by immunoproteomics analysis are targets for a cross reactive influenza-specific T cell response. PLoS One. 2012;7(11):e48484. Epub Nov. 13, 2012. doi: 10.1371/journal.pone.0048484. PubMed PMID: 23144892; PubMed Central PMCID: PMC3492461.

Testa et al., Role of T-cell epitope-based vaccine in prophylactic and therapeutic applications. Future virology. 2012;7(11):1077-88. Epub May 1, 2013. doi:10.2217/fvl.12.108. PubMed PMID: 23630544; PubMed Central PMCID: PMC3636528.

Thomas et al., Hidden epitopes emerge in secondary influenza virus-specific CD8+ T cell responses. J Immunol. 2007;178(5):3091-8. PubMed PMID: 17312156.

Wilkinson et al., Preexisting influenza-specific CD4+ T cells correlate with disease protection against influenza challenge in humans. Nat Med. 2012;18(2):274-80. Epub Jan. 31, 2012. doi:10.1038/nm. 2612. PubMed PMID: 22286307.

Woodland et al., Cellular immunity and memory to respiratory virus infections. Immunol Res. 2001;24(1):53-67. PubMed PMID: 11485209.

Yap et al., Role of T-cell function in recovery from murine influenza infection. Cell Immunol. 1979;43(2):341-51. PubMed PMID: 113108.

Yap et al., Transfer of specific cytotoxic T lymphocytes protects mice inoculated with influenza virus. Nature. 1978;273(5659):238-9. PubMed PMID:306072.

Yewdell et al., Influenza A virus nucleoprotein is a major target antigen for cross-reactive anti-influenza A virus cytotoxic T lymphocytes. Proc Natl Acad Sci U S A. 1985;82(6):1785-9. PubMed PMID: 3872457.

Knuschke et al., "Immunization with Biodegradable Nanoparticles Efficiently Induces Cellular Immunity and Protects against Influenza Virus Infection", J Immunol 2013; 190:6221-6229; Prepublished online May 10, 2013. (http://www.jimmunol.org/content/190/12/6221).

Zhao et al., "Nanoparticles Vaccine", Vaccine 32 (2014) 327-337.

Dykman et al: Nanoparticles in Biomedical Applications: Recent Advances and Perspectives. Acta Naturae, vol. 3, No. 2 (9) 2011, pp. 36-58.

Notification of Request for Supplementary Materials from the Eurasian Patent Office issued in Application No. 201991377 dated Dec. 21, 2021.

Safari et al., "Gold nanoparticles as carriers for a synthetic *Streptococcus pneumoniae* type 14 conjugate vaccine", *Nanomedicine*, 7(5), 2012.

\* cited by examiner

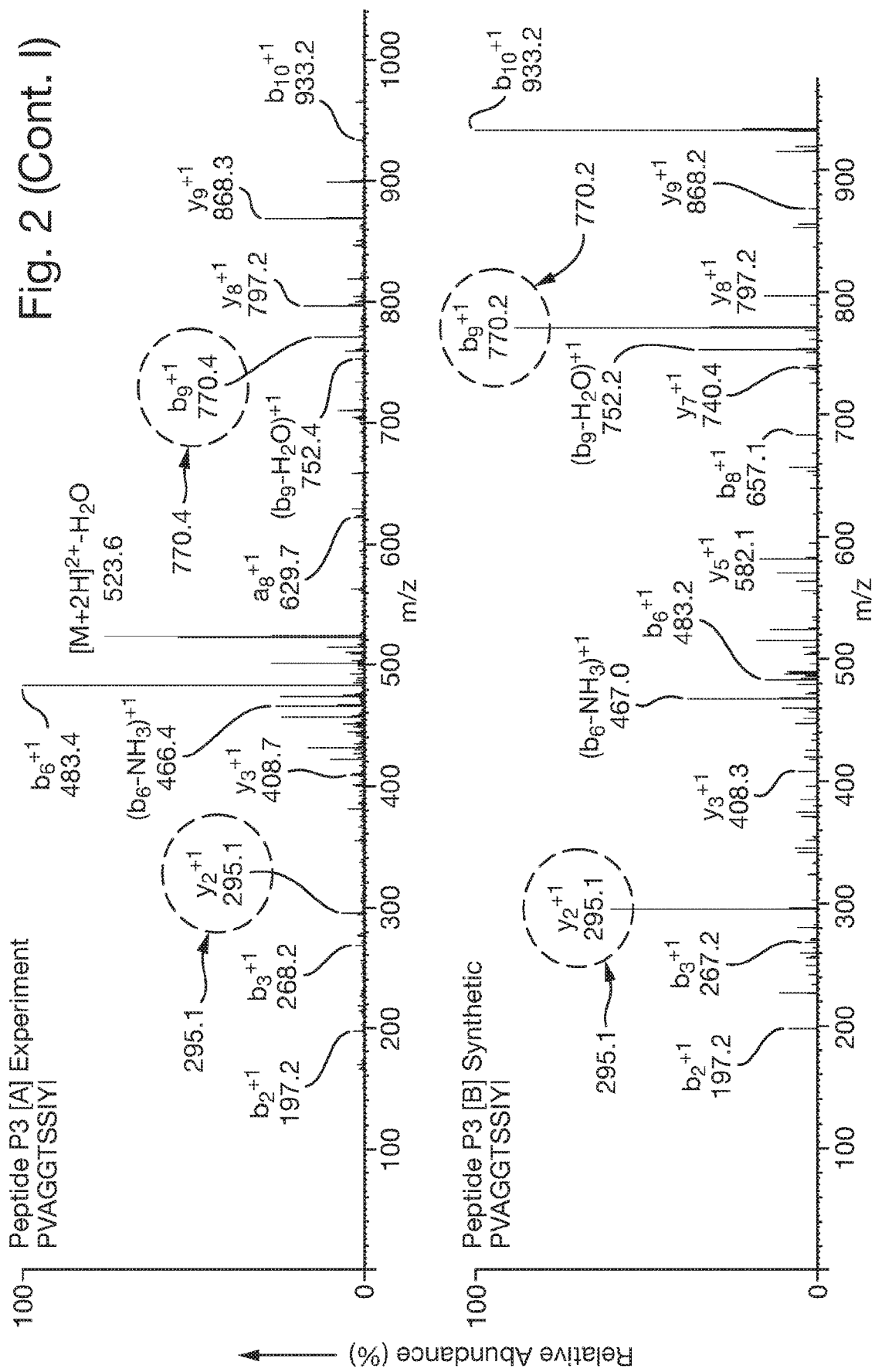

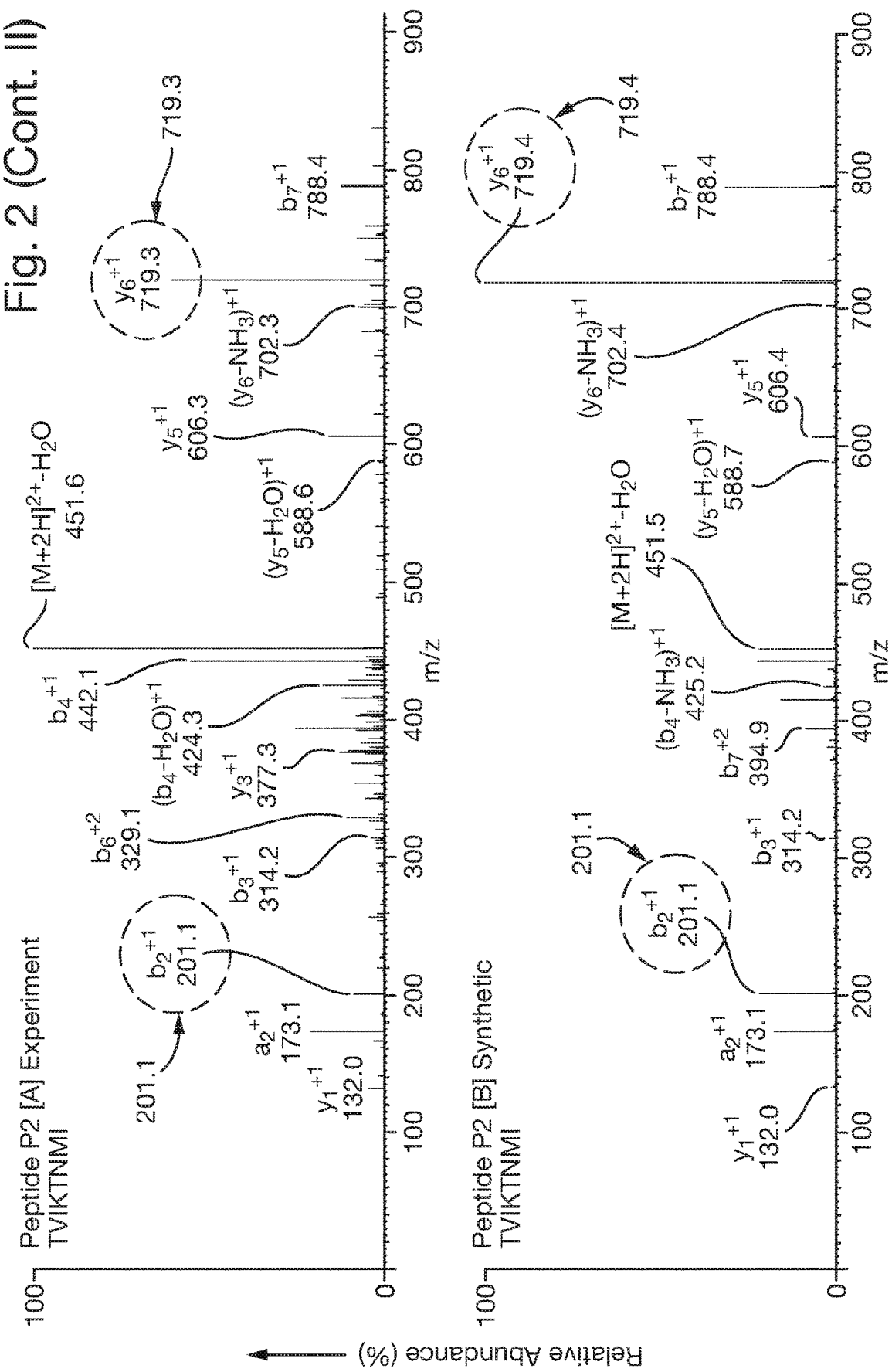
Fig. 2 (Cont. III)

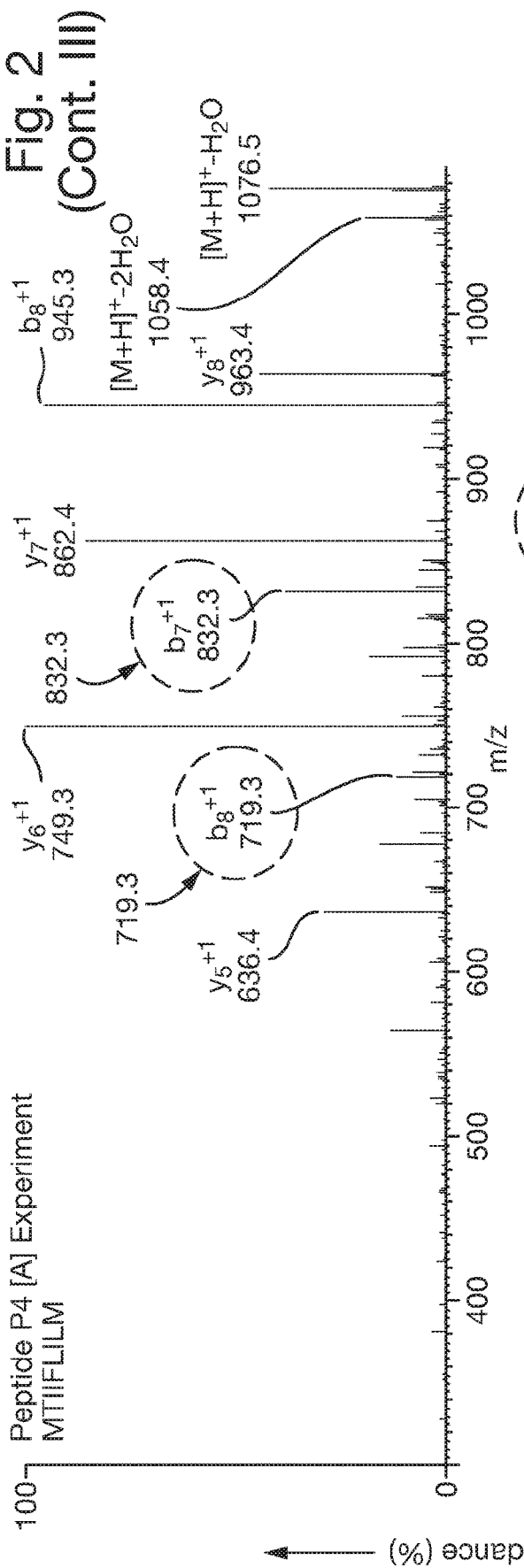
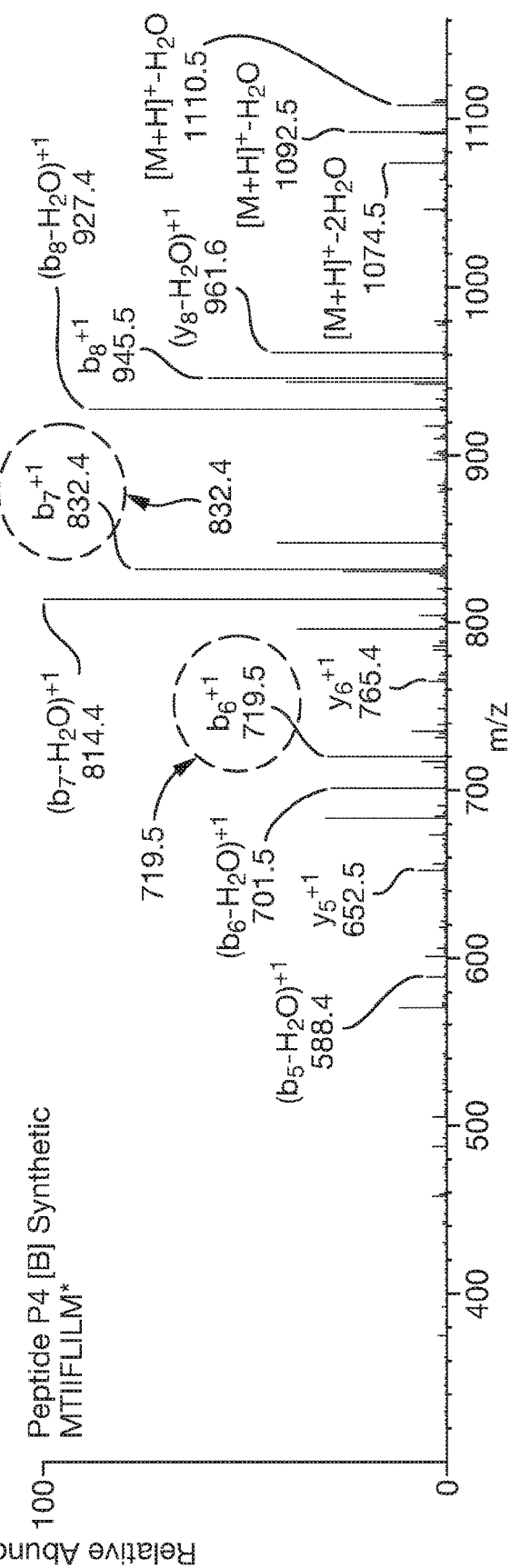
Fig. 2 (Cont. III)

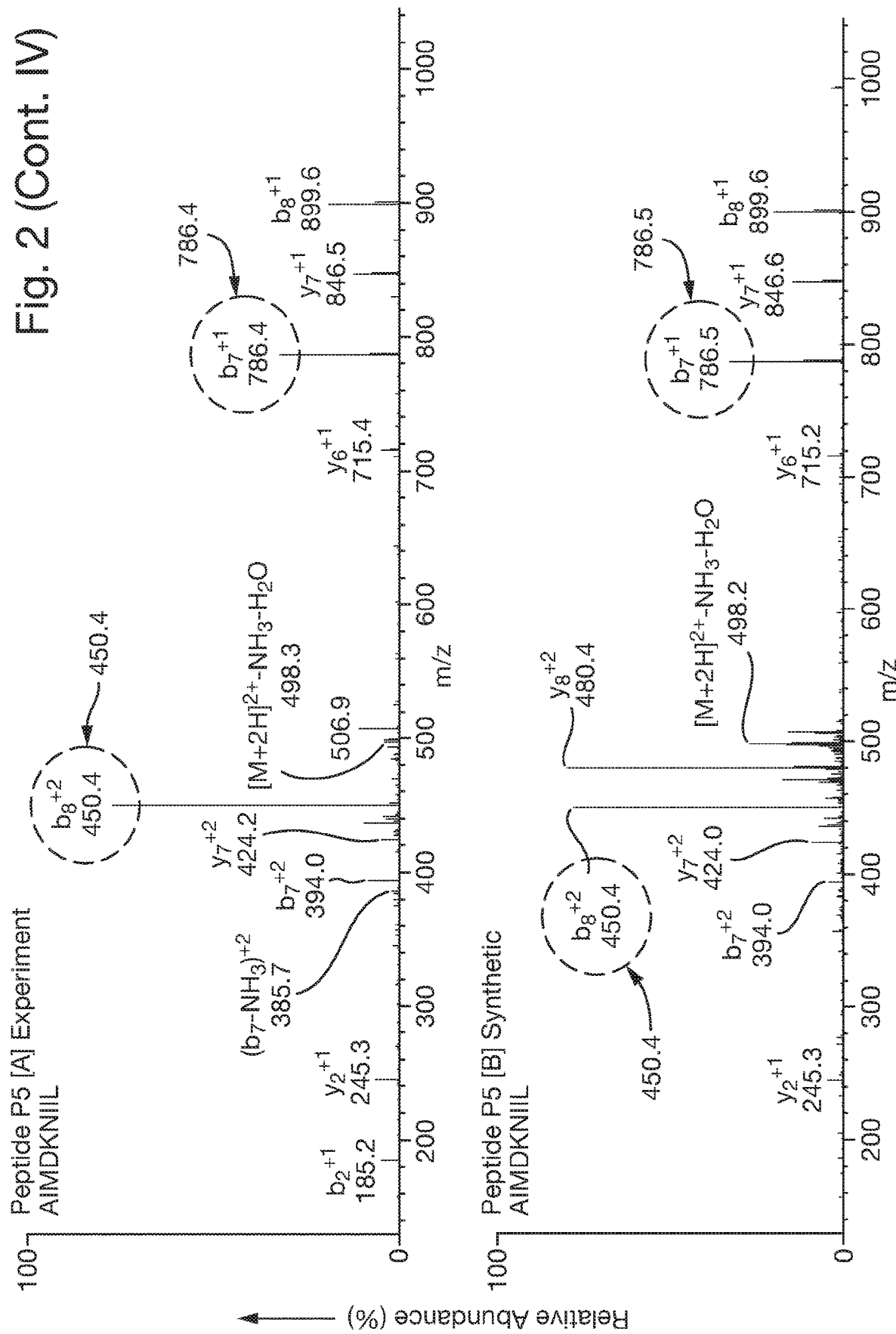
Fig. 2 (Cont. IV)

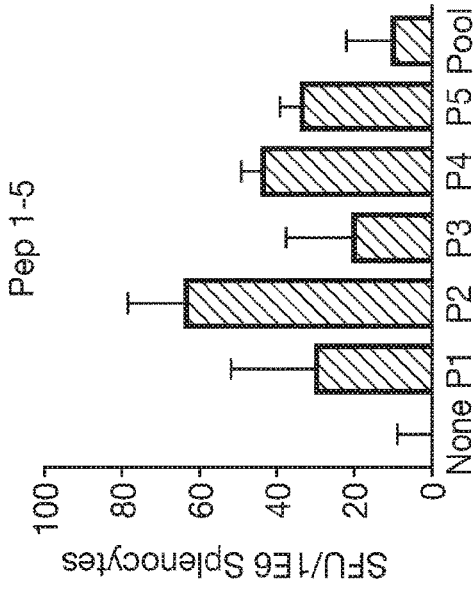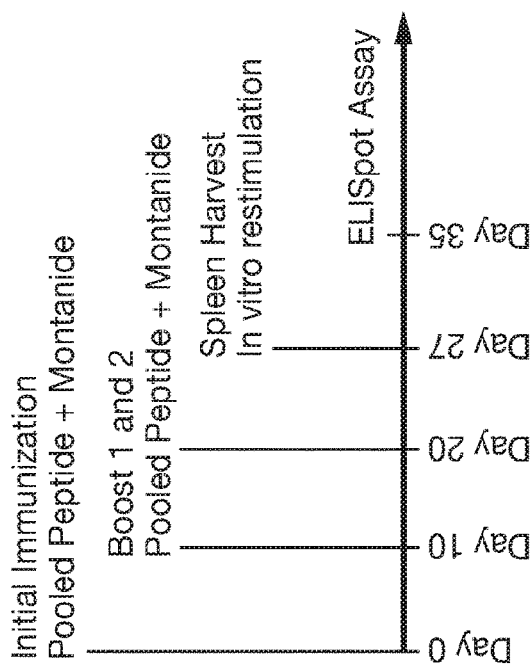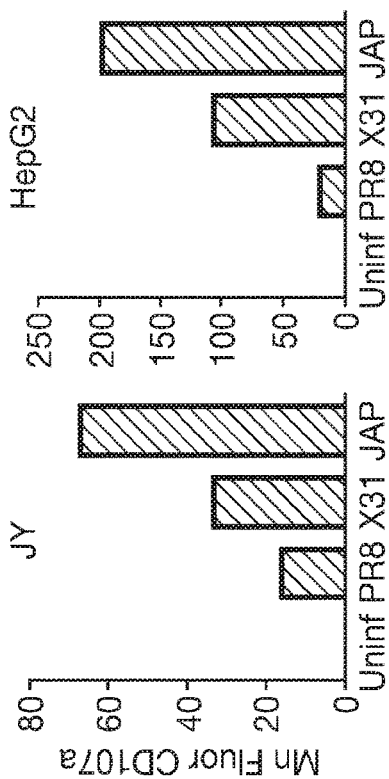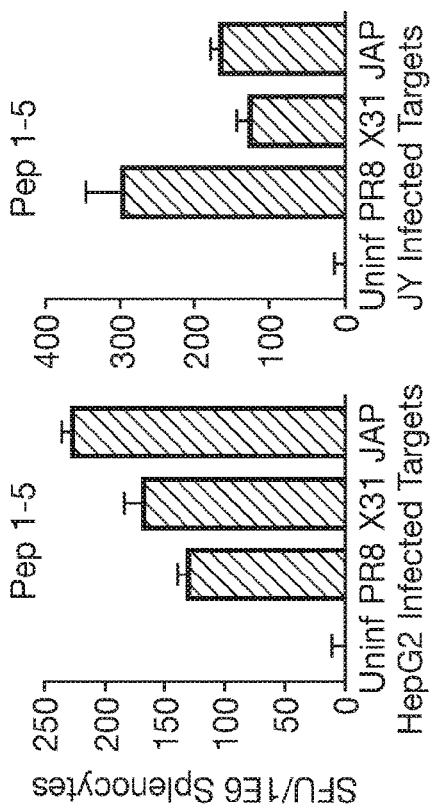

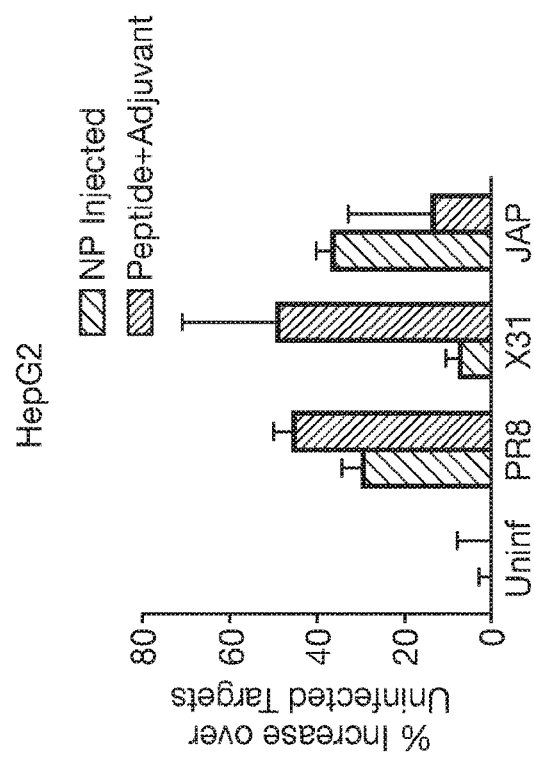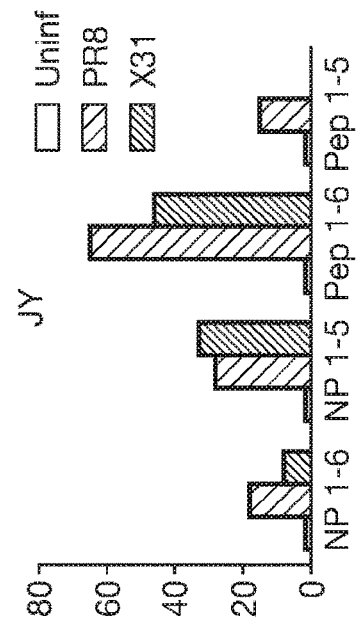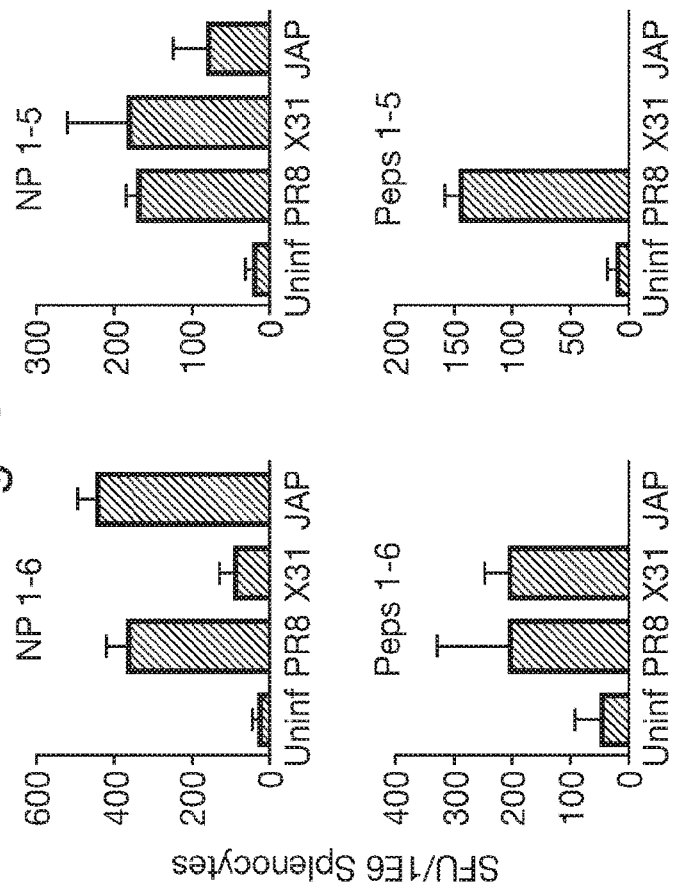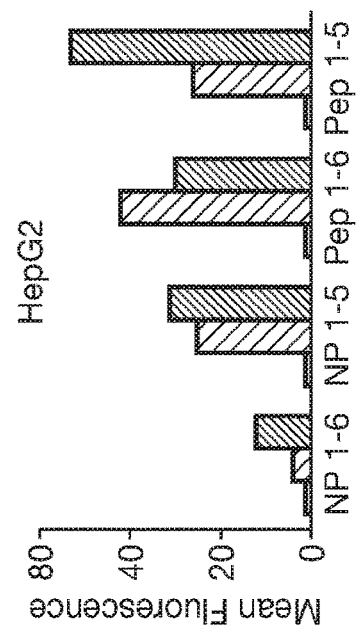
Fig. 5A
Fig. 5B
Fig. 5C

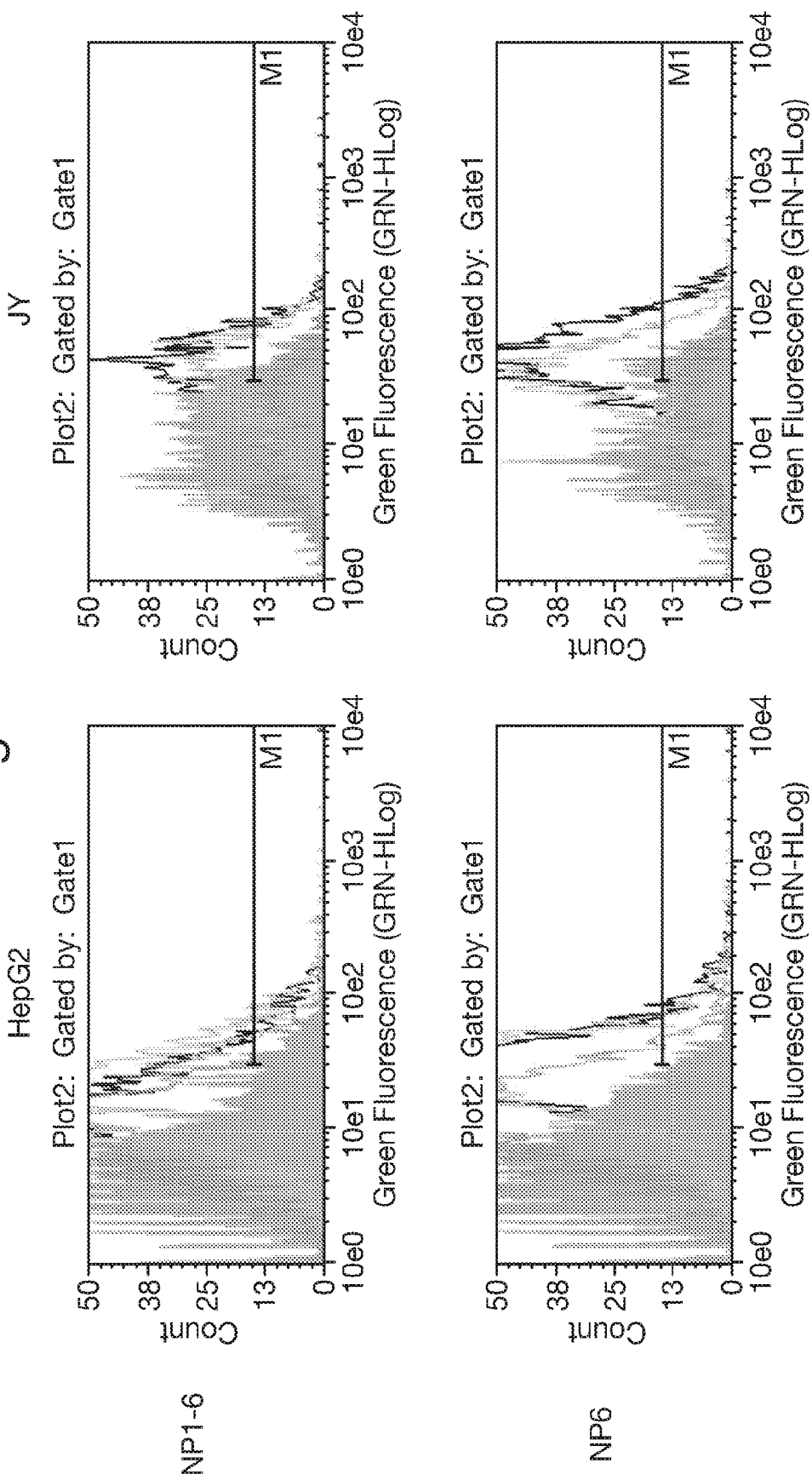

Fig. 12
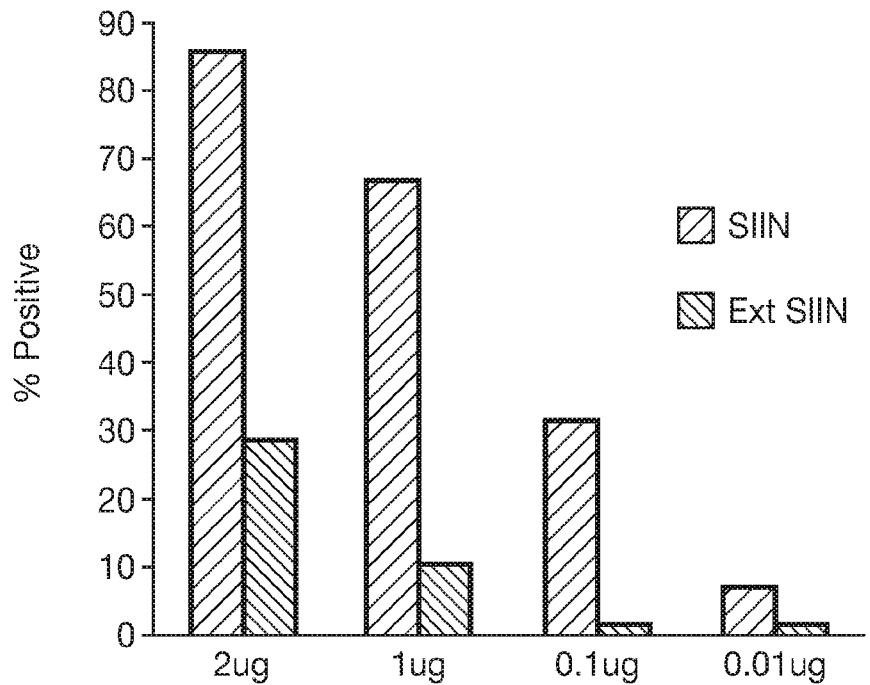
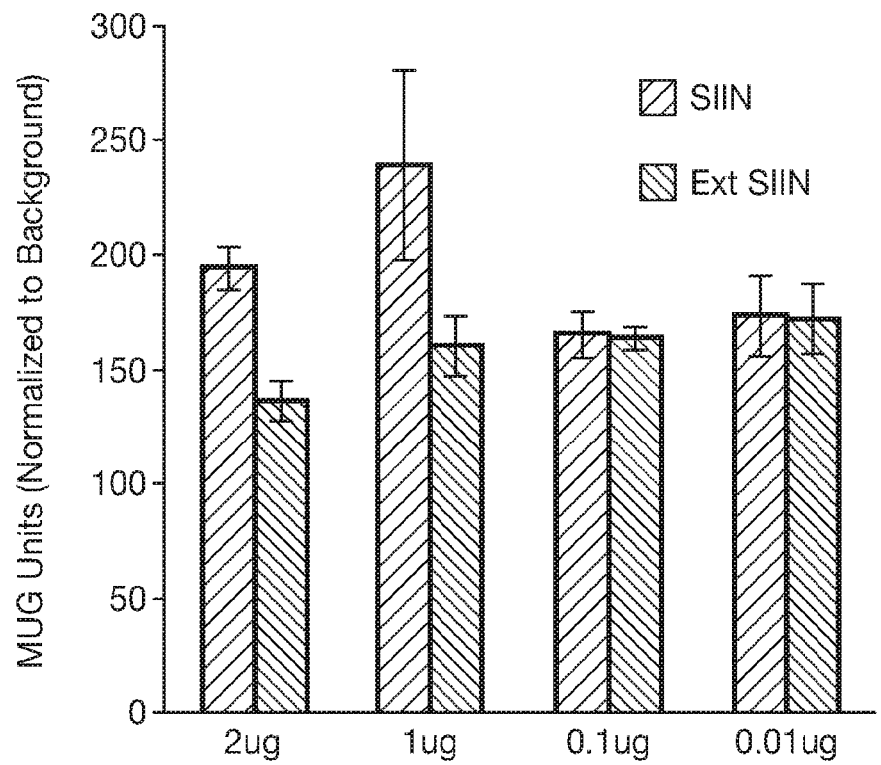

UNIVERSAL INFLUENZA VACCINE COMPOSITIONS

CROSS-REFERENCE TO RELATED APPLICATIONS

This application is a national phase application under 35 U.S.C. § 371 that claims priority to International Application No. PCT/GB2018/050004 filed Jan. 3, 2018, which claims priority to U.S. Provisional Application No. 62/441,659 filed Jan. 3, 2017, all of which are incorporated herein by reference in their entirety.

FIELD OF THE INVENTION

The invention relates to vaccine compositions comprising influenza peptides, and the use of such compositions for the treatment and prevention of influenza virus infection.

BACKGROUND TO THE INVENTION

Influenza is a significant global health problem, infecting up to 20% of the world's population annually, causing up to 5 million cases of severe illness and >300,000 deaths worldwide. In the U.S. alone, an estimated >30,000 deaths and nearly 300,000 hospitalizations are attributed to influenza infection each year. With the recent appearance of new, severe and potentially recurrent seasonal disease, widespread vaccination campaigns that reduce the incidence of influenza-induced pneumonia are being encouraged by the World Health Organization. Effectively reducing the incidence of influenza will require continued intense surveillance, increased use of currently available influenza vaccines, and availability of alternative vaccines and antiviral medications that can provide broader protection against shift-and-drift strains of influenza. Successful influenza vaccination campaigns can have enormous societal and economic impact.

The immune response to influenza is governed by both innate and adaptive immunity. The innate immune response to influenza limits initial viral replication but is relatively non-specific. Efficient clearance of influenza virus requires a robust adaptive immune response, activating both humoral and cell mediated immunity. Humoral immunity as mediated by secretory IgA and IgM antibodies provides protection against the establishment of initial infection, while IgG antibodies neutralize newly replicating virus in established infection.

Conventional influenza vaccines aim to induce humoral immunity to influenza virus. However, these vaccines are not completely protective due to occurrence of antigenic variations. In addition, it is thought that T-cell responses may have a key role in protecting against influenza. CD4+ T cells play a critical role in isotype-switching to IgG and in the generation of higher affinity antibodies and CTL memory. In humans, hemagglutinin (HA)-specific CD4+ T cells proliferate following influenza vaccination and aid the development of heterosubtypic influenza antibody responses. CD8+ cytotoxic T lymphocytes (CTLs) mediate viral clearance and have been shown to have cross-reactive responses to different subtypes of influenza A virus. This may explain the relative paucity of disease among individuals that are older, have been vaccinated against influenza, or have been previously exposed to influenza.

Influenza vaccines currently on the market are updated yearly. Their design is based on annual WHO strain recommendations, and they are manufactured prior to the beginning of an influenza season or pandemic. Current vaccines for influenza induce a protective humoral immune response against the HA and neuraminidase (NA) glycoproteins on the virion surface. However, viral HA and NA glycoproteins are highly susceptible to frequent and unpredictable antigenic shift and less frequent, but more severe, drift mutations, which result in loss of antibody recognition. This necessitates the frequent development of new vaccines to match the current viral serotype(s) infecting the human population. Accordingly, existing influenza vaccines are costly to produce and are unlikely to be protective against novel strains that emerge mid-season (e.g. 2009 H1N1 swine flu, H5N1, H7N9). Moreover, these vaccines are designed to provide antibody-based protection, with little consideration given to the induction of the T cell responses that are important for eliminating virus-infected cells from the body.

Several quadrivalent vaccines (protecting against two influenza A and two influenza B viruses) have been approved by the FDA. While these vaccines provide broader protection than conventional influenza vaccines, they are still unlikely to be protective against novel strains that emerge mid-season and are costly to produce. Furthermore, like conventional influenza vaccines, the quadrivalent vaccines are not designed to elicit T cell responses that are important for eliminating virus-infected cells from the body.

A "universal" influenza vaccine providing broad protection against all seasonal influenza strains and pandemic strains for years, if not a whole lifetime, is therefore desirable. Development of an effective universal influenza vaccine would lessen fears of future influenza pandemics and would be more cost-effective than developing and manufacturing annual seasonal influenza vaccines as is the current practice.

Several universal vaccine formulations are under development. These universal vaccines can be broadly characterized by the type of protective immune response that they stimulate: 1) B cell responses (antibody), 2) T cell responses, or 3) both B and T cell responses. Kanekiyo et al. generated HA nanoparticles (HA fused to ferritin) that induce high titre antibody responses that provide coverage against multiple influenza strains. This vaccine has yet to enter into clinical trials. A T cell based vaccine that targets four relatively conserved epitopes in the viral genome is also under development. A T cell vaccine based on highly conserved CD4 epitopes has been evaluated in a phase II challenge study with positive protective responses against various influenza strains including pandemic strains. A recombinant polyepitope vaccine, called Multimeric-001, that incorporates B cell, CD4 T cell-, and CD8 T cell conserved epitopes from nine different influenza proteins is being tested in early stage clinical trials. A fusion protein vaccine consisting of nucleoprotein (NP) and the B cell epitope M2e linked to an adjuvant and M2e peptide in gold nanoparticle in combination with CpG are also under development. Most of the above mentioned vaccines are formulated with various adjuvants that often induce adverse reactions when used in the clinic.

SUMMARY OF THE INVENTION

The present invention relates to an influenza vaccine composition that stimulates an immune response while avoiding the adverse clinical effects often associated with adjuvant-containing vaccines. In one aspect, the vaccine composition stimulates both the production of antibodies specific for influenza virus and a T cell response against influenza virus. Stimulation of both humoral and cellular responses allows the vaccine to mimic the immune response to natural viral infection (FIG. 1). The vaccine composition may provide protection against both seasonal and pandemic influenza strains, e.g. the vaccine composition may be a universal vaccine.

The present inventors have surprisingly identified that a nanoparticle, for example a gold nanoparticle, may be used to induce an efficient response to a vaccine composition designed to stimulate both the production of antibodies specific for influenza virus and a T cell response against influenza virus. Use of a nanoparticle abrogates the need to include a traditional adjuvant in the vaccine composition. Therefore, the likelihood of an individual experiencing an adverse reaction following administration of the vaccine composition is reduced.

The present inventors have also identified number of conserved peptides that are conserved between different influenza viruses and are presented by MHC molecules on cells infected with those viruses. Inclusion of such conserved peptides in the vaccine composition may confer protective capability against both seasonal and pandemic influenza strains. Including in the vaccine composition multiple conserved peptides that bind to different HLA supertypes results in a vaccine that is effective in individuals having different HLA types.

Accordingly, the present invention provides a vaccine composition comprising one or more immunogenic influenza virus peptides attached to a nanoparticle.

The present invention further provides:
- a vaccine composition comprising an influenza virus peptide comprising a CD8+ T cell epitope and an influenza virus peptide comprising a B cell epitope, wherein each peptide is attached to a nanoparticle;
- a vaccine composition comprising an influenza virus peptide comprising one or more of the CD8+ T cell epitopes set out in SEQ ID NOs: 1 to 18, wherein the peptide is attached to a nanoparticle;
- a method of preventing or treating an influenza virus infection, comprising administering the vaccine composition of the invention to an individual infected with, or at risk of being infected with, an influenza virus; and
- the vaccine composition of the invention for use in a method of preventing or treating an influenza virus infection in an individual.

BRIEF DESCRIPTION OF THE FIGURES

FIG. 4: Epitopes (P1-P5) specific CTLs generated in vivo in HLA A2 transgenic mice recognize both peptide loaded (panel B) and various influenza virus infected (panel C) target cells.

FIG. 5: Epitopes incorporated in NPs (NP 1-5) activates various influenza virus specific CTLs in HLA A2 transgenic mice. Panel A&B: ELISpot; Panel C: CD107 expression.

FIG. 8: Anti-M2e mediated infection neutralization. Serum used in the top panels is isolated from peptide immunized mice, bottom panels from NP immunized mice.

FIG. 12: CD8 epitopes nested within longer peptides are processed and presented on APCs. Top panel, SIIN:Kb complexes detected by flow cytometry. Bottom panel, SIIN specific T cell activation in a hybridoma assay.

DETAILED DESCRIPTION OF THE INVENTION

Figure 1:
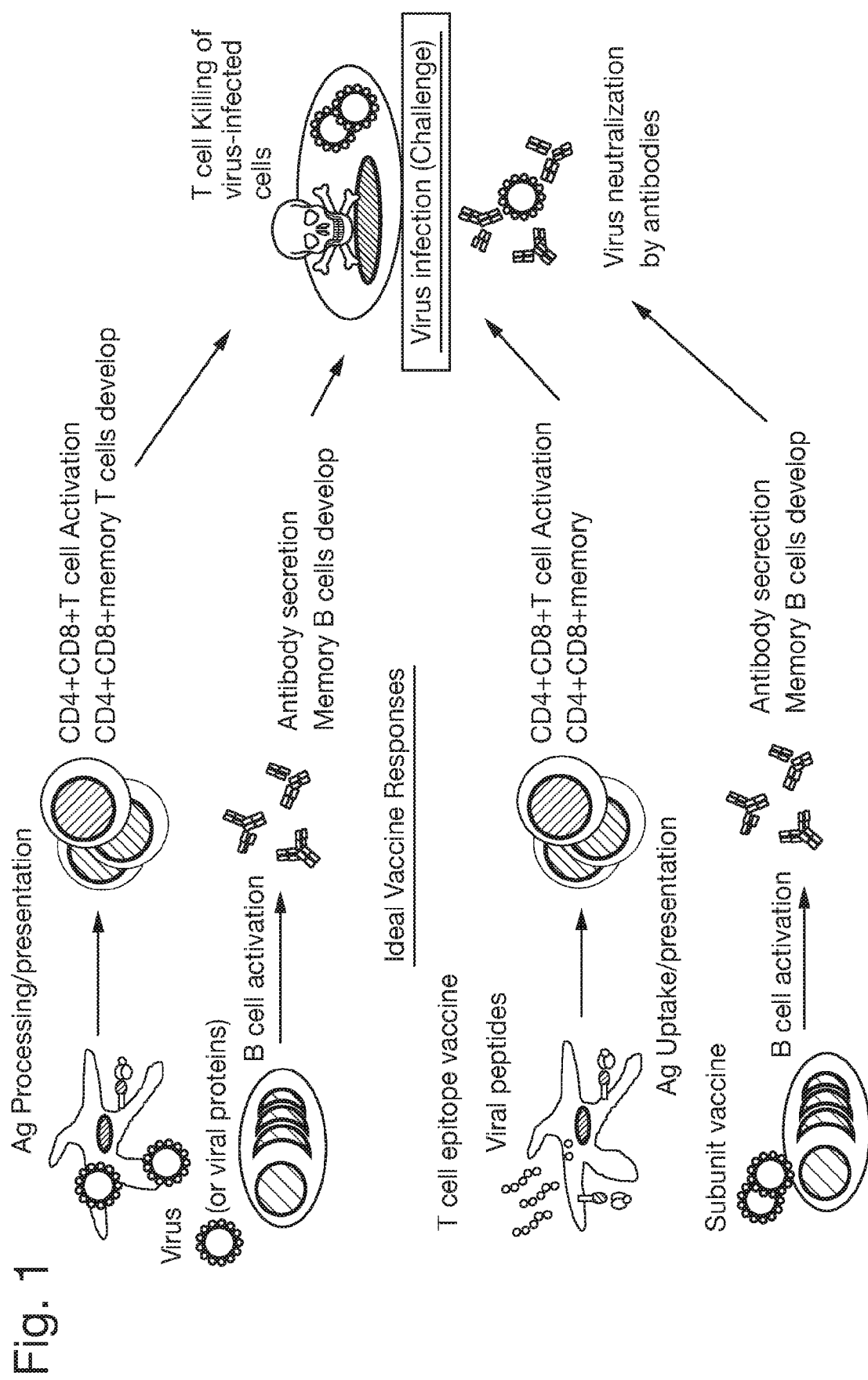
FIG. 1: Vaccine to mimic adaptive immune response generated by viral infection.

Vaccine Compositions Stimulating Humoral and Cellular Responses

The present invention provides a vaccine composition comprising one or more immunogenic influenza virus peptides attached to a nanoparticle. In particular, a vaccine composition comprising an influenza virus peptide comprising a CD8+ T cell epitope and an influenza virus peptide comprising a B cell epitope, wherein each peptide is attached to a nanoparticle.

This vaccine composition has a number of advantageous over conventional influenza vaccines known in the art. The key advantages are summarised here. However, further advantages will become apparent from the discussion below.

Firstly, the vaccine composition of the invention advantageously comprises an influenza virus peptide comprising a CD8+ T cell epitope and an influenza virus peptide comprising a B cell epitope. The vaccine composition is therefore capable of stimulating both cellular and humoral immune responses against an influenza virus. As described above, humoral immune responses provide a first line of defence against influenza virus infection. In particular, secretory IgA and IgM antibodies protect against the establishment of initial influenza virus infection, for instance by prevent virus from attaching to epithelial cells at mucosal surfaces. Later, during established infection, IgG antibodies neutralize newly replicating virus to help minimise viral reproduction. Humoral responses therefore have an important role in the prevention and treatment of influenza virus infection. However, cellular responses, particularly T cell responses, are also important. CD4+ T cells control isotype-switching to IgG and, therefore, the neutralisation of replicating virus. CD4+ T cells also contribute to the generation of higher affinity antibodies and to cytotoxic T lymphocyte (CTL) memory. CD8+ CTLs themselves mediate viral clearance via their cytotoxic activity against infected cells. Stimulating both humoral and cellular immunity therefore provides a beneficial double-pronged attack against influenza virus infection.

Secondly, each influenza virus peptide in the vaccine composition is attached to a nanoparticle, for example a gold nanoparticle. As described in more detail below, attachment to a nanoparticle reduces or eliminates the need to include an adjuvant in the vaccine composition. Thus, the vaccine composition is less likely to cause adverse clinical effects upon administration to an individual.

Influenza Virus Peptides

The vaccine composition of the invention comprises one or more immunogenic influenza virus peptides. The vaccine composition may comprise from about one to about 50 influenza virus peptides, such as about 2 to 40, 30 to 30, 4 to 25, 5 to 20, 6 to 15, 7, 8, 9 or 10 influenza virus peptides. The peptides each comprise one or more epitope, which may be a CD8+ T cell epitope, a CD4+ T cell epitope and/or a B cell epitope.

In one aspect, the vaccine composition comprises an influenza virus peptide comprising a CD8+ T cell epitope and an influenza virus peptide comprising a B cell epitope.

An influenza virus peptide is a peptide that is expressed by one or more influenza viruses. Influenza viruses are well known members of the Orthomyxovirdae family. Hundreds of strains of influenza virus exist which may be classified in three main categories, Influenza A, Influenza B or Influenza C, based on the HA and NA proteins they express. The vaccine composition may comprise influenza virus peptides from multiple strains of influenza, such as 1 to 2000, 100 to 1900, 200 to 1800, 300 to 1700, 400 to 1600, 500 to 1500, 600 to 1400, 700 to 1300, 800 to 1200 or 900 to 1100 strains of influenza. For example, the vaccine composition may comprise one more influenza virus peptide from Influenza A, Influenza B and/or Influenza C. Thus, the influenza virus peptide comprising a CD8+ T cell epitope comprised may be a peptide that is expressed by Influenza A, Influenza B and/or Influenza C virus. The influenza virus peptide comprising a B cell epitope may be a peptide that is expressed by Influenza A, Influenza B and/or Influenza C virus. The influenza virus peptide comprising a CD8+ T cell epitope and the influenza virus peptide comprising a B cell epitope may be peptides that are expressed by the same influenza strain, such as Influenza A, Influenza B or Influenza C. Alternatively, the influenza virus peptide comprising a CD8+ T cell epitope and the influenza virus peptide comprising a B cell epitope may be peptides that are expressed by different influenza strains.

If the influenza virus peptide is a peptide that is expressed by Influenza A virus, the Influenza A virus may be, for example, H1N1, H5N1, H7H9 or H3N2. Preferably, the influenza virus peptide is expressed by two or more of H1N1, H5N1, H7H9 and H3N2 Influenza A virus, such as, for example, H1N1 and H3N2. The influenza virus peptide may be a peptide that is expressed by a human influenza virus, a swine influenza virus, and/or an avian influenza virus. The influenza virus may be a pandemic influenza virus or a potentially pandemic influenza virus. The influenza virus may be a zoonotic influenza virus.

The influenza virus peptide may be a peptide that is expressed on the surface of one or more influenza viruses, or intracellularly within one or more influenza viruses. The peptide may be a structural peptide or a functional peptide, such as a peptide involved in the metabolism or replication of the influenza virus. Preferably, the peptide is an internal peptide. Preferably, the peptide is conserved between two or more different influenza strains.

The influenza virus peptide may contain any number of amino acids, i.e. be of any length. Typically, the influenza virus peptide is about 8 to about 30, 35 or 40 amino acids in length, such as about 9 to about 29, about 10 to about 28, about 11 to about 27, about 12 to about 26, about 13 to about 25, about 13 to about 24, about 14 to about 23, about 15 to about 22, about 16 to about 21, about 17 to about 20, or about 18 to about 29 amino acids in length.

The influenza virus peptide may be chemically derived from a polypeptide influenza virus antigen, for example by proteolytic cleavage. More typically, the influenza virus peptide may be synthesised using methods well known in the art.

The term "peptide" includes not only molecules in which amino acid residues are joined by peptide (—CO—NH—) linkages but also molecules in which the peptide bond is reversed. Such retro-inverso peptidomimetics may be made using methods known in the art, for example such as those described in Meziere et al (1997) J. Immunol. 159, 3230-3237. This approach involves making pseudopeptides containing changes involving the backbone, and not the orientation of side chains. Meziere et al (1997) show that, at least for MHC class II and T helper cell responses, these pseudopeptides are useful. Retro-inverse peptides, which contain NH—CO bonds instead of CO—NH peptide bonds, are much more resistant to proteolysis.

Similarly, the peptide bond may be dispensed with altogether provided that an appropriate linker moiety which retains the spacing between the carbon atoms of the amino acid residues is used; it is particularly preferred if the linker moiety has substantially the same charge distribution and substantially the same planarity as a peptide bond. It will also be appreciated that the peptide may conveniently be blocked at its N- or C-terminus so as to help reduce susceptibility to exoproteolytic digestion. For example, the N-terminal amino group of the peptides may be protected by reacting with a carboxylic acid and the C-terminal carboxyl group of the peptide may be protected by reacting with an amine. Other examples of modifications include glycosylation and phosphorylation. Another potential modification is that hydrogens on the side chain amines of R or K may be replaced with methylene groups (—NH2 may be modified to —NH(Me) or —N(Me)$_2$).

The term "peptide" also includes peptide variants that increase or decrease the half-life of the peptide in vivo. Examples of analogues capable of increasing the half-life of peptides used according to the invention include peptoid analogues of the peptides, D-amino acid derivatives of the peptides, and peptide-peptoid hybrids. A further embodiment of the variant polypeptides used according to the invention comprises D-amino acid forms of the polypeptide. The preparation of polypeptides using D-amino acids rather than L-amino acids greatly decreases any unwanted breakdown of such an agent by normal metabolic processes, decreasing the amounts of agent which needs to be administered, along with the frequency of its administration.

CD8+ T Cell Epitopes

The vaccine composition of the invention preferably comprises an influenza virus peptide comprising a CD8+ T cell epitope. A CD8+ T cell epitope is a peptide that is capable of (i) presentation by a class I MHC molecule and (ii) recognition by a T cell receptor (TCR) present on a CD8+ T cell. Preferably, recognition by the TCR results in activation of the CD8+ T cell. CD8+ T cell activation may lead to increased proliferation, cytokine production and/or cyotoxic effects.

Typically, the CD8+ T cell epitope is around 9 amino acids in length. The CD8+ T cell epitope may though be shorter or longer. For example, the CD8+ T cell epitope may be about 8, 9, 10, 11, 12, 13, 14 or 15 amino acids in length. The CD8+ T cell epitope may be about 8 to 15, 9 to 14 or 10 to 12 amino acids in length.

Influenza virus peptides comprising a CD8+ T cell epitope are known in the art. Methods for identifying CD8+ T cell epitopes are known in the art. Epitope mapping methods include X-ray co-crystallography, array-based oligo-peptide scanning (sometimes called overlapping peptide scan or pepscan analysis), site-directed mutagenesis, high throughput mutagenesis mapping, hydrogen-deuterium exchange, crosslinking coupled mass spectrometry, phage display and limited proteolysis. MHC motif prediction methodologies may also be used.

Preferably, CD8+ T cell epitopes presented by influenza virus-infected cells can be identified in order to directly identify CD8+ T cell epitopes for inclusion in the vaccine composition. This is an efficient and logical method which can be used alone or to confirm the utility of potential CD8+ T cell epitopes identified by MHC motif prediction methodologies. To perform the method, cells are infected with influenza virus and maintained in culture for a period of around 24 hours. The cells are then harvested and washed. Next, the cells are lysed and MHC/peptide complexes isolated by immunoaffinity chromatography using MHC molecule specific antibodies. The peptides purified from the MHC molecules are fractionated, for example using a C-18 reversed phase (RP) column using an offline HPLC. The peptide-containing fractions are collected, dried under a vacuum, and analysed by mass spectrometry to identify the sequences of the fractions. The acquired spectral data is then searched against all databased influenza proteins to identify peptide sequences associated with influenza virus. Synthetic peptides may then be made according to the identified sequences and subjected to mass spectrometry to confirm their identity to the peptides in the peptide-containing fractions.

In this method, any type of cells may be infected with influenza virus. The cells may be antigen presenting cells. The cells may be hepatoma cells such as HepG2 cells, EBV-transformed lymphoblastoid B cells such as JY cells, or lymphoblasts such as T2 cells.

Likewise, any influenza virus of interest may be used to infect the cells. For instance, the influenza virus may be an Influenza A, Influenza B or Influenza C virus. The Influenza A virus may, for example, be H1N1, H5N1, H7H9 or H3N2.

The direct identification of CD8+ T cell epitopes presented by influenza virus-infected cells is advantageous compared to MHC motif prediction methodologies. The immune epitope database (IEDB; http://www.iedb.org) is generated by motif prediction methods, and not functional methods, and contains several hundreds of predicted HLA-specific influenza T cell epitopes, including a number of shared epitopes with high MHC binding scores and limited CTL characterization. As both dominant and subdominant epitopes are presented by influenza virus-infected cells, it is difficult to sort out the dominance hierarchies of naturally presented epitopes using the database. Thus, it is not clear from the immune epitope database alone which of the listed epitopes may be expected to efficiently induce a CD8+ T cell response when included in a vaccine composition. The direct identification method set out above provides a mechanism for confirming the utility of the epitopes.

Furthermore, the direct identification method may be used to identify conserved CD8+ T cell epitopes presented by cells infected by different influenza viruses. In this way, CD8+ T cell epitopes suitable for inclusion in a universal vaccine may be identified. As set out in the Examples, the present inventors used the direct identification method to identify CD8+ T cell epitopes conserved between Influenza A (H1N1 and H3N2) and Influenza B strains. The sequences identified are set out in Table 1.

TABLE 1

| SEQ ID NO: | Peptide | Protein | HLA motif |
|---|---|---|---|
| 1 | PVAGGTSSIYI (P2) | polymerase PB2 | A2 |
| 2 | TVIKTNMI (P3) | polymerase PB1 | A2/ A24 |
| 3 | MTIIFLILM (P4) | hemagglutinin | A2/ A24 |
| 4 | ITFHGAKEI | Matrix protein 1 | A2/ A24 |
| 5 | AINGITNKV | Hemagglutinin | A2/ A24 |
| 6 | EEMGITTHF | RNA-directed RNA polymerase catalytic subunit | B44 |
| 7 | VETPIRNEW | Matrix protein 2 | B44 |
| 8 | REILTKTTV | Polymerase basic protein 2 | B44 |
| 9 | KESDEALNMTMASTP | Non-structural protein NS1 | B44 |
| 10 | LENERTLDF | Polymerase acidic protein | B44 |
| 11 | MEAVPLITI | Hemagglutinin | B44 |
| 12 | VEQEIRTF | Nuclear export protein | B44 |
| 13 | VEQELRTF | nonstructural protein 2 | B44 |
| 14 | SPDDFALIVNA | polymerase PB1 | B7 |
| 15 | YPDTGKVM | Neuraminidase | B7 |
| 16 | YPDASKVM | neuraminidase | B7 |
| 17 | QPETCNQSII | Neuraminidase | B7 |
| 18 | VPESKRMSL | nonstructural protein (NS1) | B7 |

The inventors also confirmed that the known peptides YINTALLNA (P1; SEQ ID NO: 19), AIMDKNIIL (P5; SEQ ID NO: 20) and LPFDRTTIM (SEQ ID NO: 21) are CD8+ T cell epitopes conserved between Influenza A (H1N1 and H3N2) and Influenza B strains.

The influenza virus peptide comprising a CD8+ T cell epitope may therefore comprise one or more of SEQ ID NOs: 1 to 21. For instance, the influenza virus peptide comprising a CD8+ T cell epitope may comprise two or more, three or more, four or more, five or more, ten or more, fifteen or more, or twenty or more of SEQ ID NOs: 1 to 21 in any combination. The influenza virus peptide comprising a CD8+ T cell epitope may comprise all of SEQ ID NOs: 1 to 21.

Similarly, the vaccine composition may comprise one or more influenza virus peptides each comprising a CD8+ T cell epitope comprising a different sequence selected from SEQ ID NOs: 1 to 21. For instance, the vaccine composition may comprise two or more, three or more, four or more, five or more, ten or more, fifteen or more, or twenty or more influenza virus peptides each comprising a CD8+ T cell epitope comprising a different sequence selected from SEQ ID NOs: 1 to 21, in any combination. The vaccine composition may, for example, comprise 21 influenza virus peptides each comprising a CD8+ T cell epitope comprising a different sequence selected from SEQ ID NOs: 1 to 21.

B Cell Epitopes

The vaccine composition of the invention may comprise an influenza virus peptide comprising a B cell epitope. A B cell epitope is a peptide that is capable of recognition by a B cell receptor (BCR) present on a B cell. Preferably, recognition by the BCR results in activation and/or maturation of the B cell. B cell activation may lead to increased proliferation, and/or antibody production.

Influenza virus peptides comprising a B cell epitope are known in the art. The B cell epitope may be a linear epitope, i.e. an epitope that is defined by the primary amino acid sequence of a particular region of an influenza virus protein. Alternatively, the epitope may be a conformational epitope, i.e. an epitope that is defined by the conformational structure of a native influenza protein. In this case, the epitope may be continuous (i.e. the components that interact with the antibody are situated next to each other sequentially on the protein) or discontinuous (i.e. the components that interact with the antibody are situated on disparate parts of the protein, which are brought close to each other in the folded native protein structure).

Typically, the B cell epitope is around 5 to 20 amino acids in length, such as 6 to 19, 7 to 18, 8 to 17, 9 to 16, 10 to 15, 11 to 14 or 12 to 13 amino acids in length.

Methods for identifying B cell epitopes are also known in the art. For instance, epitope mapping methods may be used to identify B cell epitopes. These methods include structural approaches, wherein the known or modelled structure of a protein is be used in an algorithm based approach to predict surface epitopes, and functional approaches, wherein the binding of whole proteins, protein fragments or peptides to an antibody can be quantitated e.g. using an Enzyme-Linked Immunosorbent Assay (ELISA). Competition mapping, antigen modification or protein fragmentation methods may also be used.

The B cell epitope may, for example, be an influenza matrix 2 protein (M2e) epitope. The extracellular domain of M2e protein is an evolutionarily conserved region in influenza A viruses. Thus, inclusion of an influenza peptide comprising a M2e B cell epitope in the vaccine composition may help to confer universal utility.

Universal Vaccine Compositions

The present invention also provides a vaccine composition comprising an influenza virus peptide comprising one or more of the CD8+ T cell epitopes set out in SEQ ID NOs: 1 to 21, wherein the peptide is attached to a nanoparticle.

The inclusion of an influenza virus peptide comprising one or more of the CD8+ T cell epitopes set out in SEQ ID NOs: 1 to 21 in the vaccine composition is advantageous. As set out above, the CD8+ T cell epitopes set out in SEQ ID NOs: 1 to 21 are conserved CD8+ T cell epitopes that are presented by MHC molecules on cells infected by different influenza viruses. Accordingly, an immune response generated by vaccination with a composition that comprises any of these epitopes should protect against subsequent infection with any influenza virus that shares that epitope. In other words, the vaccine composition has built-in cross-subtype efficacy, i.e. it is a universal influenza vaccine composition. Such a composition could prevent the significant spread of an emerging or re-emerging strain of influenza infection.

Furthermore, vaccine compositions based on epitopes presented by influenza virus-infected cells, such as the present vaccine composition, are superior to vaccines based on a viral protein subunit or a motif predicted epitope. Protein processing by the immune system is likely to alter native viral epitopes. Basing a vaccine composition on peptides demonstrated to be presented by infected cell removes this source of uncertainty, because the peptides have already undergone protein processing.

Attaching the influenza virus peptide to a nanoparticle, for example a gold nanoparticle, is also beneficial. As described in more detail below, attachment to a nanoparticle reduces or eliminates the need to include an adjuvant in the vaccine composition. Thus, the vaccine composition is less likely to cause adverse clinical effects upon administration to an individual.

Influenza Peptides Comprising SEQ ID NOs: 1 to 21

The vaccine composition comprises an influenza virus peptide comprising one or more of the CD8+ T cell epitopes set out in SEQ ID NOs: 1 to 21. Influenza virus peptides comprising SEQ ID NOs: 1 to 21 are described in detail above in relation to the vaccine compositions stimulating humoral and cellular responses. The influenza virus peptide may comprise two or more, such as three or more, four or more, five or more, ten or more, fifteen or more or 20 or more of the CD8+ T cell epitopes set out in SEQ ID NOs: 1 to 21. In this case, the influenza virus peptide may comprise any combination of the CD8+ T cell epitopes set out in SEQ ID NOs: 1 to 21. The influenza virus peptide may comprise all of the CD8+ T cell epitopes set out in SEQ ID NOs: 1 to 21.

The vaccine composition may comprise two or more influenza virus peptides each comprising a different CD8+ T cell epitope. Each of the two or more peptides may comprise a different CD8+ T cell epitope set out in SEQ ID NOs: 1 to 21. Alternatively, one or more of the two or more peptides may comprise a CD8+ T cell epitope that is not set out in SEQ ID NOs: 1 to 21. CD8+ T cell epitopes are known in the art.

Nanoparticles

In both the vaccine composition comprising an influenza virus peptide comprising a CD8+ T cell epitope and an influenza virus peptide comprising a B cell epitope, and the vaccine composition comprising an influenza virus peptide comprising one or more of the CD8+ T cell epitopes set out in SEQ ID NOs: 1 to 21, each of the influenza virus peptides is attached to a nanoparticle.

As set out above and demonstrated in the Examples below, attachment of the influenza virus peptides to a nanoparticle (such as a gold nanoparticle) reduces or eliminates the need to include an adjuvant in the vaccine composition. The nanoparticles may contain immune "danger signals" that help to effectively induce an immune response to the influenza virus peptides. The nanoparticles may induce dendritic cell (DC) activation and maturation, required for a robust immune response. The nanoparticles may contain non-self components that improve uptake of the nanoparticles and thus the influenza virus peptides by cells, such as antigen presenting cells. Attachment of an influenza virus peptide to a nanoparticle may therefore enhance the ability of antigen presenting cells to stimulate virus-specific B and/or T cells. Attachment to a nanoparticle also facilitates delivery of the vaccine compositions via the subcutaneous, intradermal, transdermal and oral/buccal routes, providing greater flexibility in administration that conventional influenza vaccines.

Nanoparticles are particles between 1 and 100 nanometers (nm) in size which can be used as a substrate for immobilising ligands. In the vaccine compositions of the invention, the nanoparticle may have a mean diameter of 1 to 100, 20 to 90, 30 to 80, 40 to 70 or 50 to 60 nm. Preferably, the nanoparticle has a mean diameter of 20 to 40 nm. A mean diameter of 20 to 40 nm facilitates uptake of the nanoparticle to the cytosol. The mean diameter can be measured using techniques well known in the art such as transmission electron microscopy.

Nanoparticles suitable for the delivery of antigen, such as an influenza virus peptide, are known in the art. Methods for the production of such nanoparticles are also known.

The nanoparticle may, for example, be a polymeric nanoparticle, an inorganic nanoparticle, a liposome, an immune stimulating complex (ISCOM), a virus-like particle (VLP), or a self-assembling protein. The nanoparticle is preferably a calcium phosphate nanoparticle, a silicon nanoparticle or a gold nanoparticle.

The nanoparticle may be a polymeric nanoparticle. The polymeric nanoparticle may comprise one or more synthetic polymers, such as poly(d,l-lactide-co-glycolide) (PLG), poly(d,l-lactic-coglycolic acid) (PLGA), poly(g-glutamic acid) (g-PGA)m poly(ethylene glycol) (PEG), or polystyrene. The polymeric nanoparticle may comprise one or more natural polymers such as a polysaccharide, for example pullulan, alginate, inulin, and chitosan. The use of a polymeric nanoparticle may be advantageous due to the properties of the polymers that may be include in the nanoparticle. For instance, the natural and synthetic polymers recited above may have good biocompatibility and biodegradability, a non-toxic nature and/or the ability to be manipulated into desired shapes and sizes. The polymeric nanoparticle may form a hydrogel nanoparticle. Hydrogel nanoparticles are a type of nano-sized hydrophilic three-dimensional polymer network. Hydrogel nanoparticles have favourable properties including flexible mesh size, large surface area for multivalent conjugation, high water content, and high loading capacity for antigens. Polymers such as Poly(L-lactic acid) (PLA), PLGA, PEG, and polysaccharides are particularly suitable for forming hydrogel nanoparticles.

The nanoparticle may be an inorganic nanoparticle. Typically, inorganic nanoparticles have a rigid structure and are non-biodegradable. However, the inorganic nanoparticle may be biodegradable. The inorganic nanoparticle may comprise a shell in which an antigen may be encapsulated. The inorganic nanoparticle may comprise a core to which an antigen may be covalently attached. The core may comprise a metal. For example, the core may comprise gold (Au), silver (Ag) or copper (Cu) atoms. The core may be formed of more than one type of atom. For instance, the core may comprise an alloy, such as an alloy of Au/Ag, Au/Cu, Au/Ag/Cu, Au/Pt, Au/Pd or Au/Ag/Cu/Pd. The core may comprise calcium phosphate (CaP). The core may comprise a semiconductor material, for example cadmium selenide.

Other exemplary inorganic nanoparticles include carbon nanoparticles and silica-based nanoparticles. Carbon nanoparticles are have good biocompatibility and can be synthesized into nanotubes and mesoporous spheres. Silica-based nanoparticles (SiNPs) are biocompatible and can be prepared with tunable structural parameters to suit their therapeutic application.

The nanoparticle may be a silicon nanoparticle, such as an elemental silicon nanoparticle. The nanoparticle may be mesoporous or have a honeycomb pore structure. Preferably, the nanoparticle is an elemental silicon particle having a honeycomb pore structure. Such nanoparticles are known in the art and offer tunable and controlled drug loading, targeting and release that can be tailored to almost any load, route of administration, target or release profile. For example, such nanoparticles may increase the bioavailability of their load, and/or improve the intestinal permeability and absorption of orally administered actives. The nanoparticles may have an exceptionally high loading capacity due to their porous structure and large surface area. The nanoparticles may release their load over days, weeks or months, depending on their physical properties. Since silicon is a naturally occurring element of the human body, the nanoparticles may elicit no response from the immune system. This is advantageous to the in vivo safety of the nanoparticles.

Any of the SiNPs described above may be biodegradable or non-biodegradable. A biodegradable SiNP may dissolve to orthosilic acid, the bioavailable form of silicon. Orthosilic acid has been shown to be beneficial for the health of bones, connective tissue, hair, and skin.

The nanoparticle may be a liposome. Liposomes are typically formed from biodegradable, non-toxic phospholipids and comprise a self-assembling phospholipid bilayer shell with an aqueous core. A liposome may be an unilameller vesicle comprising a single phospholipid bilayer, or a multilameller vesicle that comprises several concentric phospholipid shells separated by layers of water. As a consequence, liposomes can be tailored to incorporate either hydrophilic molecules into the aqueous core or hydrophobic molecules within the phospholipid bilayers. Liposomes may encapsulate antigen within the core for delivery. Liposomes may incorporate viral envelope glycoproteins to the shell to form virosomes. A number of liposome-based products are established in the art and are approved for human use.

The nanoparticle may be an immune-stimulating complex (ISCOM). ISCOMs are cage-like particles which are typically formed from colloidal saponin-containing micelles. ISCOMs may comprise cholesterol, phospholipid (such as phosphatidylethanolamine or phosphatidylcholine) and saponin (such as Quil A from the tree Quillaia saponaria). ISCOMs have traditionally been used to entrap viral envelope proteins, such as envelope proteins from herpes simplex virus type 1, hepatitis B, or influenza virus.

The nanoparticle may be a virus-like particle (VLP). VLPs are self-assembling nanoparticles that lack infectious nucleic acid, which are formed by self-assembly of biocompatible capsid protein. VLPs are typically about 20 to about 150 nm, such as about 20 to about 40 nm, about 30 to about 140 nm, about 40 to about 130 nm, about 50 to about 120 nm, about 60 to about 110 nm, about 70 to about 100 nm, or about 80 to about 90 nm in diameter. VLPs advantageously harness the power of evolved viral structure, which is naturally optimized for interaction with the immune system. The naturally-optimized nanoparticle size and repetitive structural order means that VLPs induce potent immune responses, even in the absence of adjuvant.

The nanoparticle may be a self-assembling protein. For instance, the nanoparticle may comprise ferritin. Ferritin is a protein that can self-assemble into nearly-spherical 10 nm structures. The nanoparticle may comprise major vault protein (MVP). Ninety-six units of MVP can self-assemble into a barrel-shaped vault nanoparticle, with a size of approximately 40 nm wide and 70 nm long.

The nanoparticle may be a calcium phosphate (CaP) nanoparticle. CaP nanoparticles may comprise a core comprising one or more (such as two or more, 10 or more, 20 or more, 50 or more, 100 or more, 200 or more, or 500 or more) molecules of CaP. CaP nanoparticles and methods for their production are known in the art. For instance, a stable nano-suspension of CAP nanoparticles may be generated by mixing inorganic salt solutions of calcium and phosphates in pre-determined ratios under constant mixing.

The CaP nanoparticle may have an average particle size of about 80 to about 100 nm, such as about 82 to about 98 nm, about 84 to about 96 nm, about 86 to about 94 nm, or about 88 to about 92 nm. This particle size may produce a better performance in terms of immune cell uptake and immune response than other, larger particle sizes. The particle size may be stable (i.e. show no significant change), for instance when measured over a period of 1 month, 2 months, 3 months, 6 months, 12 months, 18 months, 24 months, 36 months or 48 months.

CaP nanoparticles can be co-formulated with one or multiple antigens either adsorbed on the surface of the nanoparticle or co-precipitated with CaP during particle synthesis. For example, a peptide, such as an influenza virus peptide, may be attached to the CaP nanoparticle by dissolving the peptide in DMSO (for example at a concentration of about 10 mg/ml), adding to a suspension of CaP nanoparticles together with N-acetyl-glucosamine (GlcNAc) (for example at 0.093 mol/L and ultra-pure water, and mixing at room temperature for a period of about 4 hours (for example, 1 hour, 2 hours, 3 hours, 5 hours, 6 hours, 7 hours, 8 hours, 9 hours or 10 hours).

The vaccine composition may comprise about 0.15 to about 0.8%, such as 0.2 to about 0.75%, 0.25 to about 0.7%, 0.3 to about 0.6%, 0.35 to about 0.65%, 0.4 to about 0.6%, or 0.45 to about 0.55%, CaP nanoparticles. Preferably the vaccine composition comprises about 0.3% CaP nanoparticles.

CaP nanoparticles have a high degree of biocompatibility due to their chemical similarity to human hard tissues such as bone and teeth. Advantageously, therefore, CaP nanoparticles are non-toxic when used for therapeutic applications. CaP nanoparticles are safe for administration via intramuscular, subcutaneous, oral, or inhalation routes. CaP nanoparticles are also simple to synthesise commercially. Furthermore, CaP nanoparticles may be associated with slow release of antigen, which may enhance the induction of an immune response to an influenza virus peptide attached to the nanoparticle. CaP nanoparticles may be used both as an adjuvant, and as a drug delivery vehicle.

The nanoparticle may be a gold nanoparticle. Gold nanoparticles are known in the art and are described in particular in WO 2002/32404, WO 2006/037979, WO 2007/122388, WO 2007/015105 and WO 2013/034726. The gold nanoparticle attached to each influenza virus peptide may be a gold nanoparticle described in any of WO 2002/32404, WO 2006/037979, WO 2007/122388, WO 2007/015105 and WO 2013/034726.

Gold nanoparticles comprise a core comprising a gold (Au) atom. The core may further comprise one or more Fe, Cu or Gd atoms. The core may be formed from a gold alloy, such as Au/Fe, Au/Cu, Au/Gd, Au/Fe/Cu, Au/Fe/Gd or Au/Fe/Cu/Gd. The total number of atoms in the core may be 100 to 500 atoms, such as 150 to 450, 200 to 400 or 250 to 350 atoms. The gold nanoparticle may have a mean diameter of 1 to 100, 20 to 90, 30 to 80, 40 to 70 or 50 to 60 nm. Preferably, the gold nanoparticle has a mean diameter of 20 to 40 nm.

One or more ligands other than the influenza virus peptides may be linked to the nanoparticle, which may be any of the types of nanoparticle described above. The ligands may form a "corona", a layer or coating which may partially or completely cover the surface of the core. The corona may be considered to be an organic layer that surrounds or partially surrounds the nanoparticle core. The corona may provide or participate in passivating the core of the nanoparticle. Thus, in certain cases the corona may be a sufficiently complete coating layer to stabilise the core. The corona may facilitate solubility, such as water solubility, of the nanoparticles of the present invention.

The nanoparticle may comprise at least 10, at least 20, at least 30, at least 40 or at least 50 ligands. The ligands may include one or more peptides, protein domains, nucleic acid molecules, lipidic groups, carbohydrate groups, anionic groups, or cationic groups, glycolipids and/or glycoproteins. The carbohydrate group may be a polysaccharide, an oligosaccharide or a monosaccharide group (e.g. glucose). One or more of the ligands may be a non-self component, that renders the nanoparticle more likely to be taken up by antigen presenting cells due to its similarity to a pathogenic component. For instance, one or more ligands may comprise a carbohydrate moiety (such as a bacterial carbohydrate moiety), a surfactant moiety and/or a glutathione moiety. Exemplary ligands include glucose, N-acetylglucosamine (GlcNAc), glutathione, 2'-thioethyl-β-D-glucopyranoside and 2'-thioethyl-D-glucopyranoside. Preferred ligands include glycoconjugates, which form glyconanoparticles Linkage of the ligands to the core may be facilitated by a linker. The linker may comprise a thiol group, an alkyl group, a glycol group or a peptide group. For instance, the linker may comprise C2-C15 alkyl and/or C2-C15 glycol. The linker may comprise a sulphur-containing group, amino-containing group, phosphate-containing group or oxygen-containing group that is capable of covalent attachment to the core. Alternatively, the ligands may be directly linked to the core, for example via a sulphur-containing group, amino-containing group, phosphate-containing group or oxygen-containing group comprised in the ligand.

Attachment to Nanoparticles

The influenza virus peptides may be attached at their N-terminus to the nanoparticle. Typically, the influenza virus peptides are attached to the core of the nanoparticle, but attachment to the corona or a ligand may also be possible.

One or more of the influenza virus peptides may be directly attached to the nanoparticle, for example by covalent bonding of an atom in a sulphur-containing group, amino-containing group, phosphate-containing group or oxygen-containing group in the peptide to an atom in the nanoparticle or its core.

A linker may be used to link one or more of the influenza virus peptides to the nanoparticle. The linker may comprise a sulphur-containing group, amino-containing group, phosphate-containing group or oxygen-containing group that is capable of covalent attachment to an atom in the core. For example, the linker may comprise a thiol group, an alkyl group, a glycol group or a peptide group.

The linker may comprise a peptide portion and a non-peptide portion. The peptide portion may comprise the sequence $X_1X_2Z_1$, wherein $X_1$ is an amino acid selected from A and G; $X_2$ is an amino acid selected from A and G; and $Z_1$ is an amino acid selected from Y and F. The peptide portion may comprise the sequence AAY or FLAAY. The peptide portion of the linker may be linked to the N-terminus of the influenza virus peptide. The non-peptide portion of the linker may comprise a C2-C15 alkyl and/a C2-C15 glycol, for example a thioethyl group or a thiopropyl group.

The linker may be (i) HS—$(CH_2)_2$—CONH-AAY; (ii) HS—$(CH_2)_2$—CONN-LAAY; (iii) HS—$(CH_2)_3$—CONH-AAY; (iv) HS—$(CH_2)_3$—CONH-FLAAY; (v) HS—$(CH_2)_{10}$—$(CH_2OCH_2)_7$—CONH-AAY; and (vi) HS—$(CH_2)_{10}$—$(CH_2OCH_2)_7$—CONN-FLAAY. In this case, the thiol group of the non-peptide portion of the linker links the linker to the core.

Other suitable linkers for attaching an influenza virus to a nanoparticle are known in the art, and may be readily identified and implemented by the skilled person.

When the vaccine composition comprises an influenza virus peptide comprising a CD8+ T cell epitope and a influenza virus peptide comprising a B cell epitope, each influenza virus peptide may be attached to a different nanoparticle. In this case, the nanoparticle to which each influenza virus peptide is attached may be the same type of nanoparticle. For instance, each influenza virus peptide may be attached to a gold nanoparticle. Each influenza virus peptide may be attached to a CaP nanoparticle. The nanoparticle to which each influenza virus peptide is attached may be a different type of nanoparticle. For instance, one influenza virus peptide may be attached to a gold nanoparticle, and the other influenza virus peptide may be attached to a CaP nanoparticle. Preferably though, the influenza virus peptide comprising a CD8+ T cell epitope and the influenza virus peptide comprising a B cell epitope are attached to the same nanoparticle. For example, the influenza virus peptide comprising a CD8+ T cell epitope and the influenza virus peptide comprising a B cell epitope may be attached to the same gold nanoparticle. This provides a single particle that is capable of stimulating both an influenza virus-specific cellular response, and an influenza virus-specific humoral response.

CD4+ T Cell Epitopes

A vaccine composition of the invention may further comprise an influenza virus peptide comprising a CD4+ T cell epitope. CD4+ T cell epitopes are defined above.

The vaccine composition may comprise two or more, such as three or more, four or more, five our more, ten or more, fifteen or more or twenty or more influenza virus peptides comprising a CD4+ T cell epitope. Such peptides are known in the art.

The influenza virus peptide comprising a CD4+ T cell epitope may be a different peptide from the influenza virus peptide encoding the CD8+ T cell and the influenza virus peptide encoding the B cell epitope. The influenza virus peptide comprising a CD4+ T cell epitope may be the same peptide as the influenza virus peptide encoding the CD8+ T cell. That is, the influenza virus peptide comprising a CD8+ T cell epitope may further comprise a CD4+ T cell epitope.

When the influenza virus peptide comprising a CD8+ T cell epitope comprises a CD4+ T cell epitope, the CD8+ epitope may be nested within the CD4+ T cell epitope. CD4+ T cell epitopes are typically longer than CD8+ T cell epitopes. Therefore, extending one or both termini of the CD8+ T cell epitope may yield a longer, CD4+ T cell epitope whose sequence still comprises the CD8+ T cell epitope. Therefore, the CD4+ T cell epitope may comprise a CD8+ T cell epitope, such as a CD8+ T cell epitope set out in SEQ ID NOs: 1 to 21, extended at its N-terminus or C-terminus. The CD8+ T cell epitope may be extended by 1, 2, 3, 4 or 5 amino acids at its N terminus. The CD8+ T cell epitope may be extended by 1, 2, 3, 4 or 5 amino acids at its C terminus. Preferably, the CD8+ T cell epitope is extended by 3 amino acids at the N terminus, and 3 amino acids at the C terminus. However, the CD8+ T cell epitope need not be extended by the same number of amino acids at each terminus.

The CD8+ T cell epitope nested within an extended peptides may be capable of generating a robust CTL response. The extended peptide (CD4+ T cell epitope) is capable of inducing T helper mediated cytokine responses. Thus, inclusion of an influenza virus peptide comprising a CD8+ T cell epitope and a CD4+ T cell epitope in the vaccine composition may allow the vaccine composition to induce both cytotoxic and helper T cell responses, providing improved anti-influenza immunity.

As set out in the Examples, the inventors have identified a number of potential CD4+ T cell epitopes in which a CD8+ T cell epitope set out in SEQ ID NOs: 1 to 21 is nested. These are set out in Table 2.

TABLE 2

| CD8 epitope | Extended epitope (potential CD4 epttope) | Protein | HLA motif |
|---|---|---|---|
| YINTALLNA (SEQ ID NO: 19) | kgvYINTALLNAsca (SEQ ID NO: 22) | polymerase PA | A2 |
| PVAGGTSSIYI (SEQ ID NO: 1) | rflPVAGGTSSIYIevl (SEQ ID NO: 23) | polymerase PB2 | A2 |
| TVIKTNMI (SEQ ID NO: 2) | igvTVIKTNMInnd (SEQ ID NO: 24) | polymerase PB1 | A2/A24 |
| AIMDKNIIL (SEQ ID NO: 20) | mdqAIMDKNIILkan (SEQ ID NO: 25) | nonstructural protein 1 | A2/A24 |
| ITFHGAKEI (SEQ ID NO: 4) | kreITFHGAKEIsls (SEQ ID NO: 26) | Matrix protein 1 | A2/A24 |
| AINGITNKV (SEQ ID NO: 5) | tqnAINGITNKVsnv (SEQ ID NO: 27) | Hemagglutinin | A2/A24 |

Thus, the influenza virus peptide comprising a CD8+ T cell epitope and a CD4+ T cell epitope may comprise one or more of the peptides set out in SEQ ID NOs: 22 to 27. The influenza virus peptide comprising a CD8+ T cell epitope and a CD4+ T cell epitope may comprise two or more, three or more, four or more or five or more of the peptides set out in SEQ ID NOs: 22 to 27, in any combination. The influenza virus peptide comprising a CD8+ T cell epitope and a CD4+ T cell epitope may comprise all of the peptides set out in SEQ ID NOs: 22 to 27

The influenza virus peptide comprising a CD4+ T cell epitope may be attached to a nanoparticle. The nanoparticle may be a gold nanoparticle. Nanoparticles and attachment thereto are described above.

Interaction with HLA Supertypes

The vaccine composition may comprise at least two influenza virus peptides comprising a CD8+ T cell epitope which each interacts with a different HLA supertype. Including a plurality of such peptides in the vaccine composition allows the vaccine composition to elicit a CD8+ T cell response in a greater proportion of individuals to which the vaccine composition is administered. This is because the vaccine composition should be capable of eliciting a CD8+ T cell response in all individuals of an HLA supertype that interacts with one of the CD8+ T cell epitopes comprised in the plurality of influenza virus peptides. Each CD8+ T cell epitope may interact with HLA-A1, HLA-A2, HLA-A3, HLA-A24, HLA-B7, HLA-B8, HLA-B27, HLA-B44, HLA-B58 or HLA-B62, or any other HLA supertype know in the art. Any combination of influenza virus peptides comprising such a CD8+ T cell epitope is possible.

The vaccine composition may comprise at least one immunogenic peptide that interacts with at least two different HLA supertypes. Again, this allows the vaccine composition to elicit a CD8+ T cell response in a greater proportion of individuals to which the vaccine composition is administered. The vaccine composition may comprise at least two, at least three, at least four, at least five, at least two, at least fifteen, or at least twenty immunogenic peptides that each interact with at least two different HLA subtypes. Each immunogenic peptide may interact with at least two, at least three, at least four, at least five, at least six, at least 7, at least 8, at least 9 or at least 10 different HLA supertypes. Each immunogenic peptide may interact with two or more of HLA-A1, HLA-A2, HLA-A3, HLA-A24, HLA-B7, HLA-B8, HLA-B27, HLA-B44, HLA-B58 or HLA-B62, or any other HLA supertype known in the art, in any combination. Preferably, the vaccine composition comprises an immunogenic peptide that interacts with HLA-A2 and HLA-24. In this case, the vaccine composition may, for example, comprise an influenza virus peptide comprising a CD8+ T cell epitope comprises one or more of the peptides set out in SEQ ID NOs: 3 to 5.

Medicaments, Methods and Therapeutic Use

The invention provides a method of preventing or treating an influenza virus infection, comprising administering the vaccine composition of the inventions to an individual infected with, or at risk of being infected with, an influenza virus. The invention also provides a vaccine composition of the invention for use in a method of preventing or treating an influenza virus infection in an individual.

The influenza virus may be an Influenza A, Influenza B and/or Influenza C virus. The Influenza A virus may, for example, be H1N1, H5N1, H7H9 or H3N2. The influenza virus may be a human influenza virus, a swine influenza virus, or an avian influenza virus. The influenza virus may be a pandemic influenza virus or a potentially pandemic influenza virus.

The vaccine composition may be provided as a pharmaceutical composition. The pharmaceutical composition preferably comprises a pharmaceutically acceptable carrier or diluent. The pharmaceutical composition may be formulated using any suitable method. Formulation of cells with standard pharmaceutically acceptable carriers and/or excipients may be carried out using routine methods in the pharmaceutical art. The exact nature of a formulation will depend upon several factors including the cells to be administered and the desired route of administration. Suitable types of formulation are fully described in Remington's Pharmaceutical Sciences, 19th Edition, Mack Publishing Company, Eastern Pennsylvania, USA.

The vaccine composition or pharmaceutical composition may be administered by any route. Suitable routes include, but are not limited to, the intravenous, intramuscular, intraperitoneal, subcutaneous, intradermal, transdermal and oral/buccal routes.

Compositions may be prepared together with a physiologically acceptable carrier or diluent. Typically, such compositions are prepared as liquid suspensions of peptide-linked nanoparticles. The nanoparticles may be mixed with an excipient which is pharmaceutically acceptable and compatible with the active ingredient. Suitable excipients are, for example, water, saline, dextrose, glycerol, of the like and combinations thereof.

In addition, if desired, the pharmaceutical compositions may contain minor amounts of auxiliary substances such as wetting or emulsifying agents, and/or pH buffering agents.

The peptide-linked nanoparticles are administered in a manner compatible with the dosage formulation and in such amount will be therapeutically effective. The quantity to be administered depends on the subject to be treated, the disease to be treated, and the capacity of the subject's immune system. Precise amounts of nanoparticles required to be administered may depend on the judgement of the practitioner and may be peculiar to each subject.

Any suitable number of nanoparticles may be administered to a subject. For example, at least, or about, $0.2 \times 10^6$, $0.25 \times 10^6$, $0.5 \times 10^6$, $1.5 \times 10^6$, $4.0 \times 10^6$ or $5.0 \times 10^6$ nanoparticles per kg of patient may administered. For example, at least, or about, $10^5$, $10^6$, $10^7$, $10^8$, $10^9$ cells may be administered. As a guide, the number of nanoparticles of the invention to be administered may be from $10^5$ to $10^9$, preferably from $10^6$ to $10^8$.

It is to be understood that different applications of the disclosed products and methods may be tailored to the specific needs in the art. It is also to be understood that the terminology used herein is for the purpose of describing particular embodiments of the invention only, and is not intended to be limiting.

In addition, as used in this specification and the appended claims, the singular forms "a", "an", and "the" include plural referents unless the content clearly dictates otherwise. Thus, for example, reference to "a CAR" includes "CARs", reference to "a T cell" includes two or more such T cells, reference to "a component" includes two or more such components, and the like.

All publications, patents and patent applications cited herein, whether supra or infra, are hereby incorporated by reference in their entirety.

FURTHER EMBODIMENTS OF THE INVENTION

1. An isolated oligopeptide or peptide in a pharmaceutical composition comprising at least one peptide having an amino acid sequence selected from the group consisting of SEQ ID NO: 1 to 18, said oligopeptide or peptide consisting of 8 to about 30 amino acid residues, wherein said oligopeptide or peptide binds to class I MHC molecules or can be processed to bind to class I MHC molecules and activate T lymphocyte response and wherein the oligopeptide or peptide is in the form of a pharmaceutically acceptable salt.
2. The oligopeptide of item 1 wherein said oligopeptide comprises at least two epitopic peptides.
3. The oligopeptide of item 1 wherein said oligopeptide comprises at least three epitopic peptides.
4. The oligopeptide of item 1 wherein said oligopeptide comprises at least four epitopic peptides.
5. The oligopeptide or peptide of item 1 wherein said oligopeptide or peptide differs from SEQ ID NO: 1, 2, 3, 4, 5, 6, 7, 8, 9, 10, 11, 12 13, 14, 15, 16, 17 or 18 wherein said difference is no more than one amino acid unit.
6. The oligopeptide or peptide of item 5 wherein said one amino acid difference is the result of a conservative amino acid substitution.
7. The oligopeptide or peptide of item 5 wherein said one amino acid difference is the substitution of one hydrophobic amino acid with another hydrophobic amino acid.
8. The oligopeptide or peptide of item 5 wherein said amino acid difference is the addition or deletion of one amino acid to or from said epitopic peptide.
9. A polynucleotide in a pharmaceutical composition comprising a polynucleotide selected from the group consisting of: (a) a polynucleotide that encodes an oligopeptide or peptide of item 1, and (b) the full complement of (a) wherein the polynucleotide is in a form of a pharmaceutically acceptable salt.
10. The polynucleotide of item 9 wherein the polynucleotide of (a) is DNA.

11. The polynucleotide of item 9 wherein the polynucleotide of (a) is RNA.
12. A method for vaccinating and treating a subject for Influenza infection, said infected cells expressing any class I MHC molecule, comprising administering to said subject a composition that binds to class I MHC molecules or can be processed to bind to class I MHC molecules comprising: at least one polypeptide comprising an epitopic peptide comprising an amino acid sequence selected from the group consisting of SEQ ID NO: 1 to 18 in an amount sufficient to induce a CTL response to said infected cells and in a form of a pharmaceutically acceptable salt; or at least one polypeptide comprising an epitopic peptide having at least one amino acid difference from an amino acid sequence selected from the group consisting of SEQ ID NO: 1 to 18 in an amount sufficient to induce a CTL response to said infected cells and in a form of a pharmaceutically acceptable salt.
13. A method for vaccinating and treating a subject with Influenza infection, said infected cells expressing any class I MHC molecule, said method comprising administering to said subject a composition that binds to class I MHC molecules or can be processed to bind to class I MHC molecules comprising: a polynucleotide comprising a nucleic acid sequence encoding at least one polypeptide comprising an amino acid sequence selected from the group consisting of SEQ ID NO: 1 to 18 in an amount sufficient to induce a CTL response to said infected cells and in a form of a pharmaceutically acceptable salt; or at least one polypeptide comprising an epitopic peptide comprising one amino acid difference from an amino acid sequence selected from the group consisting of SEQ ID NO: 1 to 18 in an amount sufficient to induce a CTL response to said infected cells and in a form of a pharmaceutically acceptable salt.
14. A method for generating an immune response ex vivo using T cells from a subject infected with Influenza, said method comprising: stimulating the production of CTL response for use in passive immunotherapy, wherein said T cells react with at least one polypeptide comprising an amino acid sequence selected from the group consisting of SEQ ID NO: 1 to 18 and in a form of a pharmaceutically acceptable salt; or at least one polypeptide comprising one amino acid difference from an amino acid sequence selected from the group consisting of SEQ ID NO: 1 to 18 and in a form of a pharmaceutically acceptable salt.
15. The method of item 14, wherein said T cell adoptive therapy generated from autologous or HLA matched subjects.
16. A method for assessing or diagnosing an immune response in a subject infected with Influenza or vaccinated for Influenza and related viruses said method comprising: stimulating the production of CTL response, wherein said T cells react with at least one polypeptide comprising an amino acid sequence selected from the group consisting of SEQ ID NO: 1 to 18 and in a form of a pharmaceutically acceptable salt; or at least one polypeptide comprising one amino acid difference from an amino acid sequence selected from the group consisting of SEQ ID NO: 1 to 18 and in a form of a pharmaceutically acceptable salt.
17. A method for vaccinating humans against Influenza infection using SEQ IDs 1 to 18 in a form of a pharmaceutically acceptable salt The following Examples illustrate the invention.

Example 1

Introduction

Influenza is a significant global health problem, infecting up to 20% of the world's population annually, causing up to 5 million cases of severe illness and >300,000 deaths worldwide. In the U.S. alone, an estimated >30,000 deaths and nearly 300,000 hospitalizations are attributed to influenza infection each year (1). With the recent appearance of new, severe and potentially recurrent seasonal disease, widespread vaccination campaigns that reduce the incidence of influenza-induced pneumonia are being encouraged by the World Health Organization. Effectively reducing the incidence of influenza will require continued intense surveillance, increased use of currently available influenza vaccine, and availability of alternative vaccines and antiviral medications that can provide broader protection against shift-and-drift strains of influenza (1). Successful influenza vaccination campaigns can have enormous societal and economic impact (2).

Immune Response to Influenza Virus

The immune response to influenza is governed by both innate and adaptive immunity. The innate immune response to influenza limits initial viral replication but is relatively non-specific (3). Efficient clearance of influenza virus requires a robust adaptive immune response, activating both humoral and cell mediated immunity. Humoral immunity, as mediated by secretory IgA and IgM. Antibodies, provides protection against the establishment of initial infection, while IgG neutralizes newly replicating virus in established infection (4, 5). Although inducing humoral immunity to influenza is the target of current conventional influenza vaccines, these are not completely protective due to occurrence of antigenic variations (6) (7). Additionally, data indicate that T-cell responses are extremely important for protection against influenza. CD4+ T cells play a critical role in isotype-switching to IgG and in the generation of higher affinity antibodies (8) and CTL memory (9-11). In humans, HA-specific CD4+ T cells proliferate following influenza vaccination (12) and aid the development of heterosubtypic influenza antibody responses (13, 14). CD8+ cytotoxic T lymphocytes (CTLs) mediate viral clearance and, importantly, were shown to have cross-reactive responses to different subtypes of influenza A virus (15-17). This may explain the relative paucity of disease among older, potentially vaccinated, or exposed individuals to H1N1 infection.

Current Status of Influenza Virus Vaccine Development

Influenza vaccines now on the market are updated yearly and are designed based on annual WHO strain recommendations (16, 18) and manufactured prior to the beginning of an influenza season or pandemic. Current vaccines for influenza induce a protective humoral immune response against the HA and NA glycoproteins on the virion surface (7, 19, 20). However, viral HA and NA glycoproteins are highly susceptible to frequent and unpredictable antigenic shift and less frequent, but more severe, drift mutations, which result in loss of antibody recognition necessitating frequent development of new vaccines to match the current viral serotype(s) infecting the human population (21-25). In addition, these vaccines are costly to produce, and will not protect against novel strains that may emerge mid-season (i.e. 2009 H1N1 swine flu, H5N1, H7N9). Most importantly, these vaccines focused on antibody based protection and induce limited T cell responses that are essential for eliminating infected cells from the body.

Three improved seasonal influenza vaccines currently have FDA approval. These quadrivalent vaccines provide coverage against two influenza A and two influenza B viruses. (In recent years, two influenza B viruses have co-circulated during influenza seasons and the trivalent vaccines offered did not protect against one of these strains). FluMist, a quadrivalent live attenuated vaccine that may provide more targets for the immune system because of limited protein synthesis (which is absent in inactivated vaccines). FluMist (http://www.cdc.gov/flu/protect/vaccine/vaccines.htm) is currently distributed as an alternative to the trivalent inactivated vaccine. Fluarix and FluZone are quadrivalent inactivated vaccines that stimulate a similar immune response to the current trivalent inactivated vaccine. These will be distributed in the 2013-2014 influenza season (http://www.fda.gov/BiologicsBloodVaccines/Vaccines/ApprovedProducts/ucm295057.ht m). Despite the coverage offered by the quadrivalent vaccines, these are still seasonal and suffer from the same downfalls as the trivalent vaccine, namely production times and costs and the lack of strong T cell responses that eliminates infected cells and protection against mid-season emergents. It is readily apparent that a universal vaccine offering protection against most, if not all, influenza strains is necessary.

To date, multiple universal vaccine formulations are in development. These vaccines can be broadly characterized by the type of protective immune response that is stimulated: 1) B cell responses (antibody), 2) T cell responses, or 3) both B and T cell responses. Kanekiyo et al. generated HA nanoparticles (hemagglutinin (HA) protein of influenza is fused to ferritin) that induce high titer antibody responses that provide coverage against multiple influenza strains (26). This vaccine has yet to enter into clinical trials. A T cell based vaccine that targets four relatively conserved epitopes in the viral genome (27) is also under development. A highly conserved CD4 epitopes based T cell vaccine has been evaluated in a phase II challenge study with positive protective responses against various influenza strains including pandemic strains (28). A recombinant polyepitope vaccine, called Multimeric-001, that incorporates B cell, CD4 T cell-, and CD8 T cell conserved epitopes from nine different influenza proteins (29) is being tested in early stage clinical trials. A fusion protein vaccine consisting of nucleoprotein (NP) and the B cell epitope M2e linked to an adjuvant and M2e peptide in gold nanoparticle in combination with CpG (30) are also under development. Most of the above mentioned vaccines are formulated as protein or peptides with various adjuvants that induce clinical adverse reactions. In contrast, our fully synthetic universal influenza vaccine formulation consists of a panel of conserved CD4, CD8 and B cell activating epitopes formulated in a gold nanoparticle vaccine delivery that has built in adjuvant properties, designed to stimulate potent T and B cell immune responses directed against many influenza virus strains including the newly emerged strains.

Synthetic Universal Vaccine Concept for Influenza Infection

An ideal vaccine should attempt to mimic natural immunity (FIG. 1) generated by infection in a manner whereby adaptive humoral and cellular immune memory is generated (31). Tremendous efforts are being made to develop a universal flu vaccine that would work against all types of influenza.

The goal is to provide protection for years, if not a whole lifetime, against all seasonal influenza strains and pandemic strains, making flu immunization much more like that for traditional vaccines. Development of an effective universal influenza vaccine would eliminate (or lessen) fears of future influenza pandemics and would be cost effective compared to development and manufacturing of the annual seasonal influenza vaccines. Such a universal vaccine must target conserved influenza virus epitopes that do not vary from strain to strain and more importantly, should be presented by the MHC molecules on the infected cells. Ultimately, the most promising universal influenza vaccine candidate may come from combining the antigens for both T and B cell immunity. Based on animal models and human studies, combining all possible T and B cell ligands (FIG. 1) to formulate an active synthetic vaccine makes sense. In order to be active, the vaccine must be in the size range to permit cytosol uptake with built in danger signals to target antigen presenting cells. Novel gold glyconanoparticles with these properties have been shown to induce efficient vaccine responses (32, 33). Development of a synthetic universal vaccine based on shared T cell and B cell epitopes incorporated in the gold nanoparticle is the focus of this application.

Innovation

This proposal has two major, novel distinctions: (1) the development of a fully synthetic universal vaccine that is capable of inducing T helper, cytotoxic T cell and antibody responses against multiple strains of influenza infection and (2) the characterization of a novel fully synthetic novel gold glyconanoparticle vaccine delivery platform armed with innate and adaptive immune stimulating molecules that will serve as potent adjuvant for any subunit vaccine. The proposed vaccine approach would have several advantages over the existing vaccines. First, it would have multiple conserved MHC class I restricted CD8+ T cell epitopes naturally processed and presented on infected cells (34), CD8 epitopes nested within CD4 epitopes, and antibody epitope/s from various influenza viral proteins. Second, these epitopes will be delivered in synthetic glyconanoparticle that contains immune "danger signals" (35, 36). Finally, this 20-40 nm sized novel glyconanoparticles unlike other nanoparticles, contains non-self-components (such as bacterial carbohydrates, GlcNAc) in addition to influenza specific T and B cell activating epitopes, is more likely to target and be taken up by antigen presenting cells due to its similarity to a pathogen, for efficient activation of antigen-specific T cell and antibody responses. These glyconanoparticles are also anticipated to induce DC maturation/activation, and thus, a robust immune response, which are essential for a successful, specific, subunit vaccine response (37, 38). These nanoparticles are also amenable to various delivery routes including transdermal and oral/buccal in addition to intradermal and subcutaneous injection mode of delivery.

This proposal is also intended to accelerate the pre-clinical development of a novel emerging vaccine strategy that has built-in cross-subtype efficacy, which could prevent the significant spread of an emerging or re-emerging strain of influenza infection. A cross-subtype vaccine containing immunogenic consensus sequence epitopes could achieve this goal. Mounting evidence suggests that an efficient universal vaccine must induce activation of both cell mediated and humoral immunity. We hypothesize that vaccines based on defined epitopes presented by the infected cells would be far superior to a viral protein subunit or a motif predicted epitope based vaccines because protein processing by the immune system may alter the native viral epitopes. In addition, CD8 epitope nested within extended peptides not only generate a robust CTL response but the extended peptides are also capable of inducing T helper mediated cytokine responses, which are critical to combat influenza infection (28). An addition of a universal antibody epitope to this synthetic vaccine formulation incorporates both arms of the immune system for complete protection.

As demonstrated by our preliminary data, direct identification of T cell epitopes presented by the infected cells is an efficient and logical method to identify T cell epitopes for vaccine applications. Our analysis confirmed a few T cell epitopes that were selected by MHC motif prediction methodologies. Since the immune epitope database (http://www.iedb.org) contains several hundreds of predicted HLA specific influenza T cell epitopes, including a number of shared epitopes with high MHC binding scores and limited CTL characterization, it is critical to confirm and use for vaccine application epitopes that are presented by the virus infected cells. Additionally, because the IEDB database is generated by motif prediction methods, and not functional methods, it would be difficult to sort out the dominance hierarchies of naturally presented epitopes. Thomas et al. (39) elegantly demonstrated that both dominant and sub-dominant epitopes are presented by the infected cells, which would be difficult to sort out using the data in the IEDB database. One additional drawback of the motif predicted epitopes is that most often they were screened for functional specificity using CTL from infected individuals, which may have been tolerized.

Significant innovation will be realized in the first ever combination of T cell (CD8 and CD4) epitopes and an antibody epitope (M2e) formulated in a targeted, immune activating and regulating, fully synthetic, flexible nanoparticle vaccine delivery system. We emphasize that the use of the conserved T cell epitopes that are naturally presented by the infected cells and B cell epitope incorporated in the nanoparticles represent a major leap in vaccine technology rather than a small adjustment to the vaccine constituents. If successful, this method could lead to a paradigm shift in how prophylactic and therapeutic vaccines are formulated. Our work will also be useful in advancing the general understanding of the T cell mediated immune response to influenza virus infection. This information is critical to the development of anti-viral drugs and prophylactic and therapeutic universal vaccines to combat and prevent serious, and some cases, lethal influenza virus infection.

Results

We identified a panel of HLA-A2 specific conserved epitopes from the infected cells. Using peripheral blood mononuclear cells (PBMC) obtained from HLA-A2 positive healthy donors we have characterized selected epitopes for CTL activity and demonstrated cross reactivity in vitro.

Identification of MHC Class I Presented Influenza Epitopes

JY, an HLA-A2 and B7 positive EBV transformed B cell line and HLA-A2 and A24 positive HepG2, a hepatoma cell line and Dendritic cells (DCs) generated from HLA-A2 positive peripheral blood lymphocytes (PBL) from healthy individuals were infected with Influenza A and B viral strains (A/New Caledonia/20/99 (H1N1), A/Wisconsin/67/2005 (H3N2), B/Malaysia/2506/2004). For both JY and DC, published studies have shown cellular infection to be ~50% upon using ~10 HAU (40) for 16-24 h are most successful for influenza infections (41). The infected cells were used for the isolation of MHC peptides if they showed >50% infectivity. Cell lysates were prepared and subjected to two rounds of immunoprecipitation using 1 mg of W6/32 (pan MHC class I specific antibody) conjugated to 1 mL of Protein A/G beads (34). The bound MHC complexes were eluted from the beads and peptide mixtures were purified and fractionated using C18 reversed phase (RP) column. The peptide fractions were injected individually into LC-MS/MS system (nanoAcquity UPLC-LTQ orbitrap) to identify the MHC peptides. MHC peptides and their corresponding proteins were identified by searching the raw data in NCBI influenza database using bioworks/proteome discoverer software (Thermo). Synthetic peptides were made to validate and confirm the sequences. The synthetic peptides were subjected to LC-MS/MS analysis under identical collision conditions as the experimental and their sequences were confirmed by comparison of their MS/MS spectra with that of their synthetic analogs.

Table 31 summarizes the MHC class I-associated peptides that we have identified from influenza virus infected cells. We identified 7 epitopes with the HLA-A2 binding motif and 5 of the 7 epitopes had a HLA-A24 cross binding motif. In addition, we identified several HLA-B7 and B44 motif containing epitopes. All the epitopes originate from regions of the proteins that are conserved between multiple influenza strains. These peptides were confirmed in co-elution experiments using synthetic peptides. Interestingly, we identified three previously reported epitopes, two HLA-A2 specific epitopes (P1 and P5) (42), which were identified using motif-prediction and ex vivo CTL analysis and one HLA-B7 specific epitope (LPF in table 3) that is shown to be conserved between pandemic H1N1-2009 and H1N1-1918 influenza A viruses (43).

TABLE 3

MHC class I epitopes presented by influenza virus infected cells

| Seq ID | Peptide | Protein | HLA motif |
|---|---|---|---|
| | YINTALLNA* (P1) | polmerase PA | A2 |
| 1 | PVAGGTSSIYI (P2) | polymerase PB2 | A2 |
| 2 | TVIKTNMI (P3) | polymerase PB1 | A2/ A24 |
| 3 | MTIIFLILM (P4) | hemagglutinin | A2/ A24 |
| | AIMDKNIIL* (P5) | nonstructural protein 1 | A2/ A24 |
| 4 | ITFHGAKEI | Matrix protein 1 | A2/ A24 |
| 5 | AINGITNKV | Hemagglutinin | A2/ A24 |
| 6 | EEMGITTHF | RNA-directed RNA polymerase catalytic | B44 |
| 7 | VETPIRNEW | Matrix protein 2 | B44 |
| 8 | REILTKTTV | Polymerase basic protein 2 | B44 |
| 9 | KESDEALNMTMASTP | Non-structural protein NS1 | B44 |
| 10 | LENERTLDF | Polymerase acidic protein | B44 |
| 11 | MEAVPLITI | Hemagglutinin | B44 |
| 12 | VEQEIRTF | Nuclear export protein | B44 |

TABLE 3-continued MHC class I epitopes presented by influenza virus infected cells

| Seq ID | Peptide | Protein | HLA motif |
|---|---|---|---|
| 13 | VEQELRTF | nonstructural protein 2 | B44 |
|  | LPFDRTTIM* | nucleocapsid protein | B7 |
| 14 | SPDDFALIVNA | polymerase PB1 | B7 |
| 15 | YPDTGKVM | Neuraminidase | B7 |
| 16 | YPDASKVM | neuraminidase | B7 |
| 17 | QPETCNQSII | Neuraminidase | B7 |

*Previously reported epitopes

Figure 2:
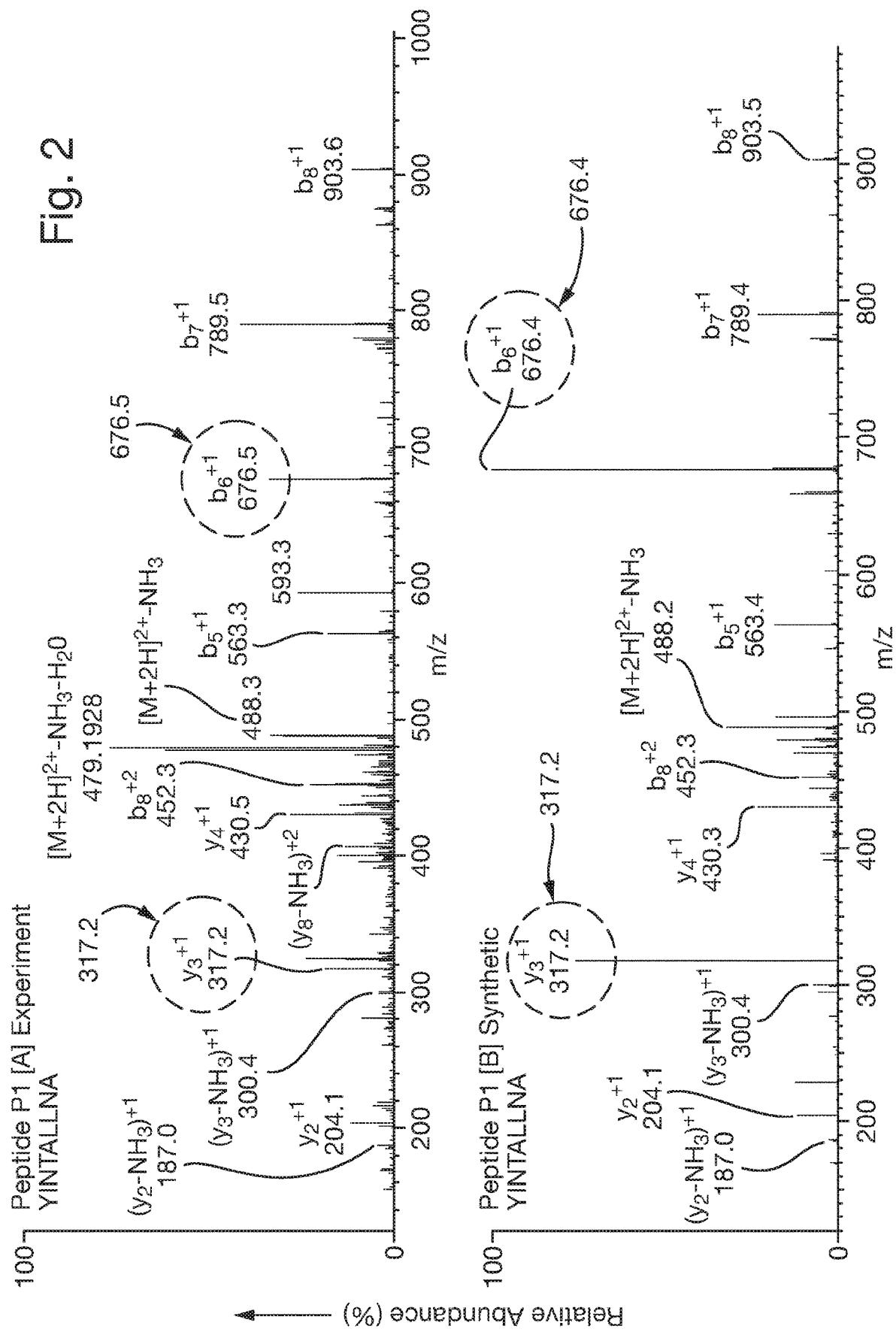
FIG. 2: Confirmation of influenza specific peptide sequences.

Prior to CTL functional characterization experiments, we confirmed the authenticity of 5 HLA-A2 specific peptides, P1-P5 (Table 3) using their synthetic peptide analogs. As illustrated in FIG. 2, most of the fragment ions in the ms/ms spectra of experimentally identified peptides (FIG. 2: P1-A-P5-A) matched with spectra of their corresponding synthetic peptides as indicated by the denoted masses (FIG. 2: P1-B-P5-B) (34). In addition, we further verified the ms/ms spectra manually to confirm the identity of all the experimentally observed peptides. T cell epitopes were formulated into the nanoparticles and tested for induction of epitope specific CTL and cross reactivity in vitro.

Figure 3A:
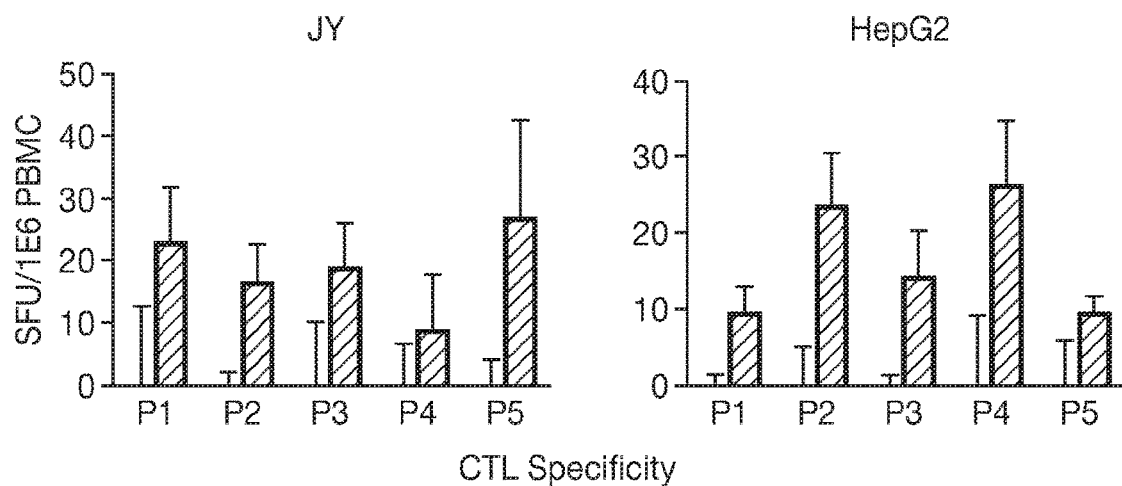
FIG. 3: Epitopes (P1-P5) specific CTLs generated in vitro with human PBMCs recognize both peptide loaded (panel A) and various influenza virus infected (panel B) target cells.
Figure 3B:
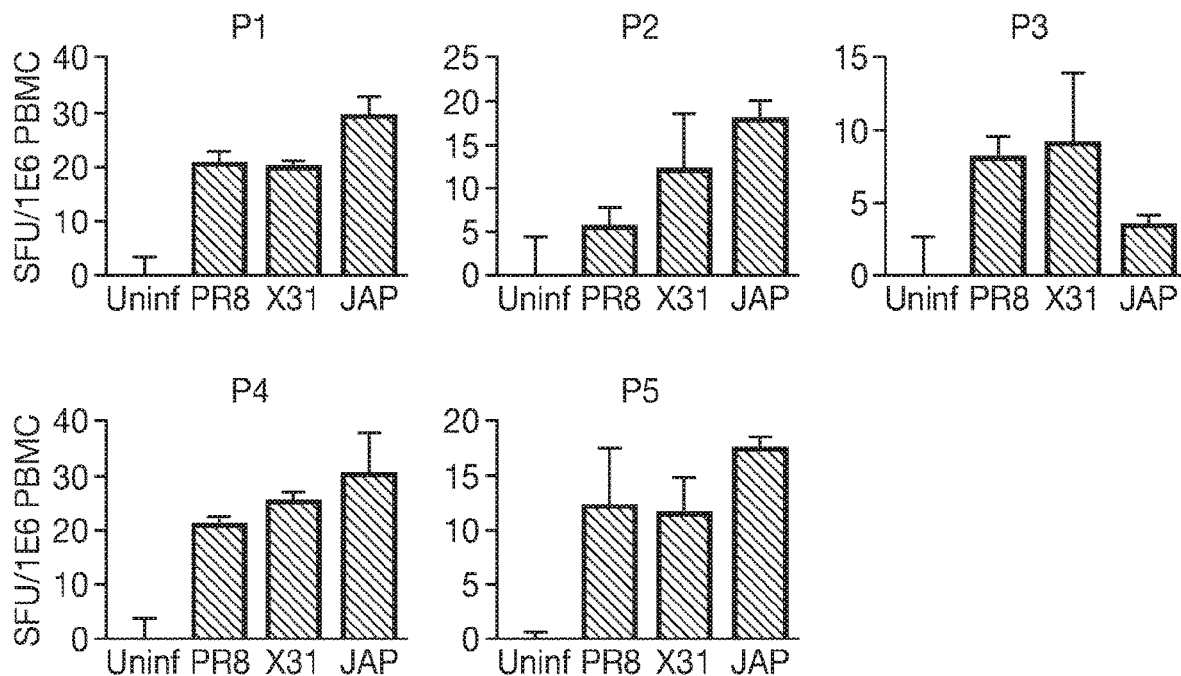

To verify the presentation of these epitopes by infected cells, CTLs specific for each of the 5 peptides were generated using PBMCs from healthy HLA-A2+ donors and synthetic peptides corresponding to the identified epitopes. In ELISpot assays, CTL functionality was measured by detection of antigen specific IFNγ secretion. As illustrated in FIG. 3A, PR8-infected JY and HepG2 cells stimulated all five of the influenza epitope-specific T cells. Additionally, cross-reactivity to other strains was demonstrated using HepG2 target cells infected with various influenza A strains (X31, H3N2 and JAP, H2N2), indicating the presentation of these epitopes in various influenza strain-infected cells (FIG. 3B).

To further characterize the immune response generated by these epitopes in vivo, we immunized HLA-A2+ transgenic mice with a mixture of the aforementioned five epitopes. Immunizations were carried out using these peptides in the presence of Montanide ISA 51 as an adjuvant (FIG. 4A). We determined the influenza-specific T cell response by measuring murine IFNγ secretion in an ELISpot assay. Using T2 cells pulsed with individual peptides 1-5, we observed a response to all 5 peptides after immunization (FIG. 4B). In conjunction with above in vitro results, in vivo-generated CTLs specific for these peptides were stimulated equally well when HepG2 and JY cells infected with different strains of influenza were used as targets (FIG. 4C) indicating that these epitopes are processed and presented in multiple influenza infections. In addition to IFNγ release, we also measured the phenotypic changes of CD8+ T cells from splenocytes with regards to CD107a, an activation marker present on granulating effector CTLs (44, 45). As illustrated in FIG. 4D, CD8+ T cells displayed a higher intensity of CD107a staining when incubated with infected targets compared to uninfected targets.

We generated gold nanoparticles (NP) incorporating HLA-A2 specific epitopes (NP 1-5) and combined with a shared antibody epitope (NP 6) from influenza matrix 2 protein (M2e). We immunized HLA-A2 transgenic mice with either peptide+montanide 51 or peptides in NPs and assessed CTL response by IFNγ release using ELISpots (FIGS. 5A and B) and CD107a expression (FIG. 5C). Peptides incorporated in NPs activated a strong anti-viral CTL response in vivo without any addition of adjuvant. NPs themselves acted as adjuvant in addition to delivering peptides to the antigen presenting cells. Peptides without montanide adjuvant did not elicit a CTL response (data not shown).

Figure 6:
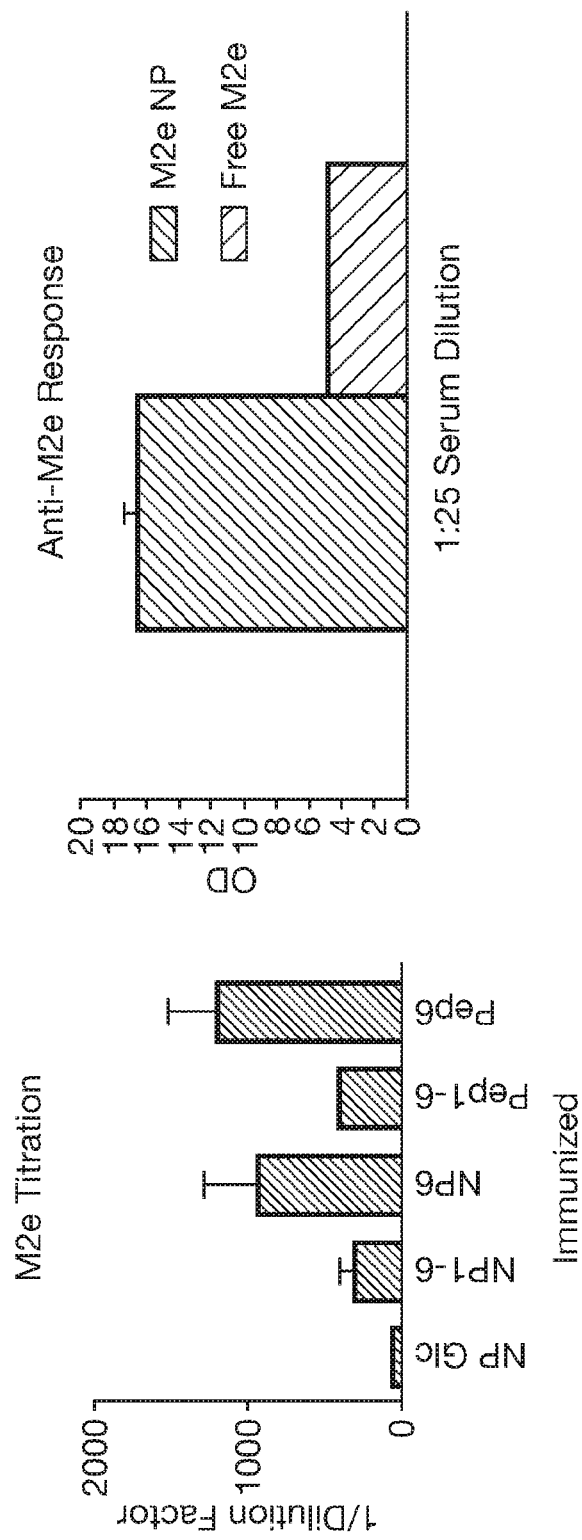
FIG. 6: Immunization of M2e peptide+adjuvant (Pep 6) or in NP (NP6) induce specific antibody response (panel A). No antibody response with free peptide without adjuvant (panel B).

In addition to characterizing CTL responses, we also evaluated antibody responses to a universal antibody epitope from influenza matrix 2 protein (M2e). To this end, we immunized a group of mice with MHCI peptides (P1-5) or peptides in GNP (NP1-5) in addition to a peptide (P6 or NP6) from the ectodomain of M2 (M2e) (46, 47). The T cell response as measured by IFNγ ELISpot assay (FIGS. 5A&B) and CD107a (FIG. 5C) flow cytometric analysis were comparable between the groups immunized with T cell epitopes alone (1-5) or T cell epitopes with the M2e peptide (1-6). The concentration of circulating M2e-specific antibody was then measured by a standard ELISA using serum collected from the terminal bleeds of immunized mice. As illustrated in FIG. 6, mice immunized with the M2e peptide with montanide adjuvant (Pep6) or in GNPs (NP6) generated a robust and M2e specific IgG response (FIG. 6A). However, when the M2e peptide is combined with the MHC1 peptides (Pep1-5 or NP1-5), the antibody titer against M2e was slightly reduced. There was no difference between the peptides+montanide adjuvant and GNPs without any adjuvant in the antibody response as we observed in the T cell response. However, when we compared free peptide without any adjuvant with NPs, we observed a greater antibody response with NPs (FIG. 6B). In summary, we demonstrate that GNP incorporated MHCI and antibody epitopes generate robust both CTL and antibody responses as compared to epitopes that require adjuvants, which induce clinical toxicity.

Figure 7:
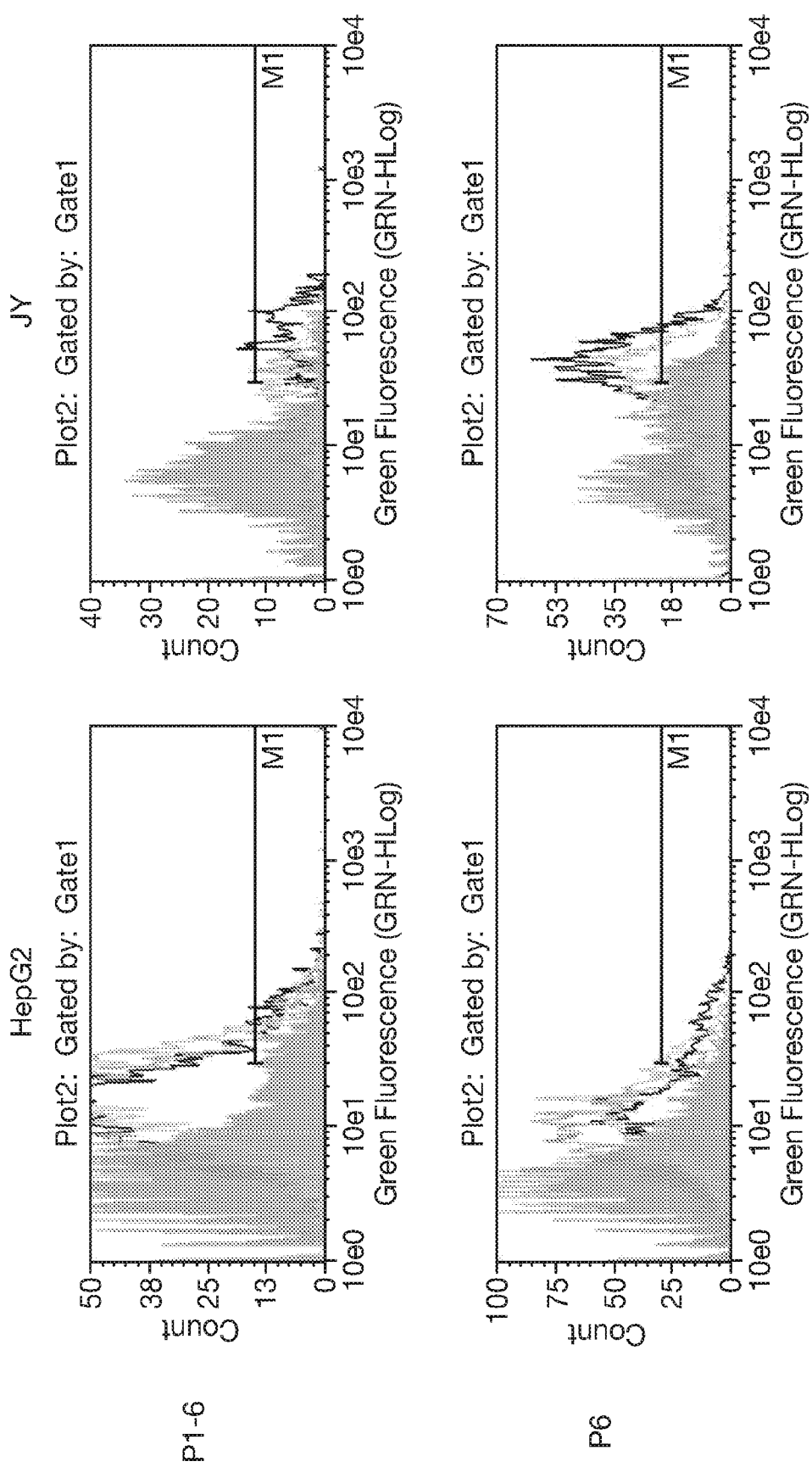
FIG. 7: M2e peptide specific antisera binds to M2e epitope on influenza virus infected cells (PR8, X-31, or JAP (green, aqua, red respectively).

Functionality of the M2e antisera generated by peptide+montanide adjuvant (P1-6, P6) and peptides in NPs (NP1-6, NP6) for cross reactivity were then characterized by infecting HepG2 and JY cells with all three strains of influenza virus (PR8, X-31, or JAP) that we have thus far tested. Using flow cytometry, we treated the infected cells with the M2e-specific antisera obtained from peptide+montanide or NP immunized mice and demonstrated the binding of the antibody specifically on PR8, X-31, or JAP (green, aqua, red respectively) infected cells indicating the presence of this epitope in various strains of influenza infected cells (FIG. 7).

Figure 8:
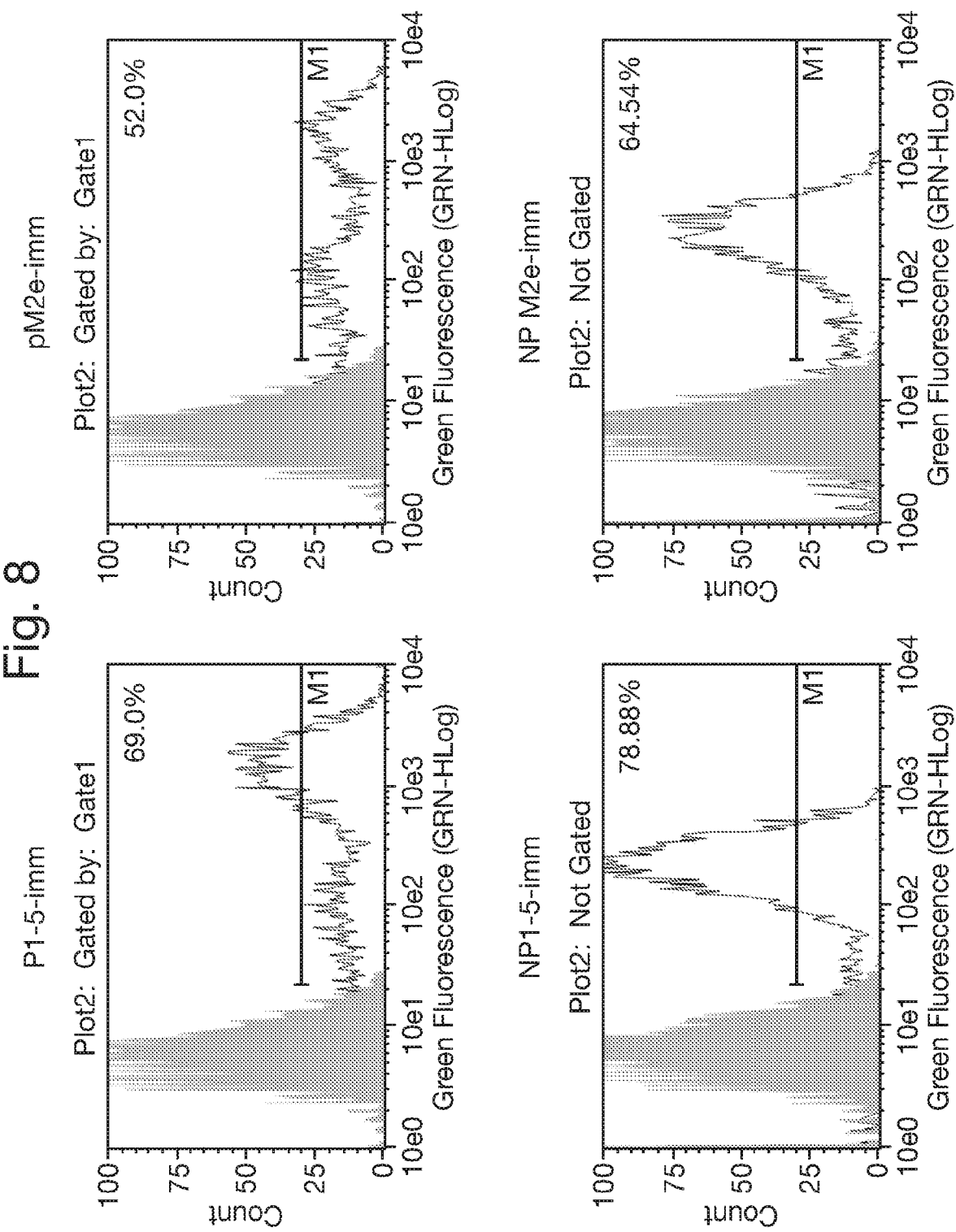
FIG. 8.

Lastly, the neutralizing ability of these antibodies was determined by adding antisera to HepG2 cells infected with PR8 virus. HepG2 cells were pulsed with a low dose of PR8 in the presence of serum from MHCI peptides (P1-5 or NP 1-5), or pM2e peptide (pM2e or NP M2e) immunized mice at a 1:50 dilution for 1 hr. Following overnight incubation with the same levels of serum, cells were fixed and intracellularly stained for influenza NP. Percent positive cells are depicted. Gray-filled histograms are uninfected controls. As illustrated in FIG. 8, infection levels were lower when the serum containing anti-M2e antibody obtained from M2e peptide with montanide adjuvant (FIG. 8A) or M2e peptide in GNP (FIG. 8B) was used indicating the functional ability of the M2e specific antibodies.

Summary

These are the first ever comprehensive study reported on MHC class I associated peptides analysis of influenza virus infected cells. Significantly, all the epitopes are shared between different strains of influenza. Interestingly, we also identified a few already reported motif predicted epitopes on the infected cells. Further to MHCI epitopes characterization, we have also demonstrated that the broad anti-viral activity of the antibodies against the M2e antibody epitope. We have also generated gold nanoparticle (GNP) formulated with T and antibody epitopes and characterized anti-viral T and antibody responses in in vitro and in vivo studies. The data we have generated will have a significant impact on universal influenza vaccine development, formulation and characterization. Our work will also be useful in advancing the general understanding of the T cell mediated immune response to influenza virus infection. This information is critical to the development of anti-viral drugs and prophylactic and therapeutic universal vaccines to combat and prevent serious, and some cases, lethal influenza virus infection.

Future Work

We propose to evaluate the frequency of T cells specific for these epitopes and M2e antibody response in the seasonal vaccinated individuals to assess the endogenous cell mediated and humoral responses in influenza infection. In line with this aim, we have preliminarily investigated the presence of M2e specific antibodies in a general population exposed to influenza infection and had seasonal vaccination. We obtained (purchased from Research Blood Components LLC, Brighton, Mass.) serum samples from 10 healthy individuals (5 male and 5 female). The presence of antibodies against the conserved M2e epitope was assessed using a standard ELISA assay.

Various dilutions of the serum samples were applied to M2e peptide coated ELISA wells and treated with anti-human IgG secondary antibodies and Licor detecting agent (34). The actual image of the ELISA wells is shown for each of the individuals with 4 different dilutions. The data shown in FIG. 9 clearly indicates that some of the individuals do produce antibodies against the conserved M2e epitope. However, the titers sof some of the individuals were very low. It is interesting to note that influenza infection, and may be the seasonal vaccination, does induce endogenous antibody response to this universal antibody epitope. Immunization with this universal epitope and generating a robust antibody response may induce effective protection. We plan on testing this hypothesis in the phase II proposal.

Figure 10:
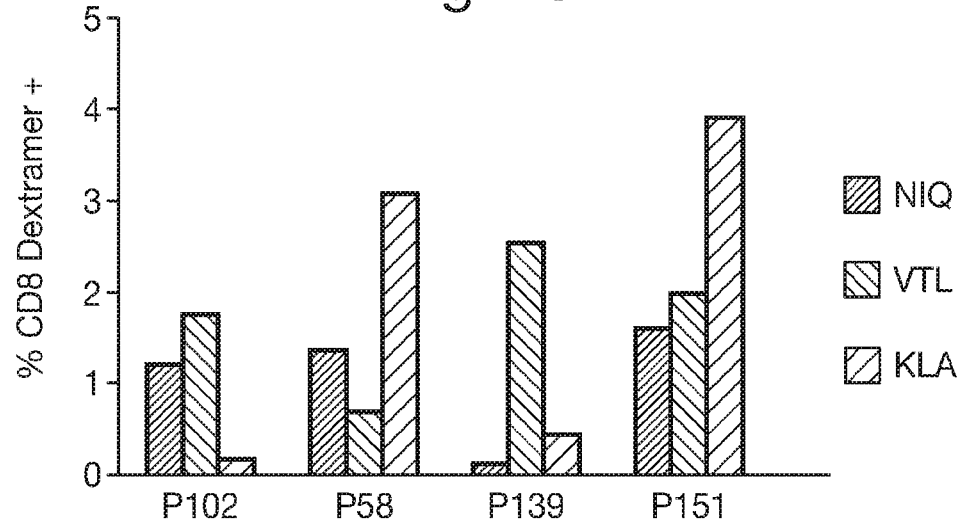
FIG. 10: Detection of pre-existing epitope specific CTLs via dextramer analysis of PBMCs from dengue sero-positive individuals.
Figure 11:
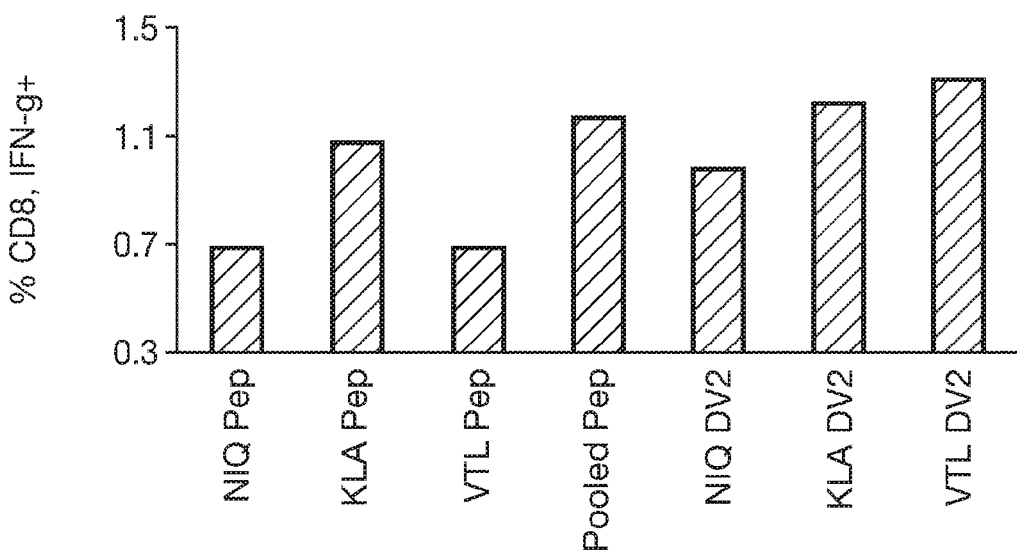
FIG. 11: Epitope specific CTLs in seropositive individuals recognize peptide loaded (pep) and dengue virus infected (DV2) target cells.

In addition to the antibody response to the universal B ell epitope, we are also planning on evaluating the frequency of T cells specific for the MHCI epitopes that we have identified and characterized in the phase I proposal. To accomplish this task, we propose to synthesize MHC tetramer or dextramers with the specific epitopes and screen PBL from individuals who were exposed to influenza virus and have gotten seasonal flu vaccination. We have extensive experience in MHC dextramer analysis using T cell epitopes derived from dengue virus infection. We have screened several patients seropositive for dengue virus using 3 HLA-A2 specific T cell epitope containing dextramers. The dextramers were synthesized by Immudex (Fairfax, Va.). PBMCs were purified from whole blood and stained with anti-CD8 antibodies and dextramers. The stained cells were analyzed in Guava flow cytometer and the percent positive data were generated using Guavasoft InCyte software. Four patients with three different epitope (NIQ, VTL, KLA) specific dextramer data is shown in FIG. 10. All patients had some level (0.5%-4%) of circulating CD8+ T cells that specifically bound to the T cell epitope dextramers. We also stimulated these T cells with specific peptides in in vitro short term cultures and obtained specific CTL response data (FIG. 11). PBL from dengue seropositive patient who showed high percentage of dextramer staining, p151 (FIG. 10) was stimulated with peptides in culture for 7 days. The activated T cells were assessed for CTL function by intracellular staining of IFNγ production and flow cytometry analysis. As shown in FIG. 11, CTL activity was significant (0.7%-1.1%) against individual peptide loaded targets (NIQ pep, KLA pep, VTL pep) as well as dengue virus serotype 2 (DV2) infected targets (NIQ DV2, KLA DV2, VTL DV2). The dextramer and CTL analysis data may not be directly comparable, however, it is interesting to note that the dextramer positive cells are capable of being reactivated with specific epitopes and the CTLs are functional in recognizing virus infected cells.

In order to harness the activation of both virus specific CD4 and CD8 T cell responses, we propose to synthesize the identified CD8 T cell epitopes nested within extended 15mer peptide containing endogenous sequences. These longer peptides have the potential to stimulate CD4+ T cells. To evaluate the efficacy of such longer peptide for inducing CTL activation, we tested a well characterized model CD8 T cell epitope from ovalbumin (SIINFEKL) (48). We synthesized an extended peptide by including three endogenus flanking aa residues at both the N and C terminus of SIINFEKL (QLE SIINFEKL TEW) and assessed the longer peptide to be processed and present the CD8 epitope for T cell activation.

As demonstrated in FIGS. 12A and B when the model ovalbumin H2Kb epitope containing extended peptide was processed and presented by the APCs (LK$^b$ cells) (FIG. 12A) and T cell recognition and activation was achieved (FIG. 12B) indicating CD8 epitope nested longer peptide is capable of being processed and activating T cells. Although the presentation of CD8 epitope was lower in Ext SIIN pulsed LK$^b$ cells as compared to free peptide loading, which was expected since Ext SIIN require internalization and further processing, the activation of T cells was equivalent in Ext SIIN pulsed APC, which is more critical. The assumption is that these longer peptides will also act as helper peptide in vivo for potent CTL and B cell activation for anti-influenza vaccine response.

Nanoparticle Delivery Safety Validation

Though the GNP vaccine compositions have never been tested in humans, they have been evaluated in a phase I clinical study for the safety and delivery of insulin peptide in healthy volunteers demonstrating good safety thus far. In addition, previous in vivo and in vitro safety studies indicate that the particles are safe at very high concentrations in large animal toxicology studies. All individual components of the nanoparticles are synthetic and have shown no toxicity when administered individually. The safety of the GNP formulations have been tested in in vitro studies using various cancer cell lines, whole blood, and human buccal mucosa for cell proliferation, cytokine release and cytotoxicity with no adverse effects observed. Various vaccine and metastasis tumor models have been used to perform toxicology studies using the nanoparticle vaccine formulations with no toxicity detected. In addition, no toxicities were observed in CSIS in vivo imaging studies in a mouse brain GL261 glioma model and retinal vessel studies. GLP toxicology studies were performed with the nanoparticles administered intravenously daily to mice for 5 consecutive days at a theoretical dose of 5.4 mg/kg with no clinical sign of toxicity in urine, fecal excretions or in organs including brain, liver, kidney, heart, spleen and lung.

Overall Conclusion of the Prior Work

The work presented in this section highlights the versatile nature of the GNPs as a multi-epitope vaccine delivery platform and our strengths in immune analysis of viral infection. Particularly relevant to this study is our extensive experience with MHC-associated peptide analysis, T cell epitope identification and characterization of epitopes for T cell functions in vaccine delivery systems (49-52). Based on our preliminary work in cancer (53, 54) and infectious diseases including influenza (34) and dengue (55), we believe that we will be successful in accomplishing the proposed project. It is important to note that the vaccine delivery platform and the T cell epitope identification methodologies are broadly applicable to other infectious diseases as well.

Methods

CTL Frequency Analysis

Buffy coat samples from HLA-A2 or A24 positive healthy individuals who received the seasonal flu vaccination will be purchased from Research Blood Components LLC (Brighton, Mass.). We propose to assess 6-10 patients. Peptide MHC Tetramer (Proimmune) and Dextramer (Immudex) constructs with HLA-A2 and A24 specific peptides will be obtained. PBMCs will be purified from buffy coats following standard methods. PBMCs will be stained with tetramer (56) or dextramer (57) constructs following the manufacturer's protocol. The cells will be co-stained with anti-CD8 antibody FITC conjugate. The stained cells were analyzed in Guava flow cytometer (Millipore) and the percent positive data were generated using Guavasoft InCyte software (FIG. 10). The double stained cells will be enumerated as percent total PBMC. Irrelevant, off the shelf peptide MHC tetramer or dextramer will be used as negative controls.

Activation of Memory and Naive CTL

For activation of naive T cells, peripheral blood from HLA-A2 or A24 positive healthy donors (purchased from Research Blood Components, LLC. Brighton, Mass.) will be obtained. Peripheral blood mononuclear cells (PBMC) will be purified using lymphocyte separation medium (Mediatech) using differential centrifugation following standard methods. PBMC will be plated in complete RPMI 1640 medium overnight. Non-adherent cells will be removed and saved. Plastic adherent cells will be pulsed with 50 µg/mL synthetic peptide and 1.5 µg/mL human β2-microglobulin (EMB Biosciences, Gibbstown, N.J.) in complete medium for 2 h. Non-adherent cells will then be added back in 5 mL complete medium supplemented with IL-7 at 5 ng/mL, Granulocyte Monocyte Colony Stimulating Factor (GM-CSF) at 25 ng/mL and IL-4 at 50 ng/mL (all cytokines and growth factors were purchased from Peprotech, Rocky Hill, N.J.). Plates will be incubated at 37° C. in a humidified incubator with 5% CO2 for 12 days. T cells will be restimulated once with autologous CD4+/CD8+ T cell-depleted PBMCs pulsed with synthetic peptide at 10 µg/mL and 1.5 µg/mL human β2-microglobulin in complete medium containing 5 ng/mL IL-7 and 10 U/mL IL-2 for 5 days. Restimulation will be repeated three times prior to use in the CTL assays. CTL assays will be performed using peptide loaded T2 cells and target cells infected with different strains of influenza as described in the publication (34). For memory T cell activation, PBMCs will be activated once with the peptide pulsed APCs as above prior to the CTL assays (FIG. 11).

Antigen stimulated interferon-γ (IFN-γ) and granzyme B release as a measure of CTL activation will be assayed in the respective ELISPOT assays (58, 59). Peptide-pulsed T2 cells, along with irrelevant HLA-A2 peptide pulsed T2 cells (1 microg/mL peptide for 2 hrs at 37° C.) will be used as controls along with influenza infected and uninfected cells as targets. In addition, secretion of various cytokines (IFN-gamma, TNF-alpha, Granzyme B) will be assessed by MagPix Luminex technology (Millipore). Appropriate controls, including peptide-unpulsed T2s and PHAs, to stimulate non-specific IFN-gamma induction by the CTLs as negative and positive controls will be included in all assays.

M2e Specific Antibody Response

Figure 9:
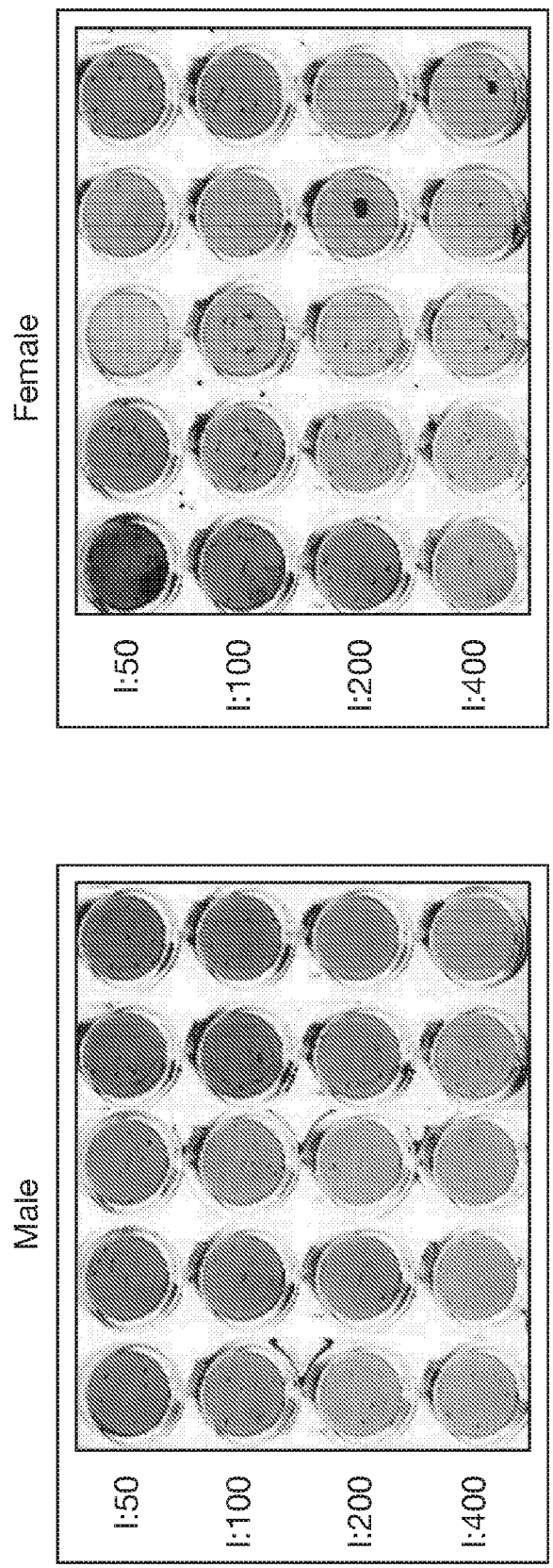
FIG. 9: Naturally occurring M2e antibody response in healthy individuals exposed to influenza virus.

Serum samples from healthy individuals who received the seasonal flu vaccination will be used to analyze the presence of conserved M2e epitope specific antibodies using standard ELISA techniques (FIG. 9). Additionally, serum samples will be used to measure the recognition of the M2e antibody epitope on the surface of infected cells. HepG2 cells will be infected with PR8, X31, and JAP viruses as described previously (34). After overnight incubation, cells will be stained with serum samples at a 1:50 dilution followed by FITC-labeled anti-mouse IgG (Invitrogen) secondary antibody. Samples will be analyzed using a Guava flow cytometer and GuavaSoft InCyte software.

Formulate NPs with CD8 Epitope Nested Longer Peptide and Characterize Both CD4 and CD8 Responses In Vitro and In Vivo Cell-mediated immunity (CMI), as elicited by major histocompatibility complex (MHC) class I-restricted CD8+ cytotoxic T lymphocytes (CTLs), plays a central role in controlling influenza virus infection (60-63) (6). CMI generated by primary influenza infection provides substantial protection against serologically distinct viruses due to the recognition of cross-reactive epitopes, often from internal viral proteins conserved between viral subtypes (64-66). Importantly, in addition to the role of CTLs in mediating viral clearance (67, 68), CD8+ T cells in humans were shown to have cross-reactive acute (15-17) and memory responses (25) to different subtypes of influenza A virus. Influenza infection studies in mice have revealed that viral clearance is mediated by antigen-specific CD8+ effector T cells, whereas memory CD4+ T cells are important in maintaining CD8+ T and B cell memory responses (69). Recently, both effector CD4+ and CD8+ T cells have been implicated in the control of pulmonary inflammation and limit excessive tissue damage by producing interleukin-10 (70). A potential protective role for CD4+ T cells has been suggested by in vitro studies demonstrating reactivity against previously unencountered strains, for example, against avian H5N1 by CD4+ T cells primed with seasonal strains (71-74). In the context of pandemics where there are no preexisting protective antibodies, T cells may mediate protection or limit the severity of influenza-associated illness in humans (75). Preexisting T cell responses have been shown to modulate influenza severity in the context of existing antibodies (15). Recently, Wilkinson et al. investigated the role of CMI in limiting influenza using extended CD4 activating peptides derived from the conserved regions of influenza genome in a human challenge model in healthy volunteers who lack detectable humoral immunity to the challenge strains and demonstrated broad spectrum of protection (28). Interestingly in some cases these extended peptides nested previously reported MHC class I epitopes that activate CD8+ T cell responses (28, 34). In light of the significant role of both the CD4 and CD8 positive T cell responses in protection against influenza infection, we propose to formulate the vaccine with the identified CD8 T cell epitopes nested within extended peptides that has potential to activate CD4+ T cells. In this aim we will synthesize extended peptides by including three endogenous flanking aa residues at both the N and C terminus of the A2 and A24 epitopes. These extended peptides will be formulated in gold nanoparticles and tested for both CD4 and CD8 positive T cell responses in vitro with human PBMCs and in vivo in A2 transgenic mice for CTL responses.

Preparation of Nanoparticles with Epitopes

Both the CD8 and extended CD4 peptides (Table 4) will be derived at the synthesis stage to contain a mixed aliphatic/polyethylene linker coupled to a cathepsin B cleavable dipeptide which is contiguous with the selected peptide epitopes. Peptide conjugates are incorporated into the nanoparticles by a single step, self-associating, chemical reaction which results in nanoparticles with gold metal cores of ~1.6 nm and a mixed ligand corona decorated with glucose and two-five carbon spacers as previously described (35). Peptide mixtures (0.94 mg each, 0.35 micromol) will be dissolved in TFA (20 microL) and the solution will be concentrated under an argon stream until the formation of an oil. MeOH will be added (1250 microL) and the reaction will be vortexed for 20 seconds. Glc-ligand (1.34 mg, 5.60 micromol) and GlcNHAc-ligand (1.23 mg, 4.37 micromol) will then be added to the methanol solution and the pH will be adjusted to 2 with TFA (2 microL). An aqueous solution of HAuCl4 (300 microL, 7.5 micromol) will be added and the solution vortexed for 20 seconds. An aliquot of 50 microL will be taken for further analysis of the gold content. A 1N aqueous solution of NaBH4 (165 microL, 165 micromol) will be added to the remaining solution in several portions with rapid shaking. The black suspension that forms will be shaken and pelleted by centrifugation. The pellet will then be dissolved in water and dialyzed. The ratio of the different ligands on the nanocluster surface will be assessed by comparing the 1H NMR spectra of the initial mixtures, the formed NPs and the recovered mother liquors after the self-assembly process as previously described (35).

TABLE 4

CD8 epitopes and the extended, potential CD4 epitopes.

| CD8 epitope | Extended epitope (potential CD4 epitope) | Protein | HLA motif |
| --- | --- | --- | --- |
| YINTALLNA | kgvYINTALLNAsca | polymerase PA | A2 |
| PVAGGTSSIYI | rflPVAGGTSSIYIevl | polymerase PB2 | A2 |
| TVIKTNMI | igvTVIKTNMInnd | polymerase PB1 | A2/A24 |
| AIMDKNIIL | mdqAIMDKNIILkan | nonstructural protein 1 | A2/A24 |
| ITFHGAKEI | kreITFHGAKEIsls | Matrix protein 1 | A2/A24 |
| AINGITNKV | tqnAINGITNKVnsv | Hemagglutinin | A2/A24 |

HLA restriction for CD8 epitope is shown.

Evaluation of Epitope Specific CD4$^+$ and CD8$^+$ T Cell Responses In Vitro

We propose to evaluate the ability of the nanoparticle vaccine formulations to activate specific CD4$^+$ and CD8$^+$ T cell responses. PBMCs will be isolated from donors as described above and pulsed with either the NP vaccine formulation or, as a control, synthetic peptides alone. Epitope specific T cells will be purified via positive selection using beads conjugated to either CD4 or CD8 antibodies (Dynabeads, Invitrogen), detached from the beads (DetahA-Bead, Invitrogen), and used in downstream applications. Freshly purified epitope specific CD4$^+$ or CD8$^+$ T cells will be cultured overnight with antigen presenting cells that are pulsed with relevant peptides or infected with different strains of influenza virus (PR8, X31, JAP). T cell activation will be assessed in three ways: 1) IFN-gamma ELISpot assay, 2) cytokine secretion as detected by MagPix Luminex technology (IFN-gamma, TNF-alpha, Granzyme B, IL-2) and, for CD8$^+$ T cell responses, 3) flow cytometry detecting the expression of the degranulation marker CD107a on CD8$^+$ T cells. In all experiments, uninfected and unpulsed APCs will be used as negative controls.

Expected outcome and technical challenges: We predict that NP formulations will induce more robust CD4+ and CD8+ T cell responses than peptide alone and that these T cells will recognize target cells infected with each of the different strains of influenza virus. However, we may observe that the extended peptides do not activate CD4 T cells efficiently. In this case, we can expand the peptide lengths to incorporate more residues or add validated CD4 T cell epitopes directly in the formulation. We do not anticipate problems with the experiments themselves as we have extensive experience with the techniques proposed, including influenza virus infection. If any of the above techniques do become problematic, for example due to a cell number issue, we can use multiparameter flow cytometry assessing internal levels of key cytokines (IFN-g, TNF-alpha, Granzyme B) in order to identify activated CD4 and CD8+ T cells within a single culture.

Evaluation of Epitope Specific CD8$^+$ T Cell Responses In Vivo

The HLA-A2 and A24 transgenic mouse (Taconic, Hudson, N.Y.) studies will be outsourced to Lampire Biologics Laboratories (Pipersville, Pa.). Briefly, female mice between 4-8 weeks of age will be immunized with 10 μg of each vaccine formulation containing the extended peptides at two locations: i.d. at the base of the tail and s.c. on the flank. As controls, mice will be immunized with PBS or peptide+montanide adjuvant. All mice will be immunized three times each: at days 0, 10, and 30. Seven days after the final immunization, spleens will be harvested, crushed between sterile frosted glass slides, and filtered through a 0.45 μm mesh filter to obtain single cell suspensions. Single cell suspension will be used to purify CD8+ T cells via negative selection. The cells will be used immediately in the same overnight assays described above in the in vitro section: ELISpot, cytokine secretion, and flow cytometry to detect degranulation. In addition to the functional assays, CD8+ T cell specificities will be assessed using MHC-I tetramer technology as described in Aim 1.

Expected outcome and technical challenges: We expect that we will observe peptide antigen specific T cells activation in vivo in the immunized mice. Further, we predict that mice immunized with the NP formulations will have a more robust T cell response in response to peptide pulsed or infected APCs when compared to PBS or peptide+montanide groups. If we observed that some of the peptides do not induce a response in these mice we can amend the vaccine formulations with additional conserved epitopes in a straightforward manner. We have extensive experience with the HLA-A2 and HLA-A24 transgenic models, therefore we do not anticipate any problems in using these transgenic mouse model systems.

Assess In Vivo Protection of the NP Vaccine Formulations In Virus Challenge Model Using HLA A2 and A24 Transgenic Mice Rationale: In order for a vaccine to be considered effective, it must significantly reduce both the duration and severity of an illness, if not completely prevent a pathogen from establishing infection. Vaccines against multi-strain pathogens, like influenza virus, will be significantly improved if broad protection against most strains can be induced. In this aim, we directly test the NP vaccine formulation containing T and B cell epitopes in a virus challenge model and determine if this vaccine can reduce morbidity and mortality against two different influenza strains. We will perform a complete study with the HLA-A2 transgenic mouse model and if successful, we will repeat the weight loss and lethal challenge studies in HLA-A24 transgenic mouse model.

Methods: To assess in vivo protection after NP vaccine immunization, we will use an influenza challenge model established by our collaborator Dr. Peter Katsikis, Drexel University (76). HLA-A2 transgenic mouse (Taconic, Hudson, N.Y.) strains will be used to assess protection induced by the NP formulated vaccines containing influenza virus specific T and B cell epitopes. Briefly, we plan to use female mice and test the proposed vaccination schedule of 3 immunizations (day 0, 10, and 30). Mice will be immunized with 10 μg of each peptide NP vaccine formulations at two locations: i.d. at the tail base or s.c. on the flank. As controls, peptides with and without adjuvant (Montanide ISA 51) will also be administered.

Following vaccination we will address a number of important questions. Does NP vaccination 1) induces a robust secondary CTL response upon influenza virus challenge, 2) reduce viral loads or accelerate viral clearance, 3) protect from the morbidity induced by a sublethal influenza virus infection and 4) protect against a lethal challenge with a virulent strain of influenza virus? For the morbidity studies we will challenge vaccinated animals 45 days after immunization, with a sublethal dose of the infectious influenza A virus PR8 (H1N1, A/Puerto Rico/8/34). Mice will be infected i.n. and morbidity will be assessed by two means, body weight and virus induced lung pathology. Changes in body weight will be monitored by weighing mice daily over the course of 14 days beginning the day of virus challenge (76, 77). We will use n=9 animals per group (see vertebrate animal section of proposal for power analysis). These numbers will be performed in three independent experiments. Based on preliminary data, when weight loss of wild type animals from day 8-10 post-infection is compared to day 0 the effect size is 20.4%. The effect size for the assuming a 50% reduction in weight loss of vaccinated mice the effect size is 10.2%. Such a difference in effect size (□) with a standard deviation (□) of ~5.2% would require 6 animals per group, for alpha=0.05 at 80% power and two-tailed test. Since an infection may not always be generated or animals may be lost due to anesthesia or infection, we are using 9 mice per experimental group to ensure we will have adequate numbers of animals.

Following PR8 infection, virus induced lung inflammation and pathology will be assessed. At days 6 and 10 post-infection, mice will be sacrificed and lungs harvested. Lungs will be used for pathology and some lobes will be used to prepare collagenase+DNAse digested single cells suspensions. Single cell suspensions will be used to quantify absolute numbers of CD4+ T cells, CD8+ T cells, NK cells, B cells, DC, macrophages and granulocyte infiltrating the lungs. Additionally, the activation profile of these cells will be examined with flow cytometry by staining cell suspensions for CD25, CD69, CD80/86 and MHC-class II. In addition, we will assess lung pathology. Both gross pathological changes based on size, appearance, and color of the lungs and histopathological changes assessed by hematoxylin and eosin staining will be evaluated (78, 79). Lung pathology will allow us to evaluate whether vaccination protected from lung damage. Lung pathology will be evaluated histologically by H&E stain and by staff of the Pathology Department. In addition to measurements of morbidity, viral load in the lungs will be assessed by real-time PCR amplifying the matrix gene of the virus (76) on days 3, 6 and 10 post infection.

Important in the assessment of vaccine efficacy is the determination of whether potent secondary responses are elicited by the vaccine regiment. To assess whether our multi-epitope NP vaccination results in robust secondary responses, we will measure the CD8+ T cell response and the anti-M2e antibody response following influenza virus infection. Lungs and spleens will be harvested on days 3, 6 and 10 post-infection and CD8+ T cell responses will be analyzed by peptide loaded MHC-class I tetramers and peptide-stimulated intracellular IFNγ stains. Blood will be collected at time of harvest and serum M2e antibodies will be measured by ELISA. Neutralizing anti-influenza antibodies in sera will be assayed using a hemagglutination inhibition assay.

Finally, to ensure that NP vaccine formulations can protect against a range of influenza viruses and against lethal challenge, we will perform a lethal challenge with 10× $LD_{50}$ of influenza A virus Eq/Lon (H7N7 A/Equine/London/1416/73), a strain that is highly pathogenic in mice (80, 81). As with PR8 infections, body weight morbidity will be monitored as a read out of protection. In both viral models, B and T cell responses will be analyzed after i.n. challenge. For the lethal challenge studies with Eq/Lon infections we are including n=15 per group (see vertebrate animal section of proposal for power analysis). Power analysis for a probability of survival of 0.6 (60%) in the vaccinated group and 0.1 (10%) in the control group for an alpha of 0.05 at a power of 0.8 and a group ratio of 1, requires a total sample size of 30 animals (15 per group). Following challenge, animals will be monitored twice daily by visual inspection for clinical signs. Animals will be sacrificed when they meet the following criteria: 1) unresponsive to extraneous stimulation, 2) prostration for >1 h, 3) labored breathing, 4) persistent tremors, or 5) persistently hunched. All observations will be recorded. Animals losing >25% weight will be removed and will be counted non-survived in survival analysis. Death will not be an endpoint for this study. (IACUC does not permit death as an endpoint).

Aim 4: Toxicology and Safety Studies

Rationale: Although empty nanoparticles and nanoparticles with insulin peptide have been assessed for safety in human clinical studies (preliminary studies), NPs with any antigenic epitopes have never been tested for safety in humans. Since these epitopes are specific for human HLA-A2 and A24 molecules and have specific biological functions associated with human immune responses, it is critical to also assess the safety of the vaccine formulation in a relevant animal model. As described above, the HLA transgenic mouse model is widely used to assess the in vivo efficacy of epitope based vaccine formulations. In this aim, we will evaluate the safety of the nanoparticles using these transgenic mouse models.

Methods: The nanoparticle vaccine formulation will be administered at various doses (up to 10× of the vaccine dose from aim 3) for 5 consecutive days either intradermally, subcutaneously or intravenously. The volume administered will be 100 μL/animal. Body weights and feed consumption will be monitored over 48 hour periods. Urine and feces samples will be collected over 24 hour periods at different time points during the study and the total urine and feces for each animal will be collected and weighed at room temperature and stored at −80±10° C. Blood samples will be obtained at pre-established times and collected into EDTA K3 tubes and kept in a cold bath until centrifugation (3500 rpm, 10 minutes, 4° C.). The plasma obtained will then be frozen at −80±10° C. Following blood extraction, the animals will be sacrificed to obtain the following tissue samples: brain, liver, kidney, heart, spleen and lung. Tissue samples will be weighed and snap frozen in liquid nitrogen and then stored at −80±10° C. Toxicology analysis of the blood and tissue samples will be performed and all the data will be analyzed for statistical significance. Blood chemistry analysis will be performed with the collected blood samples. Markers for liver function (alanine transaminase, aspartate aminotrasferase, albumin, alkaline phosphatase, total and direct bilirubin, and lactate dehydrogenase), kidney function (blood urea nitrogen, creatinine, uric acid and total protein), and cardiac function (aspartate aminotransferase and lactate dehydrogenase) will be evaluated. In addition, panels of markers for allergy (eosinophils, globulin, lymphocyte and monocyte counts) and hematology disorders (hemoglobin, hematocrit, RBC and WBC counts) will also be included in the test. Tissue samples will also be investigated for gold particle accumulation by transmission electron microscopy (TEM) (82, 83).

REFERENCES

1. Neuzil K M. Influenza: New Insights Into an Old Disease. Curr Infect Dis Rep. 2000; 2(3):224-30. PubMed PMID: 11095860.
2. Mullooly J P, Bennett M D, Hornbrook M C, Barker W H, Williams W W, Patriarca P A, et al. Influenza vaccination programs for elderly persons: cost-effectiveness in a health maintenance organization. Ann Intern Med. 1994; 121(12):947-52. PubMed PMID: 7978721.
3. Hensley S E, Pinto A K, Hickman H D, Kastenmayer R J, Bennink J R, Virgin H W, et al. Murine norovirus infection has no significant effect on adaptive immunity to vaccinia virus or influenza A virus. J Virol. 2009; 83(14): 7357-60. PubMed PMID: 19403665.
4. Murphy B R, Nelson D L, Wright P F, Tierney E L, Phelan M A, Chanock R M. Secretory and systemic immunological response in children infected with live attenuated influenza A virus vaccines. Infect Immun. 1982; 36(3): 1102-8. PubMed PMID: 7095844.
5. Burlington D B, Clements M L, Meiklejohn G, Phelan M, Murphy B R. Hemagglutinin-specific antibody responses in immunoglobulin G, A, and M isotypes as measured by enzyme-linked immunosorbent assay after primary or secondary infection of humans with influenza A virus. Infect Immun. 1983; 41(2):540-5. PubMed PMID: 6874068.
6. Subbarao K, Murphy B R, Fauci A S. Development of effective vaccines against pandemic influenza. Immunity. 2006; 24(1):5-9. PubMed PMID: 16413916.
7. Johansson B E, Bucher D J, Kilbourne E D. Purified influenza virus hemagglutinin and neuraminidase are equivalent in stimulation of antibody response but induce contrasting types of immunity to infection. J Virol. 1989; 63(3):1239-46. PubMed PMID: 2915381.
8. Paul W E, Benacerraf B. Functional specificity of thymus-dependent lymphocytes. Science. 1977; 195(4284):1293-300. PubMed PMID: 320663.
9. Shedlock D J, Shen H. Requirement for CD4 T cell help in generating functional CD8 T cell memory. Science. 2003; 300(5617):337-9. PubMed PMID: 12690201.
10. Ngo-Giang-Huong N, Candotti D, Goubar A, Autran B, Maynart M, Sicard D, et al. HIV type 1-specific IgG2 antibodies: markers of helper T cell type 1 response and prognostic marker of long-term nonprogression. AIDS Res Hum Retroviruses. 2001; 17(15):1435-46. PubMed PMID: 11679156.
11. Heeney J L. Requirement of diverse T-helper responses elicited by HIV vaccines: induction of highly targeted humoral and CTL responses. Expert Rev Vaccines. 2004; 3(4 Suppl):553-64. PubMed PMID: 15285705.
12. Novak E J, Liu A W, Nepom G T, Kwok W W. MHC class II tetramers identify peptide-specific human CD4(+) T cells proliferating in response to influenza A antigen. J Clin Invest. 1999; 104(12):R63-7. PubMed PMID: 10606632.
13. Kamperschroer C, Dibble J P, Meents D L, Schwartzberg P L, Swain S L. SAP is required for Th cell function and for immunity to influenza. J Immunol. 2006; 177(8): 5317-27. PubMed PMID: 17015717.
14. Marshall D, Sealy R, Sangster M, Coleclough C. TH cells primed during influenza virus infection provide help for qualitatively distinct antibody responses to subsequent immunization. J Immunol. 1999; 163(9):4673-82. PubMed PMID: 10528164.
15. McMichael A J, Gotch F M, Noble G R, Beare P A. Cytotoxic T-cell immunity to influenza. N Engl J Med. 1983; 309(1):13-7. PubMed PMID: 6602294.
16. De Groot A S, Ardito M, McClaine E M, Moise L, Martin W D. Immunoinformatic comparison of T-cell epitopes contained in novel swine-origin influenza A (H1N1) virus with epitopes in 2008-2009 conventional influenza vaccine. Vaccine. 2009; 27(42):5740-7. PubMed PMID: 19660593.
17. Greenbaum J. http://iedb.zendesk.com/forums/45499/entries/35037 Knowledgebase and Forums/Epitope analysis in emerging H1N1 swine flu viruses/Analysis version 1.0) 2009.
18. Kilbourne E D. What are the prospects for a universal influenza vaccine? Nat Med. 1999; 5(10):1119-20. PubMed PMID: 10502805.
19. Choppin P W, Tamm I. Studies of two kinds of virus particles which comprise influenza A2 virus strains. II. Reactivity with virus inhibitors in normal sera. J Exp Med. 1960; 112:921-44. PubMed PMID: 13693272.
20. Epstein S L, Misplon J A, Lawson C M, Subbarao E K, Connors M, Murphy B R. Beta 2-microglobulin-deficient mice can be protected against influenza A infection by vaccination with vaccinia-influenza recombinants expressing hemagglutinin and neuraminidase. J Immunol. 1993; 150(12):5484-93. PubMed PMID: 8390536.
21. Price G E, Ou R, Jiang H, Huang L, Moskophidis D. Viral escape by selection of cytotoxic T cell-resistant variants in influenza A virus pneumonia. J Exp Med. 2000; 191(11):1853-67. PubMed PMID: 10839802.

22. Woodland D L, Hogan R J, Zhong W. Cellular immunity and memory to respiratory virus infections. Immunol Res. 2001; 24(1):53-67. PubMed PMID: 11485209.
23. Boon A C, de Mutsert G, Graus Y M, Fouchier R A, Sintnicolaas K, Osterhaus A D, et al. Sequence variation in a newly identified HLA-B35-restricted epitope in the influenza A virus nucleoprotein associated with escape from cytotoxic T lymphocytes. J Virol. 2002; 76(5):2567-72. PubMed PMID: 11836437.
24. Ben-Yedidia T, Marcus H, Reisner Y, Arnon R. Intranasal administration of peptide vaccine protects human/mouse radiation chimera from influenza infection. Int Immunol. 1999; 11(7):1043-51. PubMed PMID: 10383936.
25. Jameson J, Cruz J, Ennis F A. Human cytotoxic T-lymphocyte repertoire to influenza A viruses. J Virol. 1998; 72(11):8682-9. PubMed PMID: 9765409.
26. Kanekiyo M, Wei C J, Yassine H M, McTamney P M, Boyington J C, Whittle J R, et al. Self-assembling influenza nanoparticle vaccines elicit broadly neutralizing H1N1 antibodies. Nature. 2013; 499(7456):102-6. Epub 2013 May 24. doi: 10.1038/nature12202. PubMed PMID: 23698367.
27. Pleguezuelos O, Robinson S, Stoloff G A, Caparros-Wanderley W. Synthetic Influenza vaccine (FLU-v) stimulates cell mediated immunity in a double-blind, randomised, placebo-controlled Phase I trial. Vaccine. 2012; 30(31):4655-60. Epub 2012 May 12. doi: 10.1016/j.vaccine.2012.04.089. PubMed PMID: 22575166.
28. Wilkinson T M, Li C K, Chui C S, Huang A K, Perkins M, Liebner J C, et al. Preexisting influenza-specific CD4+ T cells correlate with disease protection against influenza challenge in humans. Nat Med. 2012; 18(2):274-80. Epub 2012 Jan. 31. doi: 10.1038/nm.2612. PubMed PMID: 22286307.
29. Atsmon J, Kate-Ilovitz E, Shaikevich D, Singer Y, Volokhov I, Haim K Y, et al. Safety and immunogenicity of multimeric-001—a novel universal influenza vaccine. Journal of clinical immunology. 2012; 32(3):595-603. Epub 2012/02/10. doi: 10.1007/s10875-011-9632-5. PubMed PMID: 22318394.
30. Tao W, Ziemer K S, Gill H S. Gold nanoparticle-M2e conjugate coformulated with CpG induces protective immunity against influenza A virus. Nanomedicine (Lond). 2013. Epub 2013 Jul. 9. doi: 10.2217/nnm.13.58. PubMed PMID: 23829488.
31. Testa J S, Philip R. Role of T-cell epitope-based vaccine in prophylactic and therapeutic applications. Future virology. 2012; 7(11):1077-88. Epub 2013 May 1. doi: 10.2217/fvl.12.108. PubMed PMID: 23630544; PubMed Central PMCID: PMC3636528.
32. Fifis T, Gamvrellis A, Crimeen-Irwin B, Pietersz G A, Li J, Mottram P L, et al. Size-dependent immunogenicity: therapeutic and protective properties of nano-vaccines against tumors. J Immunol. 2004; 173(5):3148-54. PubMed PMID: 15322175.
33. Reddy S T, van der Vlies A J, Simeoni E, Angeli V, Randolph G J, O'Neil C P, et al. Exploiting lymphatic transport and complement activation in nanoparticle vaccines. Nat Biotechnol. 2007; 25(10):1159-64. PubMed PMID: 17873867.
34. Testa J S, Shetty V, Hafner J, Nickens Z, Kamal S, Sinnathamby G, et al. MHC class I-presented T cell epitopes identified by immunoproteomics analysis are targets for a cross reactive influenza-specific T cell response. PLoS One. 2012; 7(11):e48484. Epub 2012 Nov. 13. doi: 10.1371/journal.pone.0048484. PubMed PMID: 23144892; PubMed Central PMCID: PMC3492461.
35. Ojeda R, de Paz J L, Barrientos A G, Martin-Lomas M, Penades S. Preparation of multifunctional glyconanoparticles as a platform for potential carbohydrate-based anti-cancer vaccines. Carbohydr Res. 2007; 342(3-4):448-59. PubMed PMID: 17173881.
36. Kircheis R, Vondru P, Zinocker I, Haring D, Nechansky A, Loibner H, et al. Immunization of Rhesus monkeys with the conjugate vaccine IGN402 induces an IgG immune response against carbohydrate and protein antigens, and cancer cells. Vaccine. 2006; 24(13):2349-57. PubMed PMID: 16406172.
37. Beyer M, Schultze J L. Immunoregulatory T cells: role and potential as a target in malignancy. Curr Oncol Rep. 2008; 10(2):130-6. PubMed PMID: 18377826.
38. Dredge K, Marriott J B, Todryk S M, Dalgleish A G. Adjuvants and the promotion of Th1-type cytokines in tumour immunotherapy. Cancer Immunol Immunother. 2002; 51(10):521-31. PubMed PMID: 12384803.
39. Thomas P G, Brown S A, Keating R, Yue W, Morris M Y, So J, et al. Hidden epitopes emerge in secondary influenza virus-specific CD8+ T cell responses. J Immunol. 2007; 178(5):3091-8. PubMed PMID: 17312156.
40. Huang Q, Liu D, Majewski P, Schulte L C, Korn J M, Young R A, et al. The plasticity of dendritic cell responses to pathogens and their components. Science. 2001; 294 (5543):870-5. PubMed PMID: 11679675.
41. Fonteneau J F, Gilliet M, Larsson M, Dasilva I, Munz C, Liu Y J, et al. Activation of influenza virus-specific CD4+ and CD8+ T cells: a new role for plasmacytoid dendritic cells in adaptive immunity. Blood. 2003; 101(9):3520-6. PubMed PMID: 12511409.
42. Man S, Newberg M H, Crotzer V L, Luckey C J, Williams N S, Chen Y, et al. Definition of a human T cell epitope from influenza A non-structural protein 1 using HLA-A2.1 transgenic mice. Int Immunol. 1995; 7(4):597-605. Epub 1995 Apr. 1. PubMed PMID: 7547687.
43. Gras S, Kedzierski L, Valkenburg S A, Laurie K, Liu Y C, Denholm J T, et al. Cross-reactive CD8+ T-cell immunity between the pandemic H1N1-2009 and H1N1-1918 influenza A viruses. Proc Natl Acad Sci USA. 2010; 107(28):12599-604. Epub 2010 Jul. 10. doi: 10.1073/pnas.1007270107. PubMed PMID: 20616031; PubMed Central PMCID: PMC2906563.
44. Mittendorf E A, Storrer C E, Shriver C D, Ponniah S, Peoples G E. Evaluation of the CD107 cytotoxicity assay for the detection of cytolytic CD8+ cells recognizing HER2/neu vaccine peptides. Breast cancer research and treatment. 2005; 92(1):85-93. Epub 2005 Jun. 28. doi: 10.1007/s10549-005-0988-1. PubMed PMID: 15980996.
45. Betts M R, Brenchley J M, Price D A, De Rosa S C, Douek D C, Roederer M, et al. Sensitive and viable identification of antigen-specific CD8+ T cells by a flow cytometric assay for degranulation. J Immunol Methods. 2003; 281(1-2):65-78. Epub 2003 Oct. 29. PubMed PMID: 14580882.
46. Fiers W, De Filette M, Birkett A, Neirynck S, Min Jou W. A "universal" human influenza A vaccine. Virus research. 2004; 103(1-2):173-6. Epub 2004 May 28. doi: 10.1016/j.virusres.2004.02.030. PubMed PMID: 15163506.
47. Grandea A G, 3rd, Olsen O A, Cox T C, Renshaw M, Hammond P W, Chan-Hui P Y, et al. Human antibodies reveal a protective epitope that is highly conserved among human and nonhuman influenza A viruses. Proc Natl Acad 48. Wherry E J, Puorro K A, Porgador A, Eisenlohr L C. The induction of virus-specific CTL as a function of increasing epitope expression: responses rise steadily until excessively high levels of epitope are attained. J Immunol. 1999; 163(7):3735-45. PubMed PMID: 10490969.
49. Ramakrishna V, Ross M, Petersson M, Gatlin C, Lyons C, Miller C, et al. Naturally occurring peptides associated with HLA-A2 in ovarian cancer cell lines identified by mass spectrometry are targets of HLA-A2-restricted cytotoxic T cells. Int Immunol. 2003; 15(6).
50. Philip R, Murthy S, Krakover J, Sinnathamby G, Zerfass J, Keller L, et al. Shared immunoproteome for ovarian cancer diagnostics and immunotherapy: potential theranostic approach to cancer. J Proteome Res. 2007; 6(7): 2509-17. PubMed PMID: 17547437.
51. Sinnathamby G, Lauer, P., Zerfass, J., Hanson, B., Karabudak, A., Krakover, J., Secord, A. A., Clay, T. M., Morse, M. A., Dubensky, T. W., Brockstedt D. G., Philip, R., and Giedlin, M. Priming and Activation of human ovarian and breast cancer-specific CD8+ T cells by polyvalent *Listeria monocytogenes*-based vaccines. J Immunotherapy. 2009; 32(8):856-69.
52. Karkada M, Weir, G. M., Quinton, T., Sammatur, L., MacDonald, L. D., Grant, A., Liwski, R., Juskevicius, R., Sinnathamby, G., Phillip, R., Mansour, M. A Novel Breast/Ovarian Cancer Peptide Vaccine Platform that Promotes Specific Type-1 but not Treg/Tr1-Type Responses J Immunotherapy. 2009:in press.
53. Morse M A, Alvarez Secord A, Blackwell K L, Hobeika A, Sinnathamby G, Osada T, et al. MHC class I-presented tumor antigens identified in ovarian cancer by immunoproteomic analysis are targets for T cell responses against breast and ovarian cancer. Clin Cancer Res. PubMed PMID: 21300761.
54. Shetty V, Sinnathamby G, Nickens Z, Shah P, Hafner J, Mariello L, et al. MHC class I-presented lung cancer-associated tumor antigens identified by immunoproteomics analysis are targets for cancer-specific T cell response. J Proteomics. 74(5):728-43. PubMed PMID: 21362506.
55. Testa J S, Shetty V, Sinnathamby G, Nickens Z, Hafner J, Kamal S, et al. Conserved MHC class I-presented dengue virus epitopes identified by immunoproteomics analysis are targets for cross-serotype reactive T-cell response. J Infect Dis. 2012; 205(4):647-55. Epub 2012 Jan. 17. doi: 10.1093/infdis/jir814. PubMed PMID: 22246683.
56. Meidenbauer N, Marienhagen J, Laumer M, Vogl S, Heymann J, Andreesen R, et al. Survival and tumor localization of adoptively transferred Melan-A-specific T cells in melanoma patients. J Immunol. 2003; 170(4): 2161-9. PubMed PMID: 12574389.
57. Batard P, Peterson D A, Devevre E, Guillaume P, Cerottini J C, Rimoldi D, et al. Dextramers: new generation of fluorescent MHC class I/peptide multimers for visualization of antigen-specific CD8+ T cells. J Immunol Methods. 2006; 310(1-2):136-48. PubMed PMID: 16516226.
58. Ramakrishna V, Ross M M, Petersson M, Gatlin C C, Lyons C E, Miller C L, et al. Naturally occurring peptides associated with HLA-A2 in ovarian cancer cell lines identified by mass spectrometry are targets of HLA-A2-restricted cytotoxic T cells. Int Immunol. 2003; 15(6): 751-63. PubMed PMID: 12750359.
59. Morse M A, Nair S K, Mosca P J, Hobeika A C, Clay T M, Deng Y, et al. Immunotherapy with autologous, human dendritic cells transfected with carcinoembryonic antigen mRNA. Cancer Invest. 2003; 21(3):341-9. PubMed PMID: 12901279.
60. Doherty P C, Allan W, Eichelberger M, Carding S R. Roles of alpha beta and gamma delta T cell subsets in viral immunity. Annu Rev Immunol. 1992; 10:123-51. PubMed PMID: 1534240.
61. Eichelberger M, Allan W, Zijlstra M, Jaenisch R, Doherty P C. Clearance of influenza virus respiratory infection in mice lacking class I major histocompatibility complex-restricted CD8+ T cells. J Exp Med. 1991; 174(4):875-80. PubMed PMID: 1919440.
62. Epstein S L, Lo C Y, Misplon J A, Bennink J R. Mechanism of protective immunity against influenza virus infection in mice without antibodies. J Immunol. 1998; 160(1):322-7. PubMed PMID: 9551987.
63. Graham M B, Braciale T J. Resistance to and recovery from lethal influenza virus infection in B lymphocyte-deficient mice. J Exp Med. 1997; 186(12):2063-8. PubMed PMID: 9396777.
64. Rimmelzwaan G F, Osterhaus A D. Cytotoxic T lymphocyte memory: role in cross-protective immunity against influenza? Vaccine. 1995; 13(8):703-5. PubMed PMID: 7483784.
65. Yewdell J W, Bennink J R, Smith G L, Moss B. Influenza A virus nucleoprotein is a major target antigen for cross-reactive anti-influenza A virus cytotoxic T lymphocytes. Proc Natl Acad Sci USA. 1985; 82(6):1785-9. PubMed PMID: 3872457.
66. Tan P T, Khan A M, August J T. Highly conserved influenza A sequences as T cell epitopes-based vaccine targets to address the viral variability. Hum Vaccin. 2011; 7(4):402-9. Epub 2011 Apr. 8. PubMed PMID: 21471731.
67. Yap K L, Braciale T J, Ada G L. Role of T-cell function in recovery from murine influenza infection. Cell Immunol. 1979; 43(2):341-51. PubMed PMID: 113108.
68. Yap K L, Ada G L, McKenzie I F. Transfer of specific cytotoxic T lymphocytes protects mice inoculated with influenza virus. Nature. 1978; 273(5659):238-9. PubMed PMID: 306072.
69. Stambas J, Guillonneau C, Kedzierska K, Mintern J D, Doherty P C, La Gruta N L. Killer T cells in influenza. Pharmacology & therapeutics. 2008; 120(2):186-96. Epub 2008 Sep. 20. doi: 10.1016/j.pharmthera.2008.08.007. PubMed PMID: 18801385.
70. Sun J, Madan R, Karp C L, Braciale T J. Effector T cells control lung inflammation during acute influenza virus infection by producing IL-10. Nat Med. 2009; 15(3):277-84. Epub 2009 Feb. 24. doi: 10.1038/nm.1929. PubMed PMID: 19234462; PubMed Central PMCID: PMC2693210.
71. McKinstry K K, Strutt T M, Swain S L. Hallmarks of CD4 T cell immunity against influenza. Journal of internal medicine. 2011; 269(5):507-18. Epub 2011 Mar. 3. doi: 10.1111/j.1365-2796.2011.02367.x. PubMed PMID: 21362069; PubMed Central PMCID: PMC3395075.
72. Richards K A, Topham D, Chaves F A, Sant A J. Cutting edge: CD4 T cells generated from encounter with seasonal influenza viruses and vaccines have broad protein specificity and can directly recognize naturally generated epitopes derived from the live pandemic H1N1 virus. J Immunol. 2010; 185(9):4998-5002. Epub 2010 Oct. 5. doi: 10.4049/jimmunol.1001395. PubMed PMID: 20889549.

73. Lee L Y, Ha do L A, Simmons C, de Jong M D, Chau N V, Schumacher R, et al. Memory T cells established by seasonal human influenza A infection cross-react with avian influenza A (H5N1) in healthy individuals. J Clin Invest. 2008; 118(10):3478-90. Epub 2008 Sep. 20. doi: 10.1172/JCI32460. PubMed PMID: 18802496; PubMed Central PMCID: PMC2542885.
74. Roti M, Yang J, Berger D, Huston L, James E A, Kwok W W. Healthy human subjects have CD4+ T cells directed against H5N1 influenza virus. J Immunol. 2008; 180(3): 1758-68. Epub 2008 Jan. 23. PubMed PMID: 18209073; PubMed Central PMCID: PMC3373268.
75. Kreijtz J H, Bodewes R, van Amerongen G, Kuiken T, Fouchier R A, Osterhaus A D, et al. Primary influenza A virus infection induces cross-protective immunity against a lethal infection with a heterosubtypic virus strain in mice. Vaccine. 2007; 25(4):612-20. PubMed PMID: 17005299.
76. Boesteanu A C, Babu N S, Wheatley M, Papazoglou E S, Katsikis P D. Biopolymer encapsulated live influenza virus as a universal CD8+ T cell vaccine against influenza virus. Vaccine. 2010; 29(2):314-22. Epub 2010 Nov. 3. doi: 10.1016/j.vaccine.2010.10.036. PubMed PMID: 21034826; PubMed Central PMCID: PMC3004745.
77. Manicassamy B, Manicassamy S, Belicha-Villanueva A, Pisanelli G, Pulendran B, Garcia-Sastre A. Analysis of in vivo dynamics of influenza virus infection in mice using a GFP reporter virus. Proc Natl Acad Sci USA. 2010; 107(25):11531-6. Epub 2010 Jun. 11. doi: 10.1073/pnas.0914994107. PubMed PMID: 20534532; PubMed Central PMCID: PMC2895123.
78. Fukushi M, I to T, Oka T, Kitazawa T, Miyoshi-Akiyama T, Kirikae T, et al. Serial histopathological examination of the lungs of mice infected with influenza A virus PR8 strain. PLoS One. 2011; 6(6):e21207. Epub 2011 Jun. 28. doi: 10.1371/journal.pone.0021207. PubMed PMID: 21701593; PubMed Central PMCID: PMC3118813.
79. Shirey K A, Lai W, Scott A J, Lipsky M, Mistry P, Pletneva L M, et al. The TLR4 antagonist Eritoran protects mice from lethal influenza infection. Nature. 2013; 497(7450):498-502. Epub 2013 May 3. doi: 10.1038/nature12118. PubMed PMID: 23636320.
80. Kawaoka Y. Equine H7N7 influenza A viruses are highly pathogenic in mice without adaptation: potential use as an animal model. J Virol. 1991; 65(7):3891-4. PubMed PMID: 2041098.
81. Christensen J P, Doherty P C, Branum K C, Riberdy J M. Profound protection against respiratory challenge with a lethal H7N7 influenza A virus by increasing the magnitude of CD8(+) T-cell memory. J Virol. 2000; 74(24): 11690-6. PubMed PMID: 11090168.
82. Brandenberger C, Rothen-Rutishauser B, Muhlfeld C, Schmid O, Ferron G A, Maier K L, et al. Effects and uptake of gold nanoparticles deposited at the air-liquid interface of a human epithelial airway model. Toxicol Appl Pharmacol. 242(1):56-65. PubMed PMID: 19796648.
83. Uboldi C, Bonacchi D, Lorenzi G, Hermanns M I, Pohl C, Baldi G, et al. Gold nanoparticles induce cytotoxicity in the alveolar type-II cell lines A549 and NCIH441. Part Fibre Toxicol. 2009; 6:18. PubMed PMID: 19545423.

The invention claimed is:

1. A vaccine composition comprising an influenza virus peptide comprising one or more of the CD8+ T cell epitopes set out in SEQ ID NOs: 1 to 21, wherein the peptide is attached to a gold glyconanoparticle, and wherein the glyconanoparticle further comprises one or more ligands comprising a carbohydrate moiety selected from the group consisting of: glucose, N-Acetylglucosamine (GlcNAc), 2'-thioethyl-β-D-glucopyranoside, and 2'-thioethyl-D-glucopyranoside.

2. The vaccine composition of claim 1, wherein the influenza virus peptide comprising a CD8+ T cell epitope is attached to the nanoparticle via a linker.

3. The vaccine composition of claim 1, which comprises two or more influenza virus peptides each comprising a different CD8+ T cell epitope.

4. The vaccine composition of claim 3, wherein the two or more influenza virus peptides are two or more of the peptides set out in SEQ ID NOs: 1 to 21.

5. The vaccine composition of claim 1, further comprising an influenza virus peptide comprising a CD4+ T cell epitope.

6. The vaccine composition of claim 5, wherein the influenza virus peptide comprising a CD4+ T cell epitope is attached to a nanoparticle, optionally wherein the nanoparticle to which the influenza virus peptide comprising a CD4+ T cell epitope is attached is a gold nanoparticle, a calcium phosphate nanoparticle, or a silicon nanoparticle, and optionally wherein the influenza virus peptide comprising a CD4+ T cell epitope is attached to the nanoparticle via a linker.

7. The vaccine composition of claim 1, wherein the influenza virus peptide comprising a CD8+ T cell epitope further comprises a CD4+ T cell epitope.

8. The vaccine composition of claim 7, wherein the influenza virus peptide comprising a CD8+ T cell epitope and a CD4+ T cell epitope comprises one or more of the peptides set out in SEQ ID NOs: 22 to 27.

9. The vaccine composition of claim 1, comprising at least two influenza virus peptides comprising a CD8+ T cell epitope which each interacts with a different HLA supertype.

10. The vaccine composition claim 1, which comprises at least one immunogenic peptide that interacts with at least two different HLA supertypes.

11. The vaccine composition of claim 9, wherein the at least two different HLA supertypes are selected from HLA-A1, HLA-A2, HLA-A3, HLA-A24, HLA-B7, HLA-B8, HLA-B27, HLA-B44, HLA-B58 and HLA-B62.

12. The vaccine composition of claim 11, wherein the at least two different HLA supertypes are HLA-A2 and HLA-A24.

* * * * *

SEQUENCE LISTING

<160> NUMBER OF SEQ ID NOS: 31

<210> SEQ ID NO 1
<211> LENGTH: 11
<212> TYPE: PRT
<213> ORGANISM: Influenza virus

<400> SEQUENCE: 1

Pro Val Ala Gly Gly Thr Ser Ser Ile Tyr Ile
1               5                   10

<210> SEQ ID NO 2
<211> LENGTH: 8
<212> TYPE: PRT
<213> ORGANISM: Influenza virus

<400> SEQUENCE: 2

Thr Val Ile Lys Thr Asn Met Ile
1               5

<210> SEQ ID NO 3
<211> LENGTH: 9
<212> TYPE: PRT
<213> ORGANISM: Influenza virus

<400> SEQUENCE: 3

Met Thr Ile Ile Phe Leu Ile Leu Met
1               5

<210> SEQ ID NO 4
<211> LENGTH: 9
<212> TYPE: PRT
<213> ORGANISM: Influenza virus

<400> SEQUENCE: 4

Ile Thr Phe His Gly Ala Lys Glu Ile
1               5

<210> SEQ ID NO 5
<211> LENGTH: 9
<212> TYPE: PRT
<213> ORGANISM: Influenza virus

<400> SEQUENCE: 5

Ala Ile Asn Gly Ile Thr Asn Lys Val
1               5

<210> SEQ ID NO 6
<211> LENGTH: 9
<212> TYPE: PRT
<213> ORGANISM: Influenza virus

<400> SEQUENCE: 6

Glu Glu Met Gly Ile Thr Thr His Phe
1               5

<210> SEQ ID NO 7
<211> LENGTH: 9
<212> TYPE: PRT
<213> ORGANISM: Influenza virus

<400> SEQUENCE: 7

Val Glu Thr Pro Ile Arg Asn Glu Trp
1               5

<210> SEQ ID NO 8
<211> LENGTH: 9
<212> TYPE: PRT
<213> ORGANISM: Influenza virus

<400> SEQUENCE: 8

Arg Glu Ile Leu Thr Lys Thr Thr Val
1               5

<210> SEQ ID NO 9
<211> LENGTH: 15
<212> TYPE: PRT
<213> ORGANISM: Influenza virus

<400> SEQUENCE: 9

Lys Glu Ser Asp Glu Ala Leu Asn Met Thr Met Ala Ser Thr Pro
1               5                   10                  15

<210> SEQ ID NO 10
<211> LENGTH: 9
<212> TYPE: PRT
<213> ORGANISM: Influenza virus

<400> SEQUENCE: 10

Leu Glu Asn Glu Arg Thr Leu Asp Phe
1               5

<210> SEQ ID NO 11
<211> LENGTH: 9
<212> TYPE: PRT
<213> ORGANISM: Influenza virus

<400> SEQUENCE: 11

Met Glu Ala Val Pro Leu Ile Thr Ile
1               5

<210> SEQ ID NO 12
<211> LENGTH: 8
<212> TYPE: PRT
<213> ORGANISM: Influenza virus

<400> SEQUENCE: 12

Val Glu Gln Glu Ile Arg Thr Phe
1               5

<210> SEQ ID NO 13
<211> LENGTH: 8
<212> TYPE: PRT
<213> ORGANISM: Influenza virus

<400> SEQUENCE: 13

Val Glu Gln Glu Leu Arg Thr Phe
1               5

<210> SEQ ID NO 14
<211> LENGTH: 11
<212> TYPE: PRT
<213> ORGANISM: Influenza virus

<400> SEQUENCE: 14

Ser Pro Asp Asp Phe Ala Leu Ile Val Asn Ala
1               5                   10

<210> SEQ ID NO 15
<211> LENGTH: 8
<212> TYPE: PRT
<213> ORGANISM: Influenza virus

<400> SEQUENCE: 15

Tyr Pro Asp Thr Gly Lys Val Met
1               5

<210> SEQ ID NO 16
<211> LENGTH: 8
<212> TYPE: PRT
<213> ORGANISM: Influenza virus

<400> SEQUENCE: 16

Tyr Pro Asp Ala Ser Lys Val Met
1               5

<210> SEQ ID NO 17
<211> LENGTH: 10
<212> TYPE: PRT
<213> ORGANISM: Influenza virus

<400> SEQUENCE: 17

Gln Pro Glu Thr Cys Asn Gln Ser Ile Ile
1               5                   10

<210> SEQ ID NO 18
<211> LENGTH: 9
<212> TYPE: PRT
<213> ORGANISM: Influenza virus

<400> SEQUENCE: 18

Val Pro Glu Ser Lys Arg Met Ser Leu

-continued

```
<210> SEQ ID NO 19
<211> LENGTH: 9
<212> TYPE: PRT
<213> ORGANISM: Influenza virus

<400> SEQUENCE: 19

Tyr Ile Asn Thr Ala Leu Leu Asn Ala
1               5

<210> SEQ ID NO 20
<211> LENGTH: 9
<212> TYPE: PRT
<213> ORGANISM: Influenza virus

<400> SEQUENCE: 20

Ala Ile Met Asp Lys Asn Ile Ile Leu
1               5

<210> SEQ ID NO 21
<211> LENGTH: 9
<212> TYPE: PRT
<213> ORGANISM: Influenza virus

<400> SEQUENCE: 21

Leu Pro Phe Asp Arg Thr Thr Ile Met
1               5

<210> SEQ ID NO 22
<211> LENGTH: 15
<212> TYPE: PRT
<213> ORGANISM: Influenza virus

<400> SEQUENCE: 22

Lys Gly Val Tyr Ile Asn Thr Ala Leu Leu Asn Ala Ser Cys Ala
1               5                   10                  15

<210> SEQ ID NO 23
<211> LENGTH: 17
<212> TYPE: PRT
<213> ORGANISM: Influenza virus

<400> SEQUENCE: 23

Arg Phe Leu Pro Val Ala Gly Gly Thr Ser Ser Ile Tyr Ile Glu Val
1               5                   10                  15

Leu

<210> SEQ ID NO 24
<211> LENGTH: 14
<212> TYPE: PRT
<213> ORGANISM: Influenza virus

<400> SEQUENCE: 24

Ile Gly Val Thr Val Ile Lys Thr Asn Met Ile Asn Asn Asp
1               5                   10

<210> SEQ ID NO 25
<211> LENGTH: 15
<212> TYPE: PRT
<213> ORGANISM: Influenza virus

<400> SEQUENCE: 25

Met Asp Gln Ala Ile Met Asp Lys Asn Ile Ile Leu Lys Ala Asn
```

```
<210> SEQ ID NO 26
<211> LENGTH: 15
<212> TYPE: PRT
<213> ORGANISM: Influenza virus

<400> SEQUENCE: 26

Lys Arg Glu Ile Thr Phe His Gly Ala Lys Glu Ile Ser Leu Ser
1               5                   10                  15

<210> SEQ ID NO 27
<211> LENGTH: 15
<212> TYPE: PRT
<213> ORGANISM: Influenza virus

<400> SEQUENCE: 27

Thr Gln Asn Ala Ile Asn Gly Ile Thr Asn Lys Val Asn Ser Val
1               5                   10                  15

<210> SEQ ID NO 28
<211> LENGTH: 4
<212> TYPE: PRT
<213> ORGANISM: Artificial Sequence
<220> FEATURE:
<223> OTHER INFORMATION: OVA peptide used in the Examples

<400> SEQUENCE: 28

Ser Ile Ile Asn
1

<210> SEQ ID NO 29
<211> LENGTH: 5
<212> TYPE: PRT
<213> ORGANISM: Artificial Sequence
<220> FEATURE:
<223> OTHER INFORMATION: Linker sequence

<400> SEQUENCE: 29

Phe Leu Ala Ala Tyr
1               5

<210> SEQ ID NO 30
<211> LENGTH: 8
<212> TYPE: PRT
<213> ORGANISM: Artificial Sequence
<220> FEATURE:
<223> OTHER INFORMATION: OVA peptide used in the Examples

<400> SEQUENCE: 30

Ser Ile Ile Asn Phe Glu Lys Leu
1               5

<210> SEQ ID NO 31
<211> LENGTH: 14
<212> TYPE: PRT
<213> ORGANISM: Artificial Sequence
<220> FEATURE:
<223> OTHER INFORMATION: OVA peptide used in the Examples

<400> SEQUENCE: 31

Gln Leu Glu Ser Ile Ile Asn Phe Glu Lys Leu Thr Glu Trp
1               5                   10
```